(12) United States Patent
Dosch

(10) Patent No.: US 6,207,389 B1
(45) Date of Patent: Mar. 27, 2001

(54) METHODS OF CONTROLLING T LYMPHOCYTE MEDIATED IMMUNE RESPONSES

(75) Inventor: Hans Michael Dosch, Toronto (CA)

(73) Assignee: HRC Research and Development Limited Partnership, Ontario (CA)

( * ) Notice: Subject to any disclaimer, the term of this patent is extended or adjusted under 35 U.S.C. 154(b) by 0 days.

(21) Appl. No.: 08/477,928

(22) Filed: Jun. 7, 1995

Related U.S. Application Data

(63) Continuation-in-part of application No. 08/237,363, filed on May 3, 1994, which is a continuation-in-part of application No. PCT/CA95/00264, filed on May 3, 1995.

(51) Int. Cl.[7] .......................... G01N 33/53; C07K 14/00
(52) U.S. Cl. ................. 435/7.1; 435/6; 530/300; 530/350; 530/327
(58) Field of Search ..................... 435/6, 7.1; 530/300, 530/350, 327

(56) References Cited

PUBLICATIONS

Newsom–Davis et al. J. of Autoimmunity 2:101, 1989.*
Martin et al J. of Immunology 148:1359, 1992.*
Roep et al Eur. J. of Immunol. 26:1285, 1996.*
Karin et al. J. of Exp. Med. 180:2227, 1994.*
Karjalainen et al Diabetetologia 35:985, 1992.*
Ivarsson et al Diabetes 44:1349 1995.*
Karjalainen et al New Eng J. of Medicine 327:302, 1992.*
Pietropaolo et al J. Clin Invest. 92:359 1993.*
Roep et al. 1991 Lancet 337:1439.*

* cited by examiner

Primary Examiner—Thomas M. Cunningham
Assistant Examiner—Martha T. Lubet
(74) Attorney, Agent, or Firm—Baker & Botts LLP

(57) ABSTRACT

Methods and compositions are provided for preventing the development of a T cell mediated autoimmune disease such as Type I diabetes, in which susceptible subjects have T cells sensitized to a disease-related antigen. Subjects are treated by administration of the antigen or fragments thereof to prevent the expansion of the population of sensitized T cells. Alternatively, subjects are treated by administration of immunogenic compositions comprising a mimicry antigen or fragments thereof.

9 Claims, 47 Drawing Sheets

FIG. 1a.

```
 -76  ATAATATAAC TTATCCTCTC ATGCTTTTTT CCTGCCCCTT CTCCCCAAAT CATCAACAAT  -17
 -16  AGAAGAAGAA GAAAAC                                                   -1
   1  ATGTCAGGAC ACAAATGCAG TTATCCCTGG GACTTACAGG ATCGATATGC TCAAGATAAG   60
  61  TCAGTTGTAA ATAAGATGCA ACAGAAATAT TGGGAGACGA AGCAGGCCTT TATTAAAGCC  120
 121  ACAGGGAAGA AGGAAGATGA ACATGTTGTT GCCTCTGACG CGGACCTGGA TGCCAAGCTA  180
 181  GAGCTGTTTC ATTCAATTCA GAGAACCTGT CTGGACTTAT CGAAAGCAAT TGTACTCTAT  240
 241  CAAAAGGGGA TATGTTTCTT GTCTCAAGAA GAAAACGAAC TGGGAAAATT TCTTCGATCC  300
 301  CAAGGTTTCC AAGATAAAAC CAGAGCAGGA AAGATGATGC AAGCGACAGG AAAGGCCCTC  360
 361  TGCTTTTCTT CCCAGCAAAG GTTGGCCTTA CGAAATCCTT TGTGTCGATT TCACCAAGAA  420
 421  GTGGAGACTT TTCGGCATCG GGCCATCTCA GATACTTGGC TGACGGTGAA CCGCATGGAA  480
 481  CAGTGCAGGA CGGAATATAG AGGAGCACTA TTATGGATGA AGGACGTGTC TCAGGAGCTT  540
 541  GATCCAGACC TCTACAAGCA AATGGAGAAG TTCAGGAAGG TACAAACACA AGTGCGCCTT  600
 601  GCAAAAAAAA ACTTTGACAA ATTGAAGATG GATGTTTGTC AAAAAGTGGA TCTTCTTGGA  660
 661  GCGAGCAGAT GCAATCTCTT GTCTCACATG CTAGCAACAT ACCAGACCAC TCTGCTTCAT  720
 721  TTTTGGGAGA AAACTTCTCA CACTATGGCA GCCATCCATG AGAGTTTCAA AGGTTATCAA  780
 781  CCATATGAAT TTACTACTTT AAAGAGCTTA CAAGACCCTA TGAAAAAATT AGTTGAGAAA  840
 841  GAAGAGAAGA AGAAAATCAA CCAGCAGGAA AGTACAGATG CAGCCGTGCA GGAGCCGAGC  900
 901  CAATTAATTT CATTAGAGGA AGAAAACCAG CGCAAGGAAT CCTCTAGTTT TAAGACTGAA  960
 961  GATGGAAAAA GTATTTTATC TGCCTTAGAC AAAGGCTCTA CACATACTGC ATGCTCAGGA 1020
1021  CCCATAGATG AACTATTAGA CATGAAATCT GAGGAAGGTG CTTGCCTGGG ACCAGTGGCA 1080
1081  GGGACCCCGG AACCTGAAGG TGCTGACAAA GATGACCTGC TGCTGTTGAG TGAGATCTTC 1140
1141  AATGCTTCCT CCTTGGAAGA GGGCGAGTTC AGCAAAGAGT GGGCCGCTGT GTTTGGAGAC 1200
1201  GGCCAAGTGA AGGAGCCAGT GCCCACTATG GCCCTGGGAG AGCCAGACCC CAAGGCCCAG 1260
1261  ACAGGCTCAG GTTTCCTTCC TTCGCAGCTT TTAGACCAAA ATATGAAAGA CTTACAGGCC 1320
1321  TCGCTACAAG AACCTGCTAA GGCTGCCTCA GACCTGACTG CCTGGTTCAG CCTCTTCGCT 1380
1381  GACCTCGACC CACTCTCAAA TCCTGATGCT GTTGGGAAAA CCGATAAAGA ACACGAATTG 1440
1441  CTCAATGCAT GA                                                      1452
```

FIG. 1b.

```
  1  MSGHKCSYPW DLQDRYAQDK SVVNKMQQKY WETKQAFIKA TGKKEDEHVV ASDADLDAKL
 61  ELFHSIQRTC LDLSKAIVLY QKGICFLSQE ENELGKFLRS QGFQDKTRAG KMMQATGKAL
121  CFSSQQRLAL RNPLCRFHQE VETFRHRAIS DTWLTVNRME QCRTEYRGAL LWMKDVSQEL
181  DPDLYKQMEK FRKVQTQVRL AKKNFDKLKM DVCQKVDLLG ASRCNLLSHM LATYQTTLLH
241  FWEKTSHTMA AIHESFKGYQ PYEFTTLKSL QDPMKKLVEK EEKKINQQE  STDAAVQEPS
301  QLISLEEENQ RKESSSFKTE DGKSILSALD KGSTHTACSG PIDELLDMKS EEGACLGPVA
361  GTPEPEGADK DDLLLLSEIF NASSLEEGEF SKEWAAVFGD GQVKEPVPTM ALGEPDPKAQ
421  TGSGFLPSQL LDQNMKDLQA SLQEPAKAAS DLTAWFSLFA DLDPLSNPDA VGKTDKEHEL
481  LNA.
```

FIG. 2a.

```
 -499  GGCACGAGCT CCGATCTCCG CTGAGAGGCT CCTGGGGGCC GGGGCTCCGA GGAAAATGGT
 -439  TCGATGTTAT TAAAAATGAA TCTTAAGAAG AAAAATGAAT CACAGCAGTT AAACTATGGA
 -379  GTTCTGCTAC TTGTAAGAAG TGGAGAAGCC TGAGATTACA TCACTGACCC TTGATCCTCC
 -319  ACTGAGCTAA ACACCAGCT GGTAATTGCC TATGATTTTA TAGACTTCCC TCCATCTGCT
 -259  GGGTCCAAGT GTCCGTCTGA CTGCTCTGGT ACCGGAGCAT CTTTATTTCT GCATCTAAAC
 -199  TTGTAAAAAG CACATCGAAT CTTGTTCCCC AGGAGAAAAT CTTCAATGTA ACCATTTCA
 -139  ATGTATCCGA TGATACAAGC GCATTGTAAT CTCCAGGTAG AAGCAGCTTT ATCAGTGGAA
  -79  AGGGTTTAAT AGAACATATC CTATCATGCT TTTTCTCTGC CCCTTCTCAA ATCATCAGCA
  -19  GTAGAAAAGA GAAGAAAAC
    1  ATGTCAGGAC ACAAATGTTA TTCCTGGGAG TTGCAGGATC GGTTTGCTCA AGATAAGTCA
   61  GTTGTCAATA AGATGCAACA GAAATATTGG GAAACGAAGC AGGCCTTTAT  CAAAGCCACA
  121  GGGAAGAAGG AAGATGAACA TGTCGTTGCT TCTGATGCAG ACCTGGATGC CAAGCTAGAG
  181  CTGTTTCATT CGATTCAGAG AACCTGTTTG GACTTGTCTA AGCAATTGT GCTCTATCAA
  241  AAGAGAATAT GTTTCTTGTC TCAAGAAGAA ATGAACTGG AAAATTTCT CCGATCCCAA
  301  GGCTTCCAGG ACAAAACCCG AGCAGGAAAA ATGATGCAAG CCACAGGAAA GGCCCTCTGC
  361  TTTTCCTCCC AGCAAAGGTT GGCCTTGAGA AACCCTTTGT GTCGATTTCA CCAAGAAGTA
  421  GAGACTTTTA GACATCGGGC CATCTCCGAT ACCTGGCTGA CAGTGAACCG CATGGAGCAG
  481  TGCCGGACAG AATATAGAGG GGCGTTATTG TGGATGAAGG ACGTGTCTCA GGAACTGGAT
  541  CCAGACCTCT ACAAGCAAAT GGAGAAGTTC AGGAAGGTAC AGACACAAGT CCGCCTCGCG
  601  AAGAAGAACT TTGACAAATT GAAGATGGAT GTGTGTCAAA AGGTGGATCT TCTTGGAGCA
  661  AGCAGATGTA ACCTCTTATC TCACATGCTA GCAACATATC AGACCACTCT GCTCCACTTT
  721  TGGGAGAAAA CTTCTCACAC CATGGCAGCC ATCCATGAGA GCTTCAAAGG CTATCAACCA
  781  TATGAATTCA CAACGTTAAA GAGCTTACAA GACCCTATGA AAAGCTAGT CGAGAAAGAA
  841  AAGAAGAAGA GCTCCCGGAG GGAAAACCGG GAGGCTGTGG CACAGGAGCC GAGGCAGTTA
  901  ATTTCATTGG AGGAAGAGAA CCAGCACAAA GAATCCTCTA CTTGCCAGAA GGAGGAGGGA
  961  AAAAGCGTTC CGTCGTCTGT AGACAAGAGT TCTGCAGATG ATGCATGCTC AGGACCCATA
 1021  GATGAACTAT TAGACGTGAA ACCTGAGGAA GCTTGCCTGG GTCCCATGGC AGGGACCCCA
 1081  GAACCTGAAA GTGGGGACAA GGACGACCTC CTGCTGTTGA ACGAGATCTT CAGCACTTCC
 1141  AGCCTGGATG AAGGGGAGTT CAGCAGGGAG TGGGCTGCGG TGTTCGGAGA CGACCGGCTG
 1201  AAGGAACCAG CCCCCATGGG GGCCCAGGGA GAGCCAGACC CCAAGCCCCA GATAGGCTCT
 1261  GCGTTCCTTC CTTCACAGCT TTTAGACCAA AACATGAAAG ATCTCCAGGC CTCTCTCCAA
 1321  GAGCCTGCCA AGGCTGCCTC GGACCTGACT GCCTGGTTCA GCCTCTTTGC TGACCTCGAC
```

FIG. 2b.

```
1381  CCCCTATCAA ATCCTGATGC TATTGGGAAA ACCGATAAAG AACACGAATT GCTCAATGCA
1441  TGAGTCTGCA ACCTTCAACA GGGGAGCCCT CCGGCCACTC CGCAACACCT CATCCAGGGC
1501  TTGCAGAAGT CTAACGTGCT CAGTACGCTG TTTTAATATT TACATGCCAT TTTAATAAAA
1561  CGAGAGGGTC AAGGCCCTGT TCTATCGCT ATAAAAAAAA AAAAAAA
```

FIG. 2c.

```
  1  MSGHKCYSWE LQDRFAQDKS VVNKMQQKYW ETKQAFIKAT GKKEDEHVVA SDADLDAKLE
 61  LFHSIQRTCL DLSKAIVLYQ KRICFLSQEE NELGKFLRSQ GFQDKTRAGK MMQATGKALC
121  FSSQQRLALR NPLCRFHQEV ETFRHRAISD TWLTVNRMEQ CRTEYRGALL WMKDVSQELD
181  PDLYKQMEKF RKVQTQVRLA KKNFDKLKMD VCQKVDLLGA SRCNLLSHML ATYQTTLLHF
241  WEKTSHTMAA IHESFKGYQP YEFTTLKSLQ DPMKKLVEKE KKKSSRRENR EAVAQEPRQL
301  ISLEEENQHK ESSTCQKEEG KSVPSSVDKS SADDACSGPI DELLDVKPEE ACLGPMAGTP
361  EPESGDKDDL LLLNEIFSTS SLDEGEFSRE WAAVFGDDRL KEPAPMGAQG EPDPKPQIGS
421  AFLPSQLLDQ NMKDLQASLQ EPAKAASDLT AWFSLFADLD PLSNPDAIGK TDKEHELLNA
```

FIG. 3a.

```
  18  CAGTTATTCC TGGGAGTTGC AGGACCGGTT TGCTCAACAT AAGTCAGTTG TCAATAAGAT
  78  GCAGCAGAAA TATTGGGAGA CCAAGCAGGC CTTTATCAAA GCCACGGGGA AGAAGGAAGA
 138  TGAACATGTG GTTGCTTCTG ATGCAGACCT GGATGCCAAG CTGGAGCTGT TCACTCAAT
 198  CCAGAGAACC TGTCTGGACT TGTCTAAAGC AATCGTGCTC TATCAAAAGA GAATATGTTT
 258  CTTGTCTCAA GAGGAAAATG AACTGGGAAA GTTTCTTCGA TCTCAAGGCT TCCAAGACAA
 318  AACCCGAGCA GGAAAAATGA TGCAAGCCAC CGGCAAGGCC CTCTGCTTTT CCTCCCAGCA
 378  AAGGTTGGCC TTGAGAAACC CTTTGTGTCG ATTTCACCAA GAAGTAGAAA CTGTTAGACA
 438  TCGGGCCATC TCTGATACCT GGCTGACAGT GAACCGCATG GAGCAGTACA GGACAGAATA
 498  CAGAGGAGCG TTGTTATGGA TGAAGGACGT GTCTCAGGAA CTTGATCCAG ACCTCTACAA
 558  GCAAATGGAG AAGTTCAGGA AGGTGCAGAC ACAAGTCCGC CTTGCGAAGA AGAACTTTGA
 618  CAAGTTGAAG ATGGATGTGT GTCAAAAGGT GGATCTTCTT GGAGCAAGCA GATGTAACCT
 678  CTTATCTCAC ATGCTAGCAA CATACCAGAC CACTCTGCTC CATTTTTGGG AGAAAACTTC
 738  TCACACCATG GNAGNCATTC ATGAGAGTNT NAAAGGTTAT CAACCATATG AATTCACAAC
 798  GTTAAAGAGC TTACAAGACC CCATGAAGAA GCTAGTTGAG AAGGAAGGGA AGAAGACCTC
 858  CTCGAGGGAA AACCGGGAGG CTGTGGCACC AGAGCCGAGG CAGTTAATTT CTTTGGAGGA
 918  TGAGAACCAG CACAAAGATT CATCTACTTA TAAGACTGAG GAGGGACAAA GCGTTTTGTC
 978  TTCCGTAGAC AAAGGTTCTG TACATGACAC ATGCTCAGGA CCCATAGATG AACTATTAGA
1038  CGGGAAACCC GAGGAAGCGT GCCTGGGTCC CATGGCAGGG ACCCCAGAAC CTGAAAGTGG
1098  GGACAAGGAT GACCTCTTGC TGTTGAATGA GATCTTCACT TCCAGCCTGG AAGAAGGGGA
1158  GTTCAGCAGA GAGTGGGCTG CAGTGTTTGG AGATGACCGG CTAAAGGAGC CAGCCCCCAT
1218  GGGGGCCCAA GGAGAGCCAG ACCCCAAGCC CCAGATAGGC TCCGGATTCC TTCCGTCGCA
1278  GCTTTTAGAC CAAAATATGA AAGATCTCCA GGCCTCTCTG CAAGAGCCTG CCAAGGCTGC
1338  CTCGGACCTG  ACTGCCTGGT TCAGCCTCTT TGCTGACCTC GACCCCTTAT CAAACCCTGA
1398  TGCTGTTGGG
```

FIG. 3b.

```
  7   SYSWELQDRF AQHKSVVNKM QQKYWETKQA FIKATGKKED EHVVASDADL DAKLELFHSI
 67   QRTCLDLSKA IVLYQKRICF LSQEENELGK FLRSQGFQDK TRAGKMMQAT GKALCFSSQQ
127   RLALRNPLCR FHQEVETVRH RAISDTWLTV NRMEQYRTEY RGALLWMKDV SQELDPDLYK
187   QMEKFRKVQT QVRLAKKNFD KLKMDVCQKV DLLGASRCNL LSHMLATYQT TLLHFWEKTS
247   HTMXXIHESX KGYQPYEFTT LKSLQDPMKK LVEKEGKKTS SRENREAVAP EPRQLISLED
307   ENQHKDSSTY KTEEGQSVLS SVDKGSVHDT CSGPIDELLD GKPEEACLGP MAGTPEPESG
367   DKDDLLLLNE IFTSSLEEGE FSREWAAVFG DDRLKEPAPM GAQGEPDPKP QIGSGFLPSQ
427   LLDQNMKDLQ ASLQEPAKAA SDLTAWFSLF ADLDPLSNPD AVG
```

FIGURE 4

```
IS4    201  GAGAACCTGT CTGGACTTAT CGAAAGCAAT TGTACTCTAT CAAAAGAGGA

TATGTTCATT TTAGGAGGCC AAGGCAGGAG GATCACTTGG AGCCAGGAGT    300

IS10   201  ---------- ---------- ---------- ---------- ----------

------**** ********** ********** ********** **********    300

IS4    301  TTGAGACCAG CCTGGGCAAC AAAGTGAGAC CCCCATCTCT ACAAAAAATA

AAAACACTTA AAAATTATCC GGGTACCGTG CATGTGCAGT CCCAGCTACT    400

IS10        ********** ********** ********** ********** **********

********** ********** ********** ********** **********

IS4    401  CAGGAGGCTG AGGCAGGAGG ATCACAGTGA CCTATAATGA GCCGTTGTGC

TCCAGCCTGG GCGACAGAAG TCTTGTCTCA AGAAGAAAAC GAACTGGGAA    500

MSGHKCSYPW DLQDRYAQDK SVVNKMQQKY WETKQAFIKA TGKKEDEHVV ASDADLDAKL ELFHSIQRTC
LDLSKAIVLY QKRICFLSQE ENELGKFLRS QGFQDKTRAG KMMQATGKAL CFSSQQRLAL RNPLCRFHQE
VETFRHRAIS DTWLTVNRME QCRTEYRGAL LWMKDVSQEL DPDLYKQMEK FRKVQTQVRL AKKNFDKLKM
DVCQKVDLLG ASRCNLLSHM LATYQTTLLH FWEKTSHTMA AIHESFKGYQ PYEFTTLKSL QDPMKKLVEK
EEKKKINQQE STDAAVQEPS QLISLEEENQ RKESSSFKTE DGKSILSALD KGSTHTACSG PIDELLDMKS
EEGACLGPVA GTPEPEGADK DDLLLLSEIF NASSLEEGEF SKEWAAVFGD GQVKEPVPTM ALGEPDPKAQ
TGSGFLPSQL LDQNMKDLQA SLQEPAKAAS DLTAWFSLFA DLDPLSNPDA VGKTDKEHEL LNA.

FIGURE 16B

MSGHKCSYPW DLQDRYAQDK SVVNKMQQKY WETKQAFIKA TGKKEDEHVV ASDADLDAKL ELFHSIQRTC
LDLSKAIVLY QKRICSF.

FIGURE 17A1

GAGAGAGAGC TCGTGCCGAA TTCGGCACGA GCTCCGCCGG
GAACCTCCTG GGGGCCGGAG CACCAAGGTT
TAATATAACT TATCCTCTCA TGATTTTTTC CTGCCCCTTC
TCAAATCATC GGCAATAGAA AAGAGAAGAA
AACATGTCAG GACACAAATG TTATTCCTGG GAGTTGCAGG
ACCGGTTTGC TCAAGATAAG TCAGTTGTCA
ATAAGATGCA GCAGAAATAT TGGGAGACCA AGCAGGCCTT
TATCAAAGCC ACGGGAAGA AGGAAGATGA
ACATGTGGTT GCTTCTGATG CAGACCTGGA TGCCAAGCTG
GAGCTGTTTC ACTCAATCCA GAGAACCTGT
CTGGACTTGT CTAAAGCAAT CGTGCTCTAT CAAAAGAGAA
TATGTTTCTT GTCTCAAGAG GAAAATGAAC
TGGGAAAGTT TCTTCGATCT CAAGGCTTCC AAGACAAAAC
CCGAGCAGGA AAAATGATGC AAGCCACGGG
CAAGGCCCTC TGCTTTTCCT CCCAGCAAAG GTTGGCCTTG
AGAAACCCTT TGTGTCGATT TCACCAAGAA
GTAGAAACTT TTAGACATCG GCCATCTCT GATACCTGGC
TGACAGTGAA CCGCATGGAG CAGTACAGGA
CAGAATACAG AGGAGCGTTG TTATGGATGA AGGACGTGTC
TCAGGAACTT GATCCAGACC TCTACAAGCA
AATGGAGAAG TTCAGGAAGG TGCAGACACA AGTCCGCCTT
GCGAAAAAAA ACTTTGACAA GTTGAAGATG
GATGTGTGTC AAAAGGTGGA TCTTCTTGGA GCAAGCAGAT
GTAACCTCTT ATCTCACATG CTAGCAACAT
ACCAGACCAC TCTGCTCCAC TTTTGGGAGA AAACTTCTCA
CACCATGGCA GCCATTCATG AGAGCTTCAA
AGGTTATCAA CCATATGAAT TCACAACGTT AAAGAGCTTA
CAAGACCCCA TGAAGAAGCT AGTTGAGAAG
GAAGGGAAGA AGACCTCCTG GAGGGAAAAC CGGGAGGCTG
TGGCACCAGA GCCGAGGCAG TTAATTTCTT
TGGAGGATGA GCACAAAGAT TCATCTACTT ATAAGACTGA
AGAGGGAACA AGCGTTTTGT CTTCCGTAGA
CAAAGGTTCT GTACATGACA CATGCTCAGG ACCCATAGAT
GAACTATTAG ACGGGAAACC CGAGGAAGCG
TGCCTGGGTC CCACGGCAGG GACCCCAGAA CCTGAAAGTG

FIGURE 17A2

```
GGGACAAGGA TGACCTCTTG CTGTTGAATG
AGATCTTCAG CACTTCCTGC CTGGATGAGG GAGAGTTCAG
CAGAGAGTGG GCTGCAGTGT TTGGAGATGA
CCGGCTAAAG GAGCCAGCAC CCATGGGGGC CCAAGGAGAG
CCAGACCCCA AGCCCAGAT AGGCTCCGGA
TTCCTTCCGT CGCAGCTTTT AGACCAAAAT ATGAAAGATC
TCCAGGCCTC TCTGCAAGAG CCTGCCAAGG
CTGCCTCGGA CCTGACTGCC TGGTTCAGCC TCTTTGCTGA
CCTCGACCCC TTATCAAACC CTGATGCTGT
TGGGAAAACT GATAAAGAAC ACGAATTGCT CAATGCATGA
GTCTGCAACC TTCAACAGGG AGCCCTCGGG
CCACTCCGCG GCACCTCATC CAGGGCTTGC AGAAGTCTAA
TATGCTCGGT GTGCTGTTTT AATATTTACA
TGCCATTTTA ATAAAATGAG AGGGTCAAGG CCCTGTTTCT
ATCGCTATAA AAAAAAAA
```

FIGURE 17B1

GAGAGAGCTC GTGCCGAATT CGGCACGAGT AGAAAAGAGA
AGAAAACATG TCAGGACACA AATGTTATTC
CTGGGAGTTG CAGGACCGGT TTGCTCAAGA TAAGTCAGTT
GTCAATAAGA TGCAGCAGAA ATATTGGGAG
ACCAAGCAGG CCTTTATCAA AGCCACGGGG AAGAAGGAAG
ATGAACATGT GGTTGCTTCT GATGCAGACC
TGGATGCCAA GCTGGAGCTG TTTCACTCAA TCCAGAGAAC
CTGTCTGGAC TTGTCTAAAG CAATCGTGCT
CTATCAAAAG AGAATATGTT TCTTGTCTCA AGAGGAAAAT
GAACTGGGAA AGTTTCTTCG ATCTCAAGGC
TTCCAAGACA AAACCCGAGC AGGAAAAATG ATGCAAGCCA
CGGGCAAGGC CCTCTGCTTT TCCTCCCAGC
AAAGGTTGGC CTTGAGAAAC CCTTTGTGTC GATTTCACCA
AGAAGTAGAA ACTTTTAGAC ATCGGGCCAT
CTCTGATACC TGGCTGACAG TGAACCGCAT GGAGCAGTAC
AGGACAGAAT ACAGAGGAGC GTTGTTATGG
ATGAAGGACG TGTCTCAGGA ACTTGATCCA GACCTCTACA
AGCAAATGGA GAAGTTCAGG AAGGTGCAGA
CACAAGTCCG CCTTGCGAAA AAAAACTTTG ACAAGTTGAA
GATGGATGTG TGTCAAAAGG TGGATCTTCT
TGGAGCAAGC AGATGTAACC TCTTATCTCA CATGCTAGCA
ACATACCAGA CCACTCTGCT CCACTTTTGG
GAGAAAACTT CTCACACCAT GGCAGCCATT CATGAGAGCT
TCAAAGGTTA TCAACCATAT GAATTCACAA
CGTTAAAGAG CTTACAAGAC CCCATGAAGA AGCTAGTTGA
GAAGGAAGGG AAGAAGACCT CCTGGAGGGA
AAACCGGGAG GCTGTGGCAC CAGAGCCGAG GCAGTTAATT
TCTTTGGAGG ATGAGCACAA AGATTCATCT
ACTTATAAGA CTGAGGAGGG AACAAGCGTT TTGTCTTCCG
TAGACAAAGG TTCTGTACAT GACACATGCT
CAGGACCCAT AGATGAACTA TTAGACGGGA AACCCGAGGA
AGCGTGCCTG GGTCCCACGG CAGGGACCCC
AGAACCTGAA AGTGGGGACA AGGATGACCT CTTGCTGTTG
AATGAGATCT TCAGCACTTC CTGCCTGGAT
GAGGGAGAGT TCAGCAGAGA GTGGGCTGCA GTGTTTGGAG
ATGACCGGCT AAAGGAGCCA GCACCCATGG
GGGCCCAAGG AGAGCCAGAC CCCAAGCCCC AGATAGGCTC

FIGURE 17B2

CGGATTCCTT CCGTCGCAGC TTTTAGACCA
AAATATGAAA GATCTCCAGG CCTCTCTGCA AGAGCCTGCC
AAGGCTGCCT CGGACCTGAC TGCCTGGTTC
AGCCTCTTTG CTGACCTCGA CCCCTTATCA AACCCTGATG
CTGTTGGGAA AACTGATAAA GAACACGAAT
TGCTCAATGC ATGAGTCTGC AACCTTCAAC AGGGAGCCCT
CGGGCCACTC CGCGGCACCT CATCCAGGGC
TTGCAGAAGT CTAATATGCT CGGTGTGCTG TTTTAATATT
TACATGCCAT TTTAATAAAA TGAGAGGGTC
AAGGCCCTGT TTCTATCGCT ATAAAAAAAA AA

FIGURE 17C1

```
GGAACGAGAG AAGAAAACAT GTCAGGACAC AAATGTTATT
CCTGGGAGTT GCAGGACCGG TTTGCTCAAG
ATAAGTCAGT TGTCAATAAG ATGCAGCAGA AATATTGGGA
GACCAAGCAG GCCTTTATCA AAGCCACGGG
GAAGAAGGAA GATGAACATG TGGTTGCTTC TGATGCAGAC
CTGGATGCCA AGCTGGAGCT GTTTCACTCA
ATCCAGAGAA CCTGTCTGGA CTTGTCTAAA GCAATCGTGC
TCTATCAAAA GAGAATATGT TTCTTGTCTC
AAGAGGAAAA TGAACTGGGA AAGTTTCTTC GATCTCAAGG
CTTCCAAGAC AAAACCCGAG CAGGAAAAAT
GATGCAAGCC ACGGGCAAGG CCCTCTGCTT TTCCTCCCAG
CAAAGGTTGG CCTTGAGAAA CCCTTTGTGT
CGATTTCACC AAGAAGTAGA AACTTTTAGA CATCGGGCCA
TCTCTGATAC CTGGCTGACA GTGAACCGCA
TGGAGCAGTA CAGGACAGAA TACAGAGGAG CGTTGTTATG
GATGAAGGAC GTGTCTCAGG AACTTGATCC
AGACCTCTAC AAGCAAATGG AGAAGTTCAG GAAGGTGCAG
ACACAAGTCC GCCTTGCGAA AAAAAACTTT
GACAAGTTGA AGATGGATGT GTGTCAAAAG GTGGATCTTC
TTGGAGCAAG CAGATGTAAC CTCTTATCTC
ACATGCTAGC AACATACCAG ACCACTCTGC TCCACTTTTG
GGAGAAAACT TCTCACACCA TGGCAGCCAT
TCATGAGAGC TTCAAAGGTT ATCAACCATA TGAATTCACA
ACGTTAAAGA GCTTACAAGA CCCCATGAAG
AAGCTAGTTG AGAAGGAAGG GAAGAAGACC TCCTGGAGGG
AAAACCGGGA GGCTGTGGCA CCAGAGCCGA
GGCAGTTAAT TTCTTTGGAG GATGAGCACA AAGATTCATC
TACTTATAAG AGACCCATAG ATGAACTATT
AGACGGGAAA CCCGAGGAAG CGTGCCTGGG TCCCACGGCA
GGGACCCCAG AACCTGAAAG TGGGGACAAG
GATGACCTCT TGCTGTTGAA TGAGATCTTC AGCACTTCCT
GCCTGGATGA GGGAGAGTTC AGCAGAGAGT
GGGCTGCAGT GTTTGGAGAT GACCGGCTAA AGGAGCCAGC
ACCCATGGGG GCCCAAGGAG AGCCAGACCC
CAAGCCCCAG ATAGGCTCCG GATTCCTTCC GTCGCAGCTT
TTAGACCAAA ATATGAAAGA TCTCCAGGCC
TCTCTGCAAG AGCCTGCCAA GGCTGCCTCG GACCTGACTG
```

FIGURE 17C2

CCTGGTTCAG CCTCTTTGCT GACCTCGACC
CCTTATCAAA CCCTGATGCT GTTGGGAAAA CTGATAAAGA
ACACGAATTG CTCAATGCAT GAGTCTGCAA
CCTTCAACAG GGAGCCCTCG GGCCACTCCG CGGCACCTCA
TCCAGGGCTT GCAGAAGTCT AATATGCTCG
GTGTGCTGTT TTAATATTTA CATGCCATTT TAATAAAATG
AGAGGGTCAA GGCCCTGTTT CTATCGCTAT
AAAAAAAAAA

FIGURE 18A

```
MSGHKCYSWE LQDRFAQDKS VVNKMQQKYW ETKQAFIKAT GKKEDEHVVA SDADLDAKLE LFHSIQRTCL
DLSKAIVLYQ KRICFLSQEE NELGKFLRSQ GFQDKTRAGK MMQATGKALC FSSQQRLALR NPLCRFHQEV
ETFRHRAISD TWLTVNRMEQ YRTEYRGALL WMKDVSQELD PDLYKQMEKF RKVQTQVRLA KKNFDKLKMD
VCQKVDLLGA SRCNLLSHML ATYQTTLLHF WEKTSHTMAA IHESFKGYQP YEFTTLKSLQ DPMKKLVEKE
GKKTSWRENR EAVAPEPRQL ISLEDEHKDS STYKTEEGTS VLSSVDKGSV HDTCSGPIDE LLDGKPEEAC
LGPTAGTPEP ESGDKDDLLL LNEIFSTSCL DEGEFSREWA AVFGDDRLKE PAPMGAQGEP DPKPQIGSGF
LPSQLLDQNM KDLQASLQEP AKAASDLTAW FSLFADLDPL SNPDAVGKTD KEHELLNA.
```

FIGURE 18B

MSGHKCYSWE LQDRFAQDKS VVNKMQQKYW ETKQAFIKAT GKKEDEHVVA SDADLDAKLE LFHSIQRTCL
DLSKAIVLYQ KRICFLSQEE NELGKFLRSQ GFQDKTRAGK MMQATGKALC FSSQQRLALR NPLCRFHQEV
ETFRHRAISD TWLTVNRMEQ YRTEYRGALL WMKDVSQELD PDLYKQMEKF RKVQTQVRLA KKNFDKLKMD
VCQKVDLLGA SRCNLLSHML ATYQTTLLHF WEKTSHTMAA IHESFKGYQP YEFTTLKSLQ DPMKKLVEKE
GKKTSWRENR EAVAPEPRQL ISLEDEHKDS STYKRPIDEL LDGKPEEACL GPTAGTPEPE SGDKDDLLLL
NEIFSTSCLD EGEFSREWAA VFGDDRLKEP APMGAQGEPD PKPQIGSGFL PSQLLDQNMK DLQASLQEPA
KAASDLTAWF SLFADLDPLS NPDAVGKTDK EHELLNA.

FIGURE 18C

MSGHKCYSWE LQDRFAQDKS VVNKMQQKYW ETKQAFIKAT GKKEDEHVVA SDADLDAKLE LFHSIQRTCL
DLSKAIVLYQ KRICFLSQEE NELGKFLRSQ GFQDKTRAGK MMQATGKALC FSSQQRLALR NPLCRFHQEV
ETFRHRAISD TWLTVNRMEQ YRTEYRGALL WMKDVSQELD PDLYKQMEKF RKVQTQVRLA KKNFDKLKMD
VCQKVDLLGA SRCNLLSHML ATYQTTLLHF WEKTSHTMAA IHESFKGYQP YEFTTLKSLQ DPMKKLVEKE
GKKTSWRENR EAVAPEPRQL ISLEDEHKDS STYKTEEGTS VLSSVDKGSV HDTCSGPIDE LLDGKPEEAC
LGPTAGTPEP ESGDKDDLLL LNEIFSTSCL DEGEFSREWA AVFGDDDRLKE PAPMGAQGEP DPKPQIGSGF
LPSQLLDQNM KDLQASLQEP AKAASDLTAW FSLFADLDPL SNPDAVGKTD KEHELLNA.

FIG. 19A

```
IS10   1    MSGHKCSYPW DLQDRYAQDK SYVWKHQQKY WETKQ AFIKA TGKKEDE HVV ASDADLDAKL ELFHSIQRTC LDLSKAIVLY QKRICFLSQE ENELGKFLRS  100
ref. 10 1   ---------- ---------- ---------- -----      ----- ------- --- ---------- ---------- ---------- -----G---- ----------  100
                                                        Tep69
mB9    1    ------*S-  El-drF---- ----v--q-- --t--      ----- ---t--- -v- a-da---- l -h-i---- -ls-iv---- ---r------ -e--n--k--s  99
mB10   1    ------*S-  El-drF---- ----v--q-- --t--      ----- ---t--- -v- a-da---- l -h-i---- -ls-iv---- ---r------ -e--n--k--s  99
mB2A   1    ------*S-  El-drF---- ----v--q-- --t--      ----- ---t--- -v- a-da---- l -h-i---- -ls-iv---- ---r------ -e--n--k--s  99

IS10   101  QGFQDKTRAG KWWQATGKAL CFSSQQRLAL RWPLCRFHQE VETFRHRAIS DTWLTVNRME QCRTEYRGAL LWWKDVSQEL DPDLYKQMEK FRKVQTQVRL  200
IS4         ---------- ---------- ---------- ---------- ---------- ---------- ---------- ---------- ---------- ----------  200
mB9    100  -g-d-r-  k--atg----   ---s------ ]  rnp----- ------    ve--r---- -t--t---e -Y-t-y-al  ------    -e-------- ----vq--v- 199
mB10   100  -g-d-r-  k--atg----   ---s------ ]  rnp----- ------    ve--r---- -t--t---e -Y-t-y-al  ------    -e-------- ----vq--v- 199
mB2A   100  -g-d-r-  k--atg----   ---s------ ]  rnp----- ------    ve--r---- -t--t---e -Y-t-y-al  ------    -e-------- ----vq--v- 199
```

FIG. 19B

```
IS10   201  AKKNFDKLKM DVCQKYDLLG ASRQHLLSHM LATYQTTLLH FWEKTSHTMA AIHESFKGYQ PYEFTTLKSL QDPMKKLVEK EEKKKINQQE STDA*AVQEP  299
IS4                ---------- ---------- ---------- ---------- ---------- ---------- ---------- ---------- ----------    ....*.....  299
mB9    200  a----- --k--- -v--k----- ---------- a--cn-]--- ------ftt- ---------- --p-kkl--k -G--TSWR*- NREaV-p*--  297
mB10   200  a----- --k--- -v--k----- ---------- a--cn-]--- ------ftt- ---------- --p-kkl--k -G--TSWR*- NREaV-p*--  297
mB2A   200  a----- --k--- -v--k----- ---------- a--cn-]--- ------ftt- ---------- --p-kkl--k -G--TSWR*- NREaV-p*--  297

IS10   300  SQLISLEEEN QRKESSSFKT EDGKSILSAL DKGSTH*TAC SGPIDELLDW KSEEGACLGP VAGTPEPE*G ADKDDLLLLS EIFMASSLEE GEFSKEWAAV  397
IS4              ---------- ---------- ---------- ---------- ---------- ---------- ---------- ---------- ---------- ----------   397
mB9    298  Rq--sl-DeH **kDs-TY-- -E-TsVl-SV --g-V-DT*- --------- G--P--*a--gp T--p---Sg *-k--ll--N ---ST-ClD- g---R--aa-  392
mB10   298  Rq--sl-DeH **kDs-TY-- -E-TsVl-SV --g-V-DT*- --------- G--P--*a--gp T--p---Sg *-k--ll--N ---ST-ClD- g---R--aa-  392
mB2A   298  Rq--sl-DeH **kDs-TY-R ********** ********** ********   G--P--*a--gp T--p---Sg *-k--ll--N ---ST-ClD- g---R--aa-  371
```

FIG. 19C

```
IS10   398  FGDGQVKEPV PTM*ALGEPD PKAQTGSGFL PSQLLDQNMK DLQASLQEPA KAASDLTAWF SLFADLDPLS NPDAVGKTDK EHELLNA   484
IS4    398  ---------- ---------- ---------- ---------- ---------- ---------- ---------- ---------- -------   484
mB9    393  --dDRL---A -*-G-Q---- --p-l-sg-- ps-------- dl--sl-e-a -----s---- --f----pl- n------t- -------   479
mB10   393  --dDRL---A -*-G-Q---- --p-l-sg-- ps-------- dl--sl-e-a -----s---- --f----pl- n------t- -------   479
mB2A   393  --dDRL---A -*-G-Q---- --p-l-sg-- ps-------- dl--sl-e-a -----s---- --f----pl- n------t- -------   458
```

FIG. 21A

*absent
-identity

IS10 human islet
IS4 human islet

```
IS10  ********** ********** ********** ********** ********** **********
IS4   ********** ********** ********** ********** ********** **********
                                                              START

E IS10 ********** ********** ******-CTG CAGGAAGCAG CAGGAGACGC CCGGCAGCCG GGACGGTCGG GGA-GC-T-A ----*GA---  ------ATG  +3
  IS4  ********** **********-    A----T--- T------C- ---------- ----CCC--- ---------- ---A--A-   ----*GA---  ------ATG  +3
```

FIGURE 21D mB102A1

-47 GAGAGAGCTCGTGCCGAATTCGGCACGAGTAGAAAAGAGAAGAAAACATG  +3 mB9B3

-143
GAGAGAGAGCTC TCGTGCCGAA TTCGGCACGA GCTCCGCCGG GAACCTCCTG GGGGCCGGAG CACCAAGGTT
TAATATAAACT TATCCCTCTCA TGATTTTTTC CTGCCCCTTC TCAAATCATC GGCAATAGAA AAGAGAAGAA
AACATG +3 rat

-494
CTCCGATCTC CGCTGAGAGG CTCCTGGGGG CCGGGGCTCC GAGGAAAATG GTTCGATGTT ATTAAAAATG
AATCTTAAGA AGAAAAATGA ATCACAGCAG TTAAACTATG GAGTTCTGCT ACTTGTAAGA AGTGGAGAAG
CCTGAGATTA CATCACTGAC CCTTGATCCT CCACTGAGCT AAAACACCAG CTGGTAATTG CCTATGATTT
TATAGACTTC CCTCCATCTG CTGGGTCCAA GTGTCCGTCT GACTGCTCTG GTACCGGAGC ATCTTTATTT
CTGCATCTAA ACTTGTAAAA AGCACATCGA ATCTTGTTCC CCAGGAGAAA ATCTTCAATG TAACCATTTT
CAATGTATCC GATGATACAA ATCTCCAGGT AGAAGCAGCT TTATCAGTGG AAAGGTTTA
ATAGAACATA TCCTATCATG CTTTTTCTCT GCCCCTTCTC AATCATCAG CAGTAGAAAA GAGAAGAAAA
CATG +3

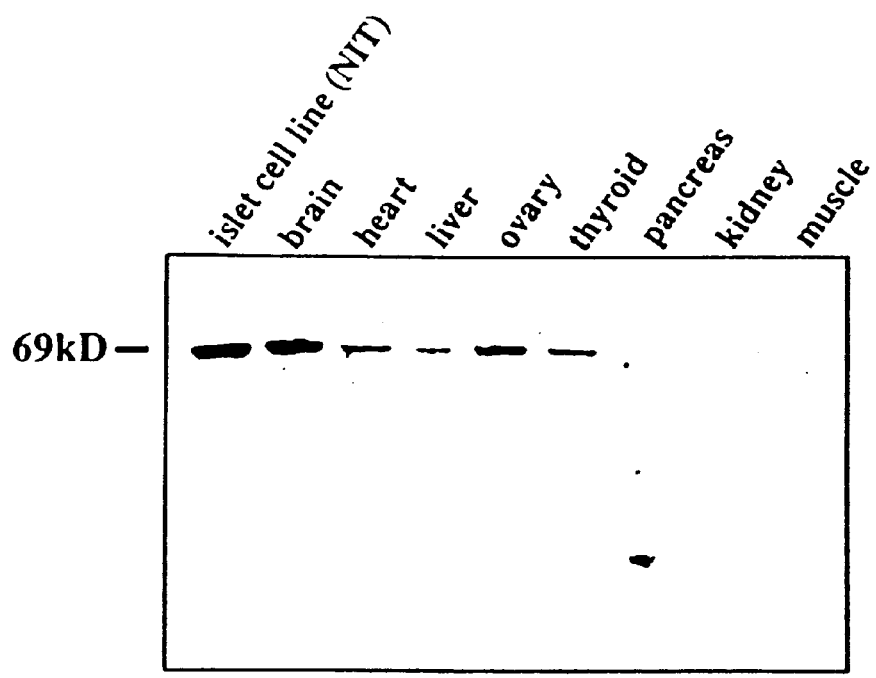
FIG 27a
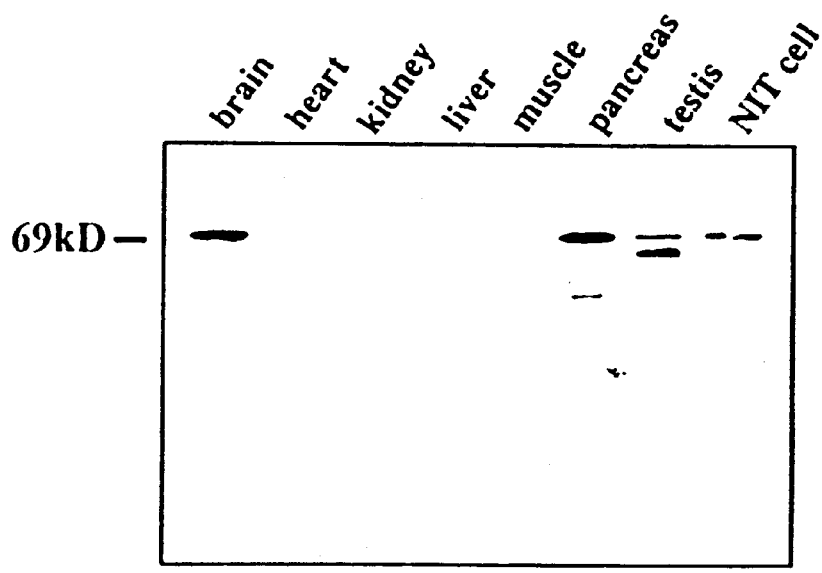
FIG 27.b.

ICAp69

ICAp69 short

…

METHODS OF CONTROLLING T LYMPHOCYTE MEDIATED IMMUNE RESPONSES

REFERENCE TO RELATED APPLICATIONS

This application is a continuation-in-part of U.S. patent application Ser. No. 08/237,363, filed May 3, 1994 and is a cip of PCT/CA00264 filed May 3, 1995.

This invention relates to methods for controlling T lymphocyte mediated immune responses. It also relates to methods and compositions for the prevention or amelioration of diabetes.

BACKGROUND OF THE INVENTION

T lymphocyte mediated immune responses are important in the development of most autoimmune diseases, including Type 1 insulin dependent diabetes mellitus (IDDM), and in transplant and tumour rejection in mammals (Slattery R M, Kjer-Nielsen L, Allison J, Charlton B, Mandel T E, Miller J F., "Prevention of diabetes in non-obese diabetic I-A$^K$ transgenic mice", Nature, (1990), vol. 345, pp. 724–6; Lund T, O'Reilly L, Hutchings P, et al., "Prevention of insulin-dependent diabetes mellitus in non-obese diabetic mice by transgenes encoding modified I-A beta-chain or normal I-E alpha-chain", Nature, (1990), vol. 345, pp. 727–9; Hutchings P R, Simpson E, O'Reilly L A, Lund T, Waldmann H, Cooke A., "The involvement of Ly2+T cells in beta cell destruction", J. Autoimmun. (1990), vol. 1, pp. 101–9).

Genetic components have been identified in several T cell mediated autoimmune diseases which heighten the risk of disease development. There is, however, strong evidence that non-genetic (environmentally acquired) agents or events also participate and trigger or sustain the autoimmune response. This has been shown, for example, in IDDM (Thorsby E, Rønningen K S, "Particular HLA-DQ molecules play a dominant role in determining susceptibility or resistance to Type 1 (insulin dependent) diabetes mellitus", Diabetologia, (1993), vol. 36, pp. 371–377).

There is at present no universally accepted model of autoimmunity, but mimicry models have received much attention. In these models, autoimmunity is perceived as an immunological cross-reaction between an auto- or self-antigen and a bona fide external antigen (Gray C, Matzinger P., "T cell memory is shortlived in the absence of antigen", J. Exp. Med. (1991), vol. 174, pp. 969–972; Beverly PCL, "Is T cell memory maintained by cross-reactive stimulation?", Immunol. Today, (1990), vol. 11, pp. 203–205). T cell sensitisation to self-antigens has been demonstrated in several diseases, including multiple sclerosis where sensitisation to myelin basic protein occurs, IDDM, ulcerative colitis, and arthritis. In IDDM, both mimicry antigen and disease-related self-antigen have been identified.

A conventional view of autoimmune diseases would suggest that administration of the autoantigen or self-antigen against which T cells are sensitised, or of analogues or fragments of the autoantigens, should cause T cell proliferation and exacerbation of the disease.

Lake et al. (Intl. Immunol. (1993), vol. 5, pp. 461–466) and Sloan-Lancaster et al. (Nature (1993), vol. 363, pp. 156–159) have reported on in vitro studies of anergy induction in activated T lymphocytes when the cells were exposed to analogues or high concentrations of an exogenous antigen or peptide to which the cells had previously been sensitised by experimental immunisation.

The present inventors are the first to demonstrate anergy induction in diabetes by a bona fide self-antigen. Using IDDM as a model, they have shown that under conditions in which the endogenous mimicry antigen has a fully stimulatory effect on activated T lymphocytes, the related autoantigen renders these cells anergic. Surprisingly, the anergenic effect was shown to be dominant, so that T lymphocyte can be rendered anergic by the self-antigen even in the presence of the fully stimulatory mimicry antigen.

The inventors have shown that development of IDDM can be prevented by treatment early in life with the self-antigen or fragments thereof. They have also demonstrated suppressed or delayed development of IDDM by immunisation with the mimicry antigen or fragments thereof.

SUMMARY OF THE INVENTION

In accordance with one embodiment of the present invention, there is provided a method for preventing the development of a T cell mediated autoimmune disease in a mammal having a population of T cells sensitised to an antigen related to said autoimmune disease comprising administering to the mammal an effective amount of a protein or peptide selected from the group consisting of (a) the antigen;

(b) an effective fragment of the antigen; and (c) an effective analogue of the antigen to prevent the expansion of the population of sensitised T cells.

In accordance with another embodiment of the present invention, there is provided a composition for preventing the development of a T cell mediated autoimmune disease in a mammal having a population of T cells sensitised to an antigen related to said autoimmune disease, said composition comprising an effective amount of a protein or peptide selected from the group consisting of (a) the antigen;

(b) an effective fragment of the antigen; and (c) an effective analogue of the antigen and a pharmaceutically acceptable carrier.

In accordance with a further embodiment of the present invention, there is provided a method for preventing the development of diabetes in a susceptible mammal comprising administering to the mammal an effective amount of a protein or peptide selected from the group consisting of (a) p69 protein;

(b) peptide AFIKATGKKEDE (SEQ ID NO 23); and (c) an analogue or fragment of (a) or (b).

In accordance with a further embodiment of the present invention, there is provided a composition for preventing the development of diabetes in a susceptible mammal comprising an effective amount of a protein or peptide selected from the group consisting of (a) p69 protein;

(b) peptide AFIKATGKKEDE; and (c) an analogue or fragment of (a) or (b) and a pharmaceutically acceptable carrier.

In accordance with a further embodiment of the present invention, there is provided a method for preventing or delaying the development of a T cell mediated autoimmune disease in a mammal having a population of T cells sensitised to an antigen related to said autoimmune disease comprising administering to the mammal an immunogenic composition comprising an effective amount of a protein or peptide selected from the group consisting of (a) the antigen;

(b) an effective fragment of the antigen; and
(c) an effective analogue of (a) or (b) and a suitable adjuvant.

In accordance with a further embodiment of the present invention, there is provided a composition for preventing or delaying the development of a T cell mediated autoimmune disease in a mammal having a population of T cells sensitised to an antigen related to said autoimmune disease, said composition comprising an effective amount of a protein or peptide selected from the group consisting of
(a) the antigen;
(b) an effective fragment of the antigen; and
(c) an effective analogue of the antigen and a suitable adjuvant.

In accordance with a further embodiment of the present invention, there is provided a method for preventing or delaying the development of diabetes in a susceptible mammal comprising administering to the mammal an immunogenic composition comprising an effective amount of a protein or peptide selected from the group consisting of
(a) the antigen;
(b) an effective fragment of the antigen; and
(c) an effective analogue of (a) or (b) and a suitable adjuvant.

In accordance with a further embodiment of the present invention, there is provided an immunogenic composition for preventing or delaying the development of diabetes in a susceptible mammal comprising an effective amount of a protein or peptide selected from the group consisting of
(a) the antigen;
(b) an effective fragment of the antigen; and
(c) an effective analogue of the antigen and a suitable adjuvant.

In accordance with a further embodiment of the present invention, there is provided an isolated nucleic acid molecule having a nucleotide sequence selected from the group consisting of
(a) the sequence set out in FIG. 1a (SEQ ID NO:1);
(b) the sequence set out in FIGS. 2a and 2b (SEQ ID NO:3);
(c) the sequence set out in FIG. 17a (SEQ ID NO:29);
(d) the sequence set out in FIG. 17b (SEQ ID NO:30);
(e) the sequence set out in FIG. 17c (SEQ ID NO:31);
(f) the sequence set out in FIG. 15 (SEQ ID NO:27);
(g) the sequence set out in FIG. 21 and designated A (SEQ ID NO:35);
(h) the sequence set out in FIG. 21 and designated B (SEQ ID NO:36);
(i) the sequence set out in FIG. 21 and designated C (SEQ ID NO:37);
(j) the sequence set out in FIG. 21 and designated D (SEQ ID NO:38);
(k) the sequence set out in FIG. 21 and designated E (SEQ ID NO:39);
(l) the sequence IS10 set out in FIGS. 19a, 19b and 19c (SEQ ID NO:43);
(m) a sequence complementary to any one of the sequences defined in (a) to (1);and
(n) a nucleotide sequence which hybridises under stringent conditions to any one of the sequences defined in (a) to (1).

In accordance with a further embodiment of the present invention, there is provided a peptide comprising an amino acid sequence selected from the group consisting of (a) EFKADEKK (SEQ ID NO:7);
(b) EFKATGKK (SEQ ID NO:22);
(c) AFIKATGKKEDE (SEQ ID NO:23);
(d) FKADEKKFWGKYLYEIAR (SEQ ID NO:11);
(e) EFKADEKKFWGKYL (SEQ ID NO:42).

SUMMARY OF THE DRAWINGS

Certain embodiments of the invention are described, reference being made to the accompanying drawings, wherein:

FIG. 1a shows the cDNA nucleotide sequence (Sequence ID No: 1) and FIG. 1b the deduced amino acid sequence (Sequence ID No: 2) of human p69 protein.

FIGS. 2a & b show the cDNA nucleotide sequence (Sequence ID No: 3) and FIG. 2c the deduced amino acid sequence (Sequence ID No: 4) of rat p69 protein.

FIG. 3 a shows the cDNA nucleotide sequence (Sequence ID No: 5) and FIG. 3b the deduced amino acid sequence (Sequence ID No: 6) of mouse p69 protein.

FIG. 4 shows a comparison of the deduced amino acid sequences of human Sequence ID NO:2, Sequence ID NO:4 rat and mouse p69 SEQ ID NO:6 proteins. Deletions are indicated by asterisks and identical nucleotides or amino acids by dashes. The human (nucleotide (Sequence ID NO:1 and amino acid sequences are shown in full and only divergent sequences are indicated by letter for rodent sequences. Open reading frames are aligned. Main motifs homologous to bovine serum albumin are boxed.

Checkerboard bars indicate the response in the presence of a mixture of the two agents shown in the adjacent two bars.

Figure 10:
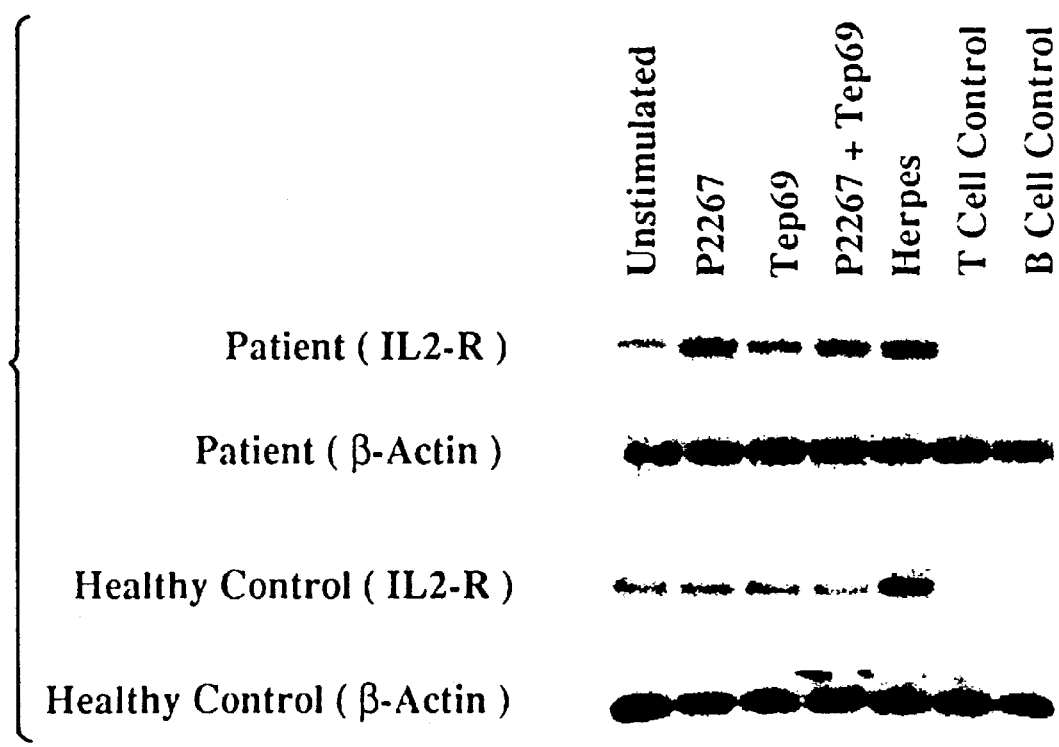

FIG. 10 shows a scan of a Southern blot of PCR-amplified IL2 receptor transcripts separated on agarose gel, blotted onto nylon filters and probed with a radiolabelled internal oligonucleotide.

Figure 11:
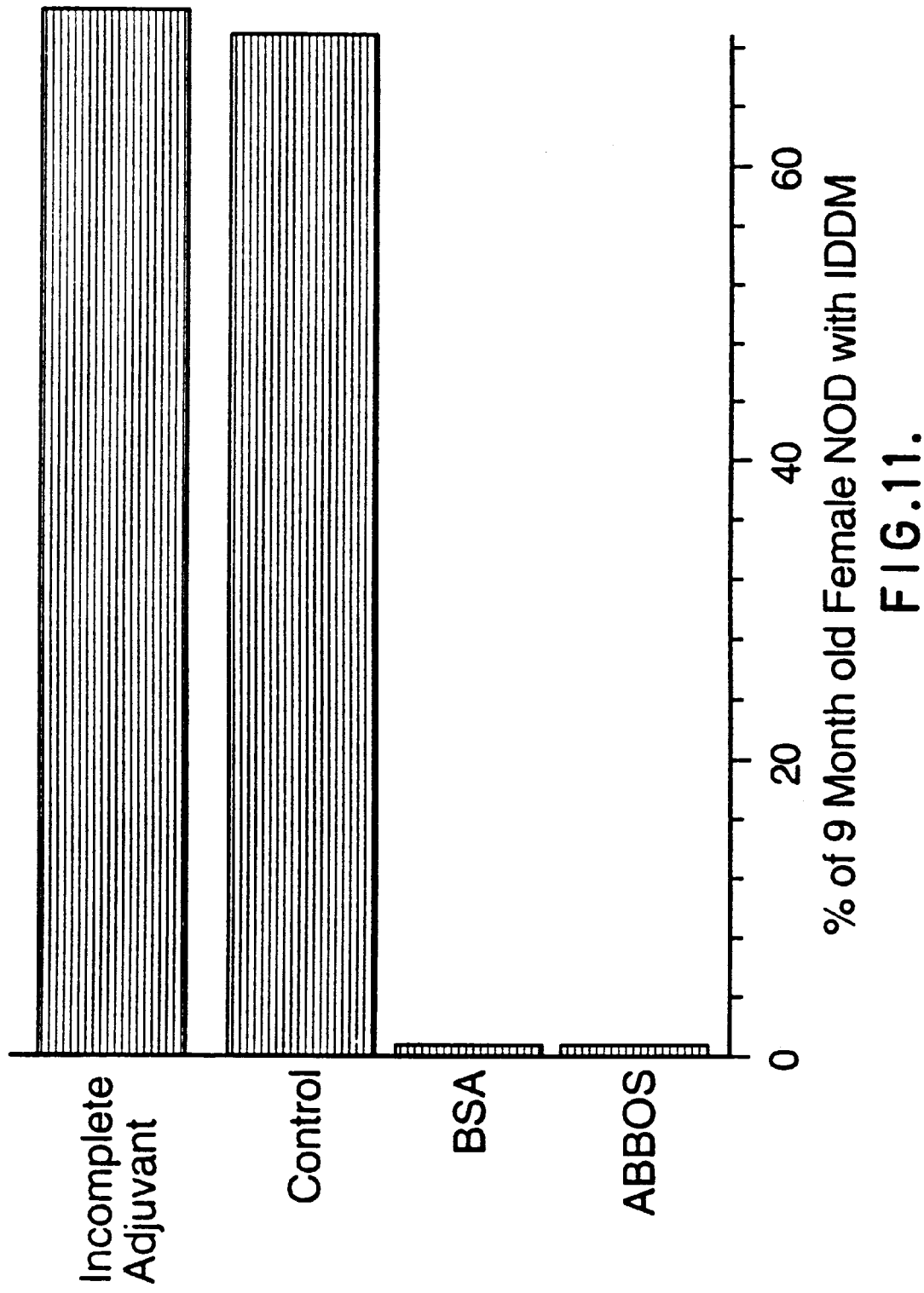

FIG. 11 shows incidence of IDDM in NOD mice at nine months of age after treatment with the indicated agents at five weeks of age.

Figure 12:
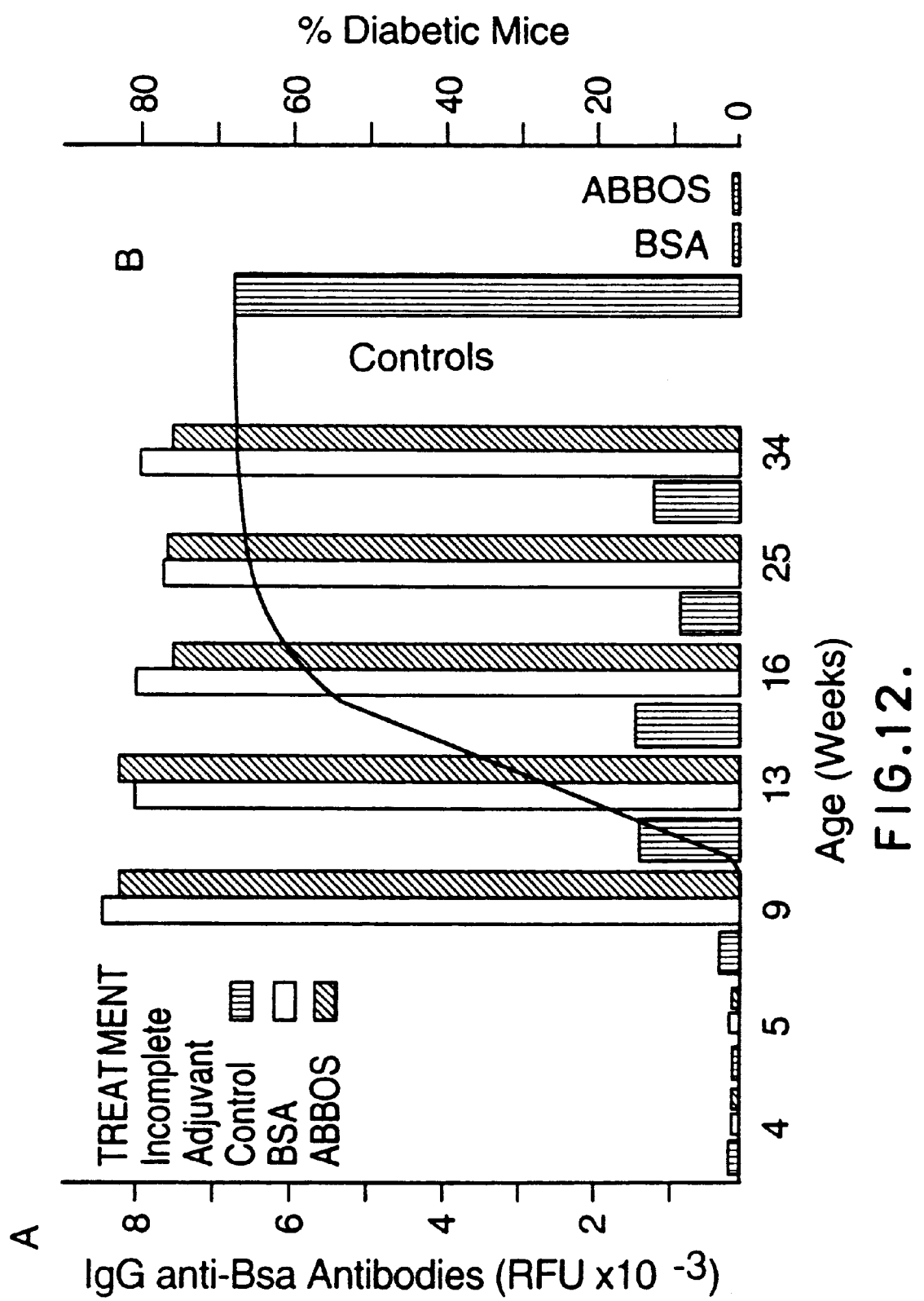

FIG. 12 shows (panel A) anti-bovine serum albumin antibody levels of NOD mice after indicated treatments at various times up to 34 weeks of age and (panel B) IDDM incidence in same mice at 34 weeks of age after indicated treatments. Curve superimposed on panel A shows increasing IDDM incidence in control group over 34 weeks from birth.

Figure 13:
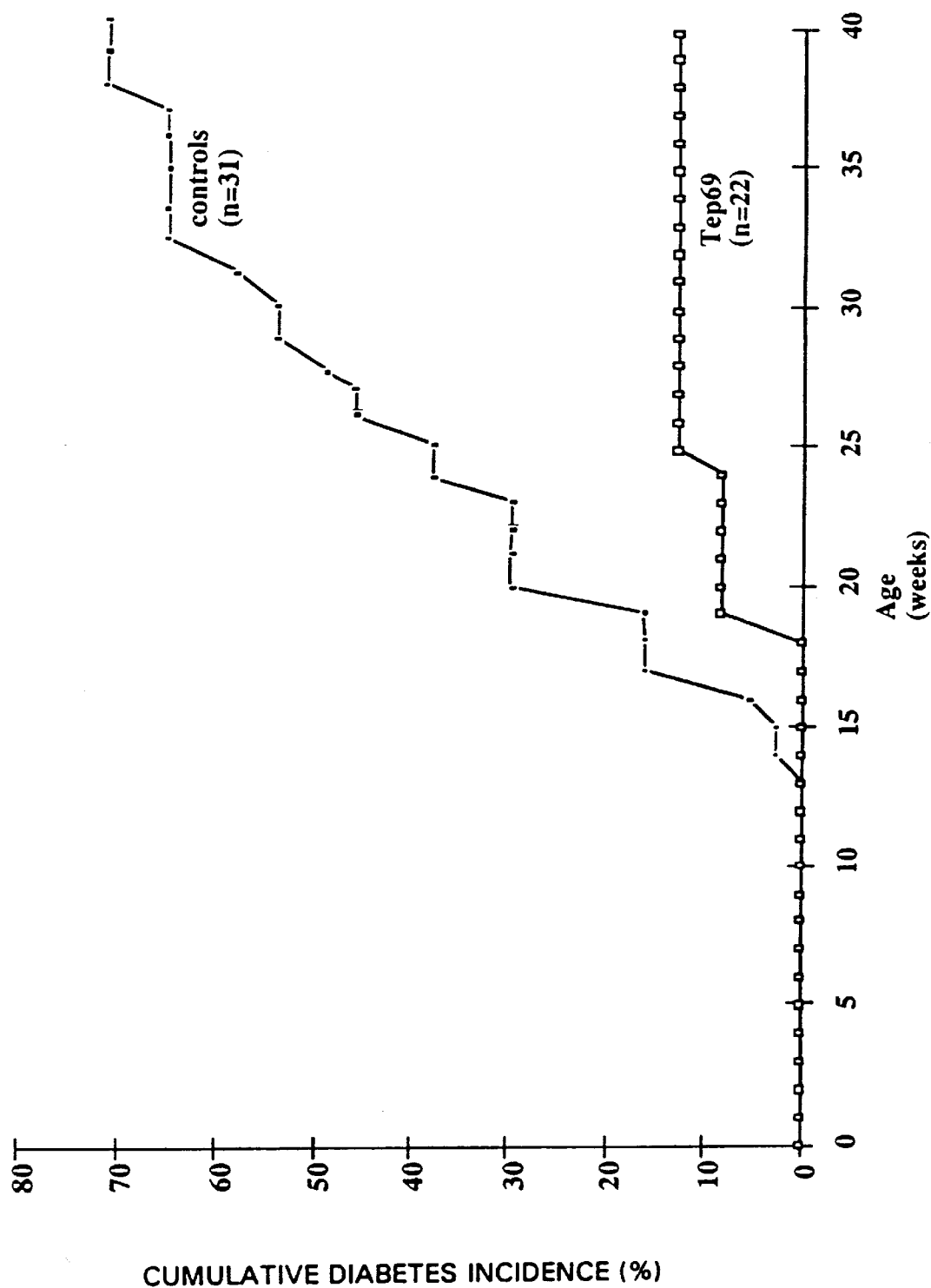

FIG. 13 shows the effect of neonatal treatment with the peptide Tep69 on development of IDDM in female NOD mice.

Figure 14:
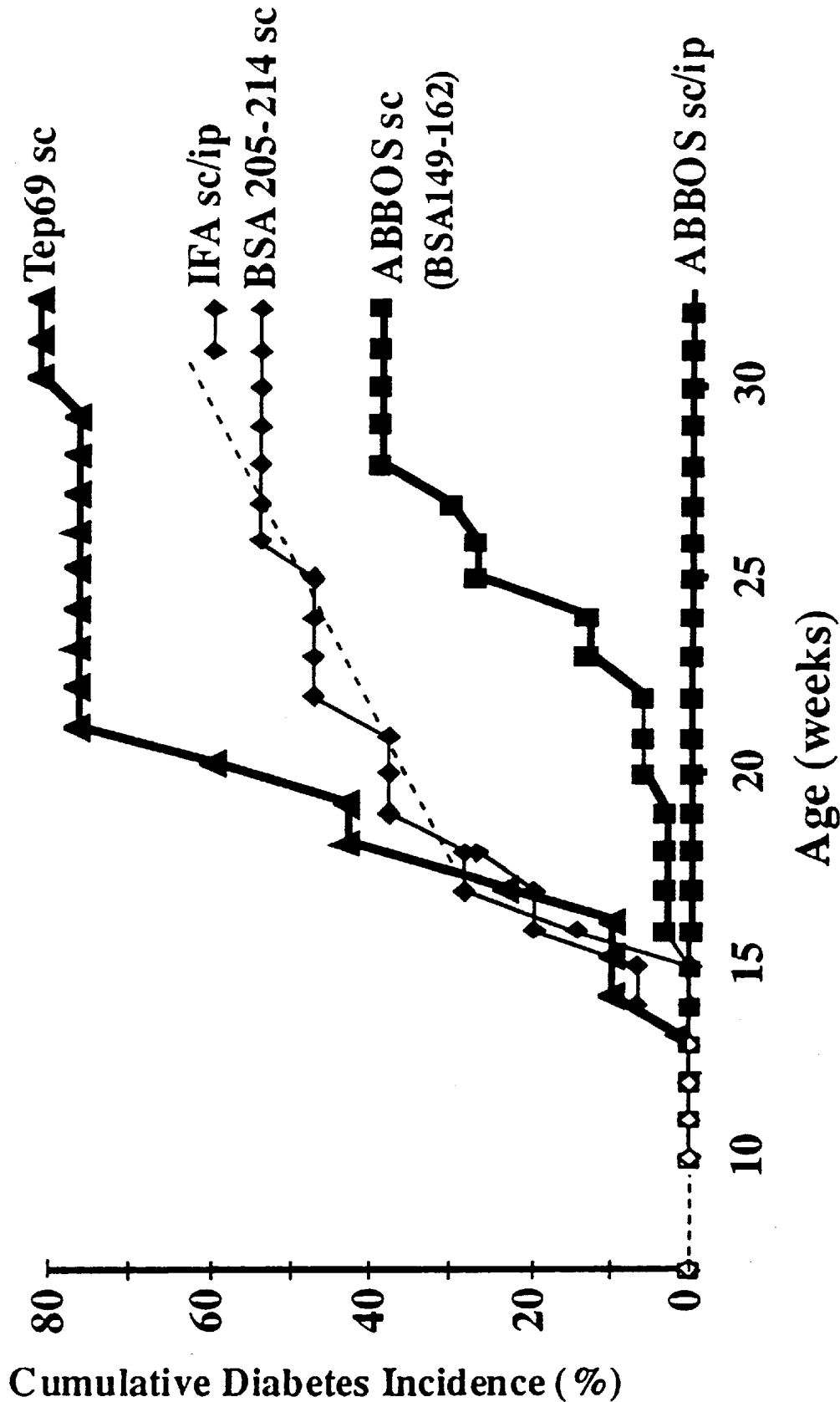

FIG. 14 shows the effect of immunising NOD mice as follows:

Tep69 sc=50 μg Tep 69 in complete Freund's adjuvant (IFA), subcutaneously

IFA sc/ip=subcutaneous IFA, followed in half of animals by intraperitoneal in complete Freund's adjuvant (data pooled)

BSA 205–214 sc=50 μg BSA peptide 205–214 in IFA subcutaneously

ABBOS sc=50 μg ABBOS in IFA subcutaneously

ABBOS sc/ip=50 μg ABBOS in IFA subcutaneously, followed by 50 μg ABBOS in IFA intraperitoneally.

FIG. 15 shows a portion of the nucleotide sequence of human p69 cDNA, clone IS4, showing additional exon 4, (Sequence ID NO 45), compared with the human clone IS10 cDNA sequence. Stop codons are boxed.

FIG. 16a shows the deduced amino acid sequence of human clone IS10 p69 (Sequence ID No.: 40).

FIG. 16b shows the deduced amino acid sequence of the truncated form of p69 encoded in IS4 (Sequence ID No.: 41).

FIGS. 17A1, 17A2, 17B1, 17B2, 17C1 and 17C2 show the nucleotide sequences of alternatively spliced mouse p69 cDNA clones.

FIGS. 17A1 & A2: clone mB9B3(Sequence ID No.: 29)
FIGS. 17B1 & B2: clone mB9B3 (Sequence ID No.: 30)
FIGS. 17C1 & C2: clone mB2A10 (Sequence ID No.: 31)

FIGS. 18a, 18b and 18c show the deduced amino acid sequences (Sequence ID Nos. 32, 33, 34, respectively), corresponding to the mouse p69 cDNA sequence of FIGS. 17a, b and c respectively.

FIGS. 19a, 19b and 19c show a comparison of the deduced amino acid sequences of human and mouse p69 cDNA clones isolated from a human islet cell library (IS4; Sequence ID NO:44: IS10; Sequence ID NO:40) or a mouse brain cDNA library mB9 : Sequence ID NO:32; mB10 : Sequence ID NO:33; mB2a : Sequences ID NO:34). The amino acid sequence of human clone IS10 is shown in full (Sequence ID NO 40). Where the other sequences correspond to IS10, identical residues are indicated by a dash. Missing residues are indicated by an asterisk. Black Bars: regions of homology with BSA; small letters: conservative base change, i.e. silent base change leading to the expression of the same amino acid; capital letters: base change leading to expression of a different amino acid.

Figure 20:
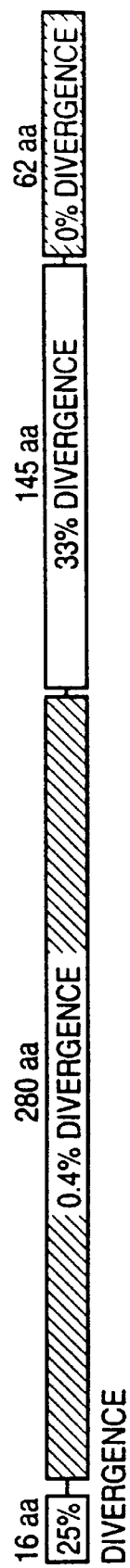

FIG. 20 shows a domain map of p69 protein.

FIGS. 21a, 21b and 21c show the nucleotide sequences of 5'-untranslated portion of p69 cDNA clones from:

human islet clone IS4 (Sequence ID No.: 38)
human islet clone IS10 (Sequence ID No. 39)

FIG. 21D shows the nucleotide sequences of 5' untranslated sequences of p69 cDNA clones from:

rat islet clone pRI c102 (Sequence ID NO: 35);
mouse brain clone mB9B3 (Sequence ID NO: 36); and
mouse brain clone mB102A1 (Sequence ID NO: 37).

Figure 22:
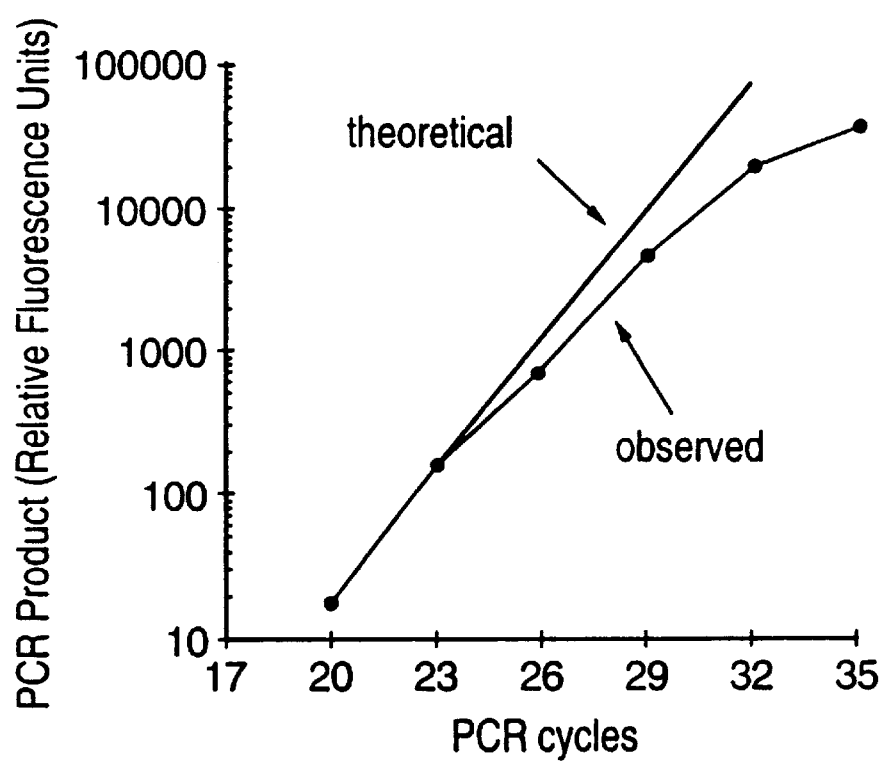

FIG. 22 shows PCR kinetics of p69 mRNA amplification. There is an exponential increment of PCR product between cycle 20 and 29 with an amplification efficiency $\geq 90\%$. A hypothetical growth curve for the PCR product (calculated for an amplification efficiency of 100%) starting from the actual quantity of molecules at 20 cycles, is included for illustration (thin line).

Figure 23C:
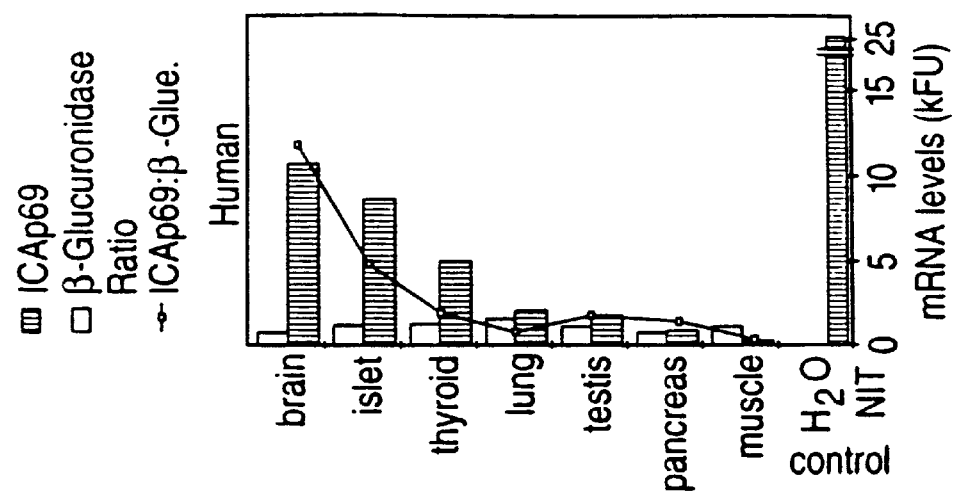
Figure 23B:
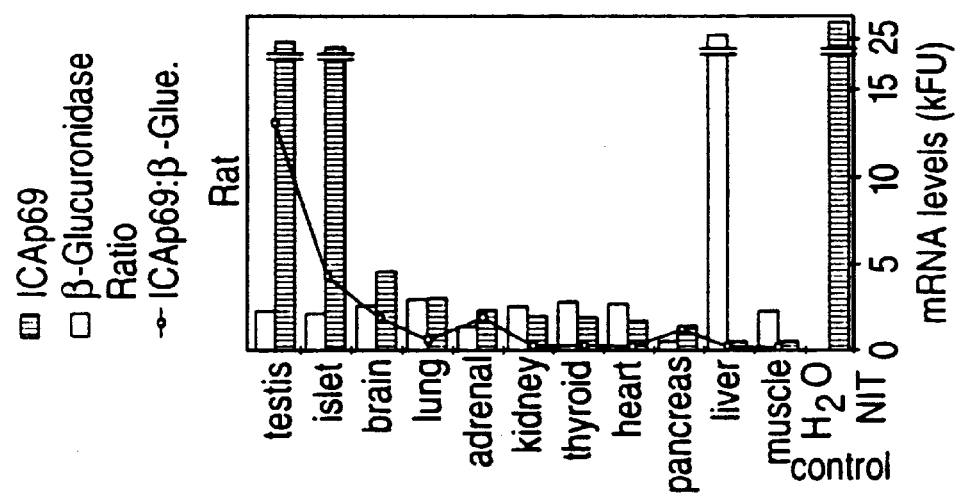
Figure 23A:
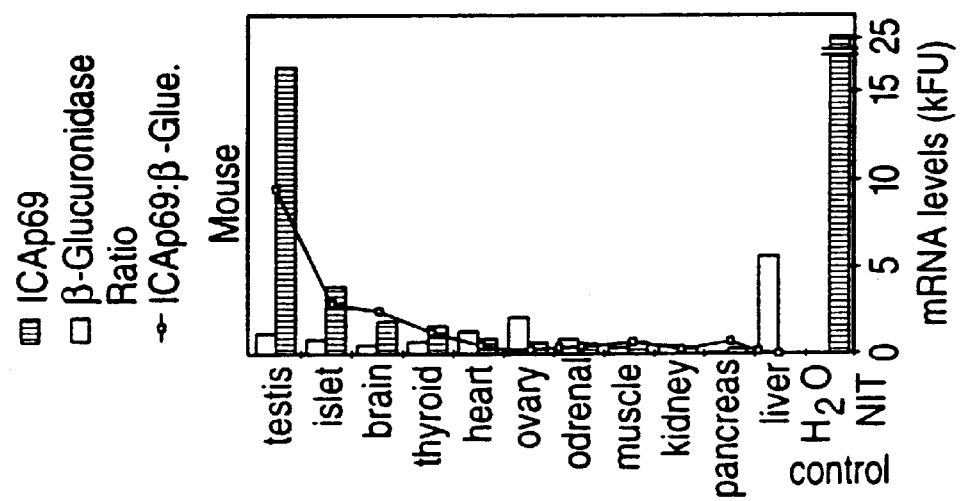

FIG. 23 shows p69 mRNA levels in mouse, rat and human tissues as determined by quantitative RT-PCR. β-glucuronidase mRNA levels serve as internal control. Gene transcription is expressed in relative fluorescence units (RFU) for p69 (black bars), β-glucuronidase (white bars) or as a ratio of p69:β-glucuronidase levels (line).

Figure 24:
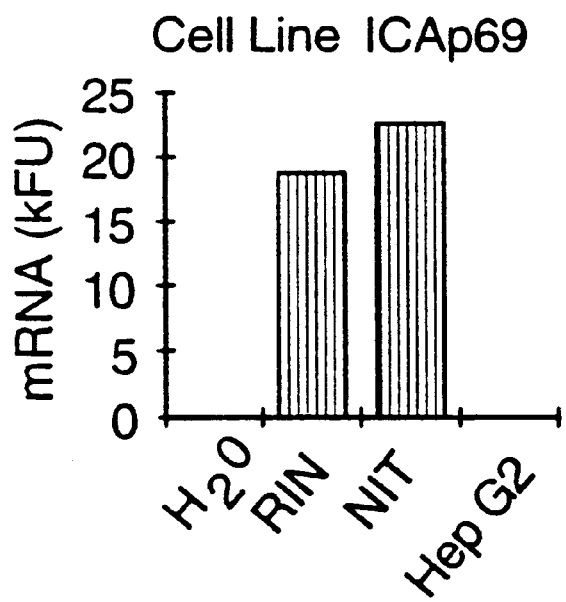

FIG. 24 shows p69 mRNA levels in the RIN (rat insulinoma) cell line, the NIT mouse beta cell line, and Hep-G2 human hepatoma cell line.

Figure 25:
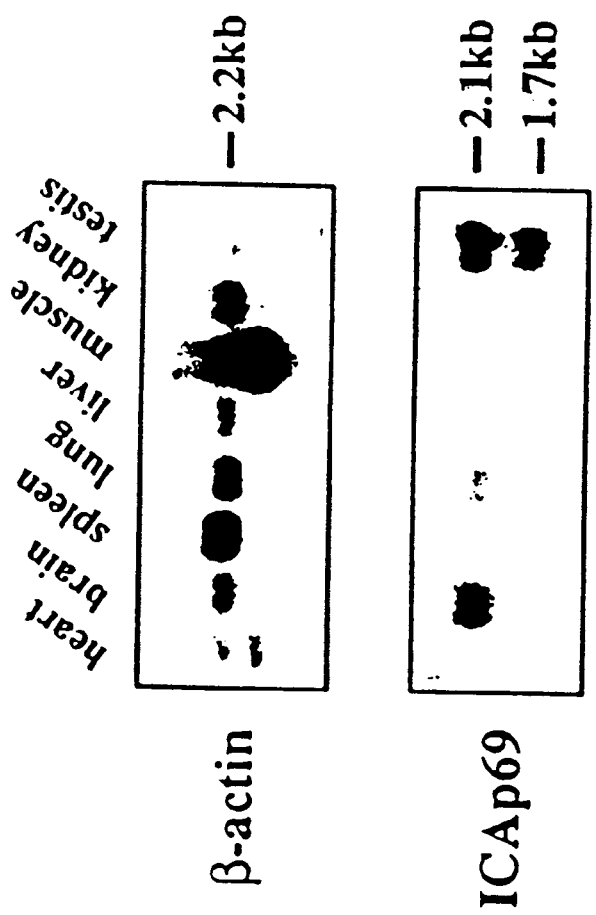

FIG. 25 shows a mouse p69 gene expression as detected by Northern blot analysis. 2 μg poly $(A)^+$RNA from each tissue were hybridized with a 1.4 kb p69 cDNA probe (lower panel). The same membrane was re-hybridized with a β-actin cDNA probe as control (upper panel).

Figure 26:
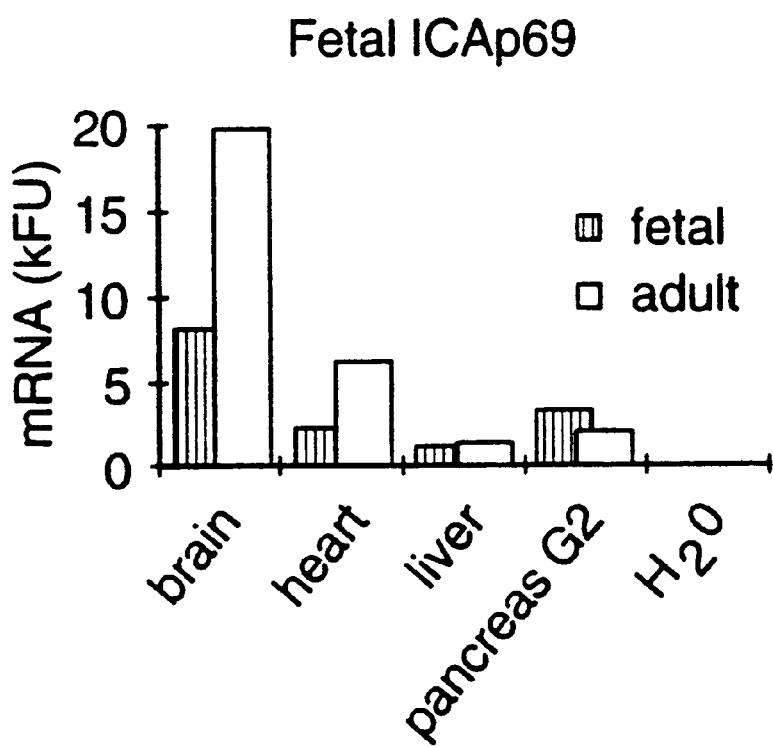

FIG. 26 shows a comparison of p69 mRNA levels in fetal and adult mouse tissues as detected by quantitative RT-PCR.

FIG. 27 shows p69 Western blot analysis of (a) human and (b) mouse tissues. A polyclonal IgG anti-p69 antibody raised against a C-terminal p69 oligopeptide was used as primary antibody, showing a distinct 69 kD band.

Figures 28A, 28B:
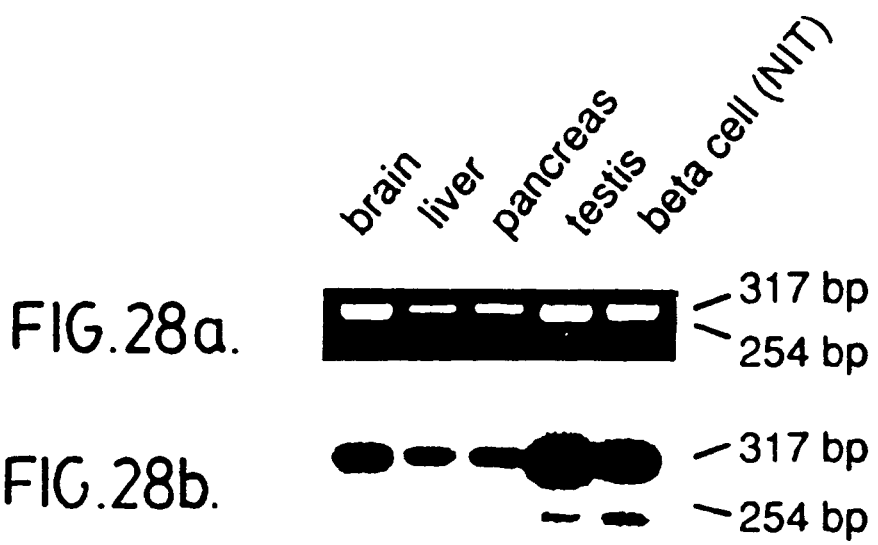

FIG. 28a shows the PCR products of the primer-based reverse-transcription of the cDNAs in various tissues.

FIG. 28b shows a Southern blot demonstrating expression of amplified cDNA of 28a in various tissues.

Figure 29A:
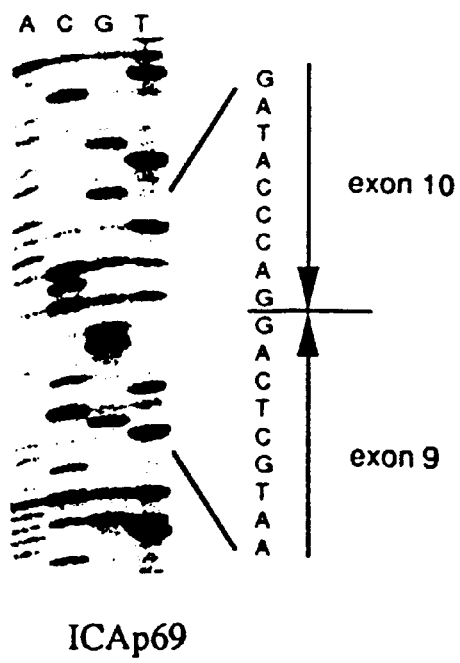
Figure 29B:
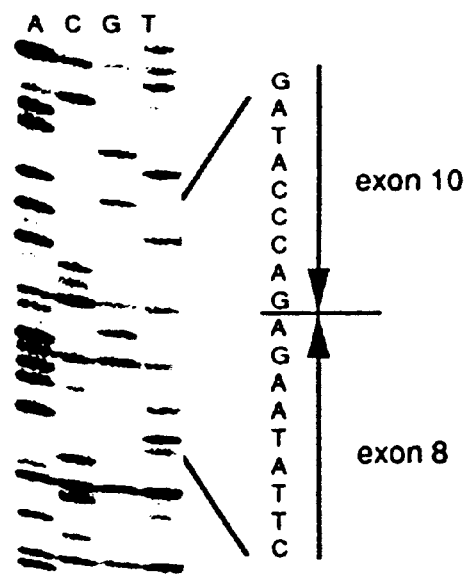

FIG. 29 shows sequence gels of the two PCR products shown in FIG. 28a.

Figure 30:
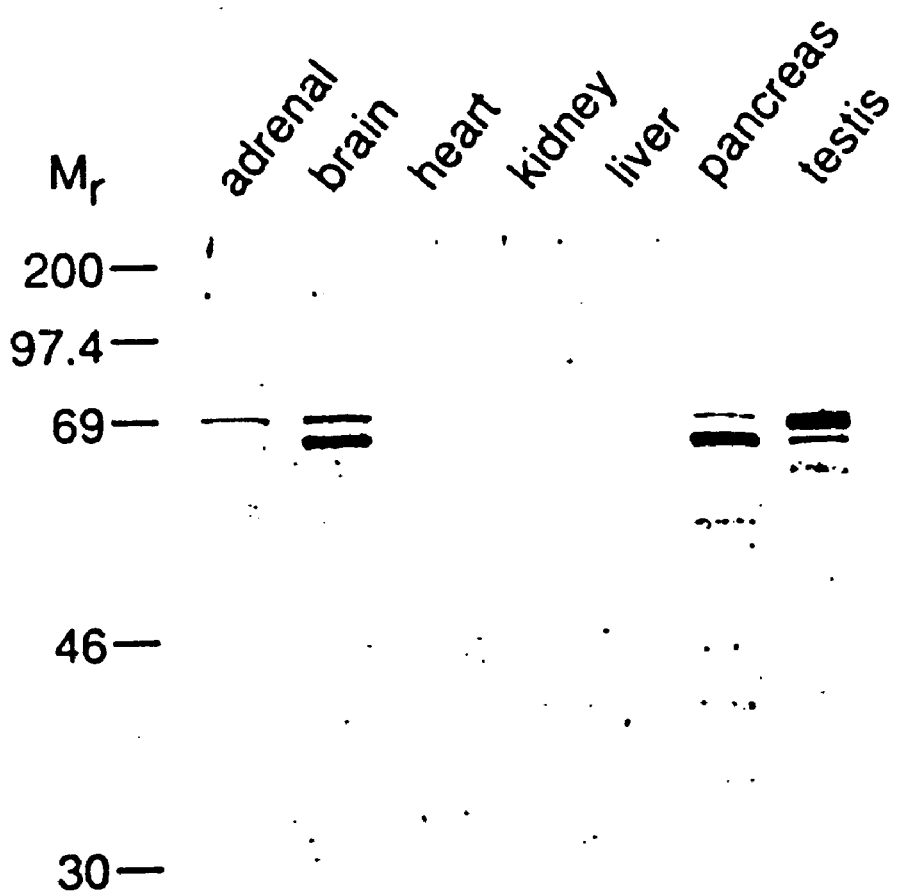

FIG. 30 shows an immunoblot demonstrating expression of p69 in various tissues.

Figure 31A:
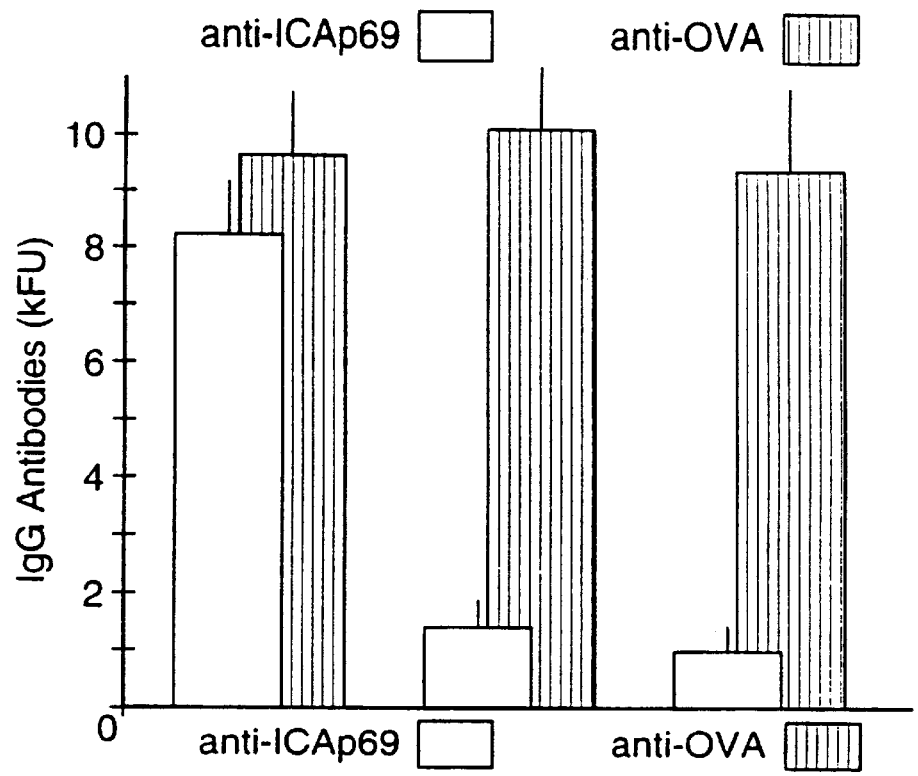
Figure 31B:
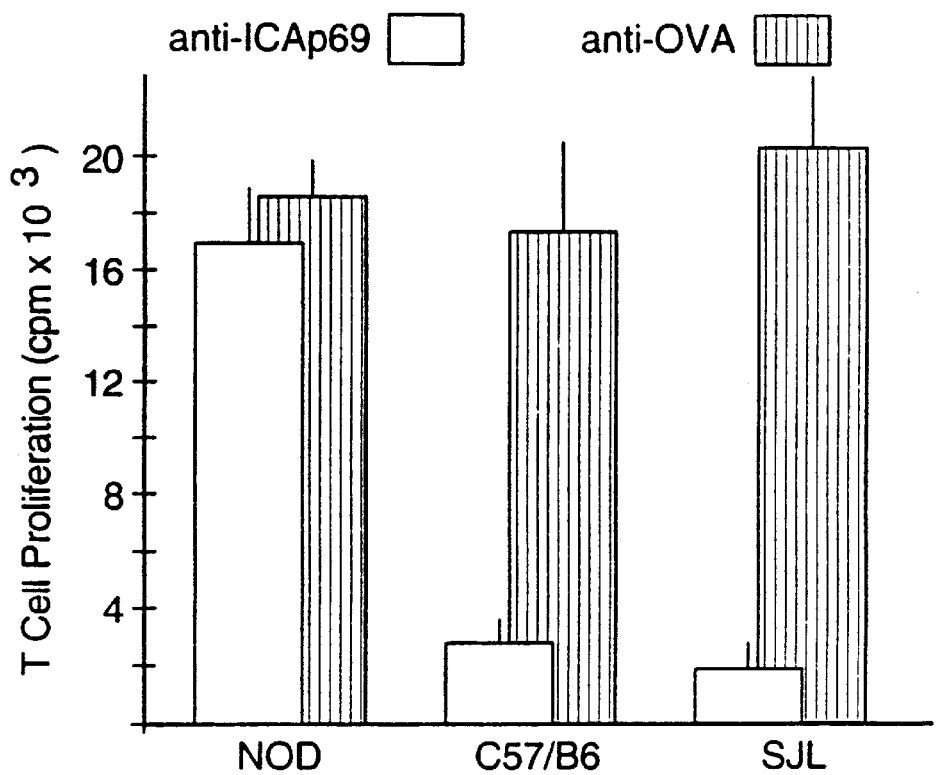

FIG. 31 shows antibody response (upper panel) and T cell proliferative response (lower panel) of the indicated mouse strains to immunisation with p69 protein (open bars) or ovalbumin (shaded bars).

Figure 32:
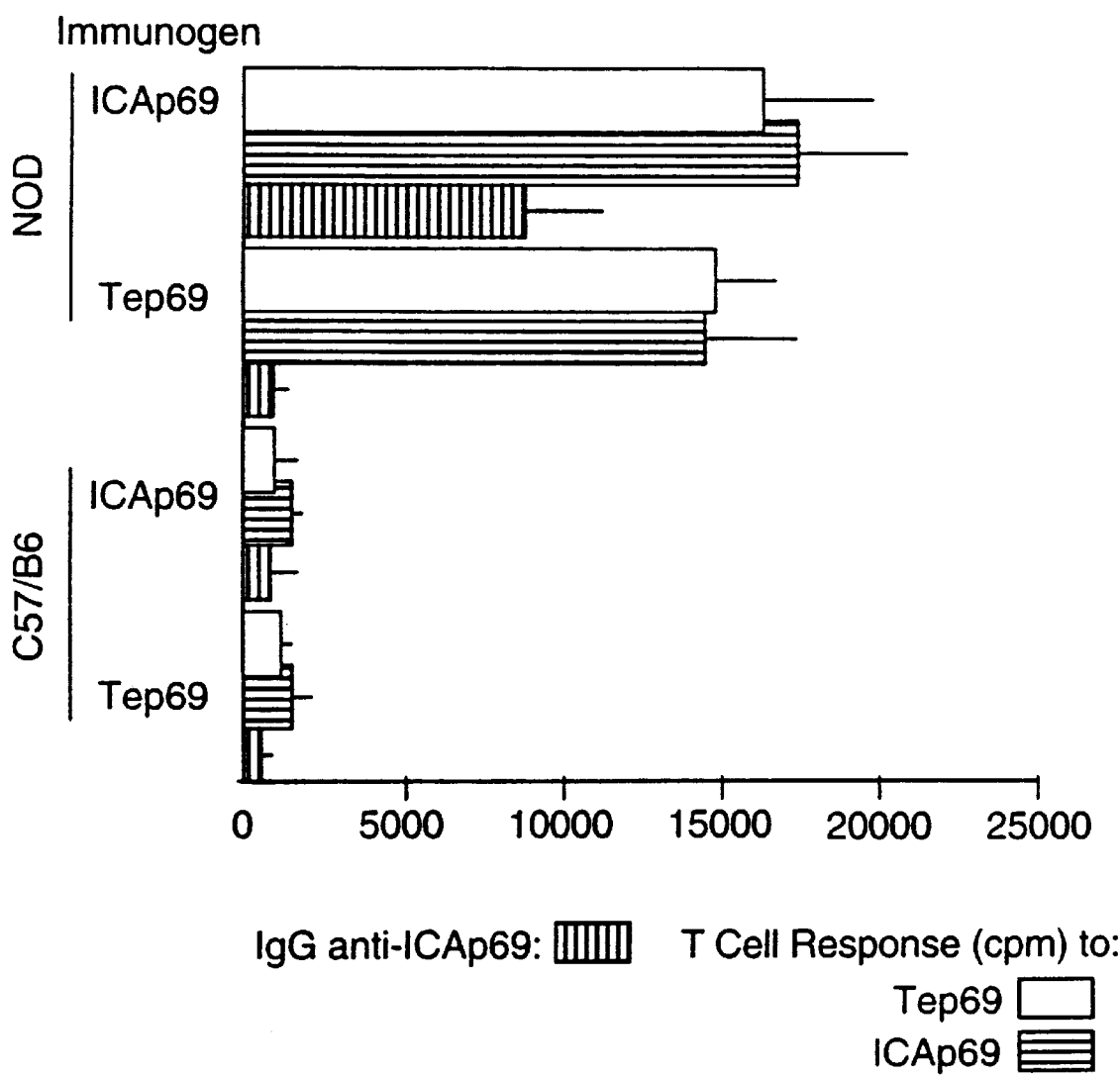

FIG. 32 shows antibody response and T cell response of the indicated mouse strains to immunisation with p69 protein or Tep69.

Figure 33:
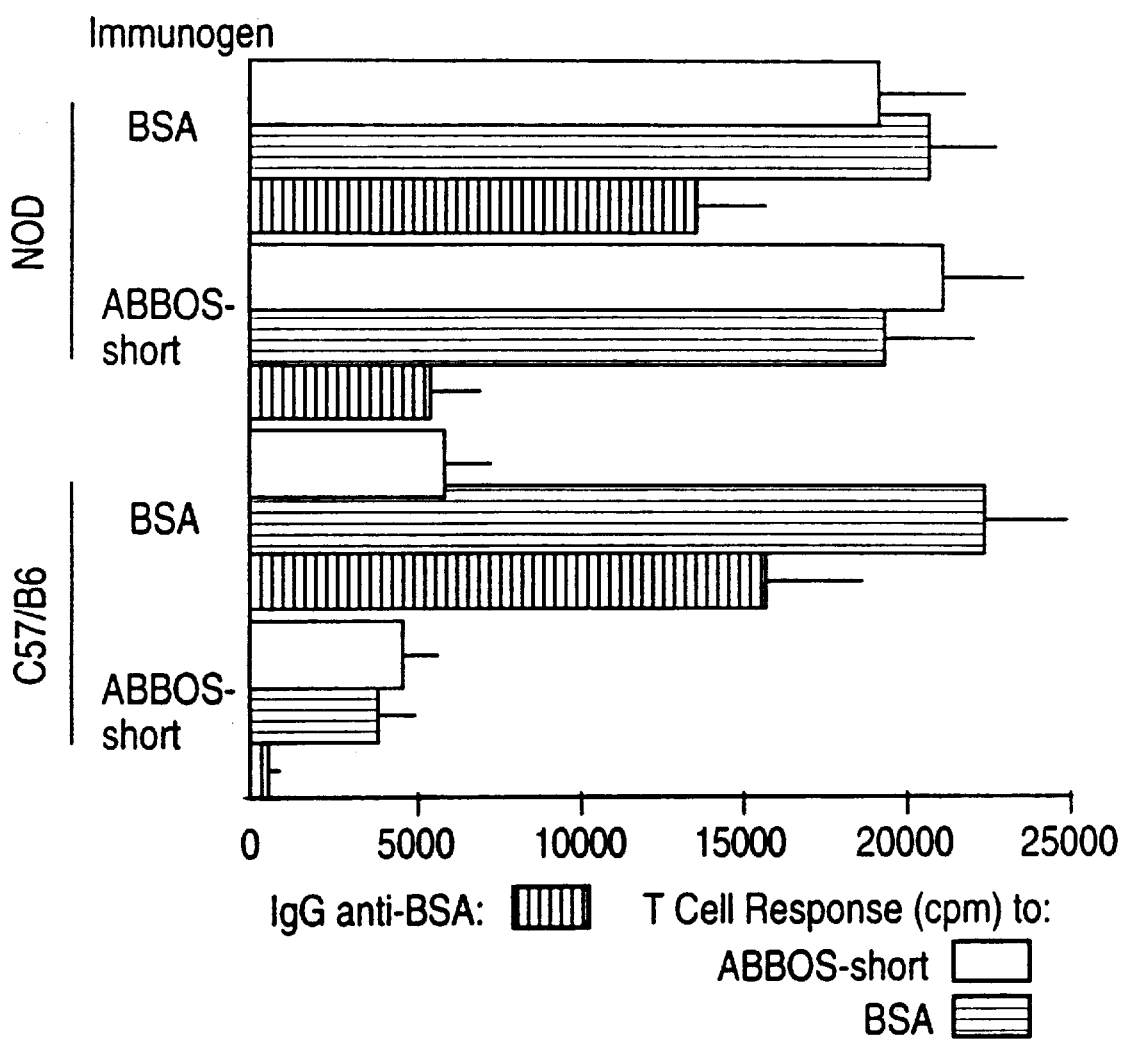

FIG. 33 shows antibody response and T cell response of the indicated mouse strains to immunisation with bovine serum albumin (BSA) or ABBOS-short peptide (ABBOS-short).

DETAILED DESCRIPTION OF THE INVENTION

It has been found previously that in recently diagnosed diabetics, both rat and human, there are increased serum levels of antibodies to BSA and that these antibodies cross-react with a pancreatic β cell protein designated p69. (Glerum et al., (1989), Diabetes Res., vol. 10, pp. 103–107; Martin et al., (1991), Ann. Med., vol. 23, pp. 447–452; Karjalainen et al; (1992), Diabetologia, v. 35, p. 985; Karjalainen et al; (1992), N.Engl. J.Med., v. 327, p. 302).

p69 protein is also known as islet cell antigen p69, abbreviated to ICAp69. As used herein, the terms "p69 protein" and "ICAp69" are synonymous.

It has also been shown that T cells from newly-diagnosed IDDM patients proliferate in response to BSA, whereas T cells from healthy controls do not (Karjalainen et al., (1992), Diabetologia, v. 35, p. 985).

Sequences of rat, mouse and human p69 cDNA sequences coding for human, rat and mouse p69 protein have been cloned.

The cDNA nucleotide sequences and deduced amino acid sequences of human and rat p69 are shown in FIGS. 1 and 2. The mouse cDNA and deduced amino acid sequences are shown in FIGS. 17 and 18. FIG. 4 shows a comparison of human, rat and partial mouse sequences. There are three stretches of the p69 amino acid sequence which show homology to the sequence of BSA. These stretches are boxed in FIG. 4.

Sequencing of further human cDNA clones (eg. FIG. 16a) has confirmed the sequence of FIG. 1a. An interesting natural variant has also been found, clone IS4 (SEQ ID NO 44), which was obtained from a human islet cell library and expresses an extra exon, exon 4. The presence of this exon was confirmed by sequencing of genomic DNA. The nucleotide sequence of exon 4 (SEQ ID NO 45) is shown in FIG. 15. It has termination codons in all reading frames but shows perfect splicing between exons 3 and 5.

Translation of this cDNA produces a truncated form of p69; its amino acid sequence (SEQ ID NO 41) is shown in FIG. 16b. It has been shown that translation of the corresponding mRNA occurs in vivo in β cell (data not shown). The cDNA of IS4, clipped at or slightly downstream of exon 3, has also been used for expression of the truncated form of p69 in vitro in *E.coli*, as described in Example 11. This 100 amino acid fragment of human p69 contains the Tep69 region of the protein and is essentially identical to the corresponding portion of murine p69.

This variant form of p69 is freely soluble and therefore permits a much improved and more convenient assay for detecting anti-p69 antibodies, as will be discussed later.

In the mouse also a number of isoforms of p69 have been detected. These are shown in FIGS. 17 and 18. A comparison of the deduced amino acid sequences from these various isoforms is shown in FIG. 19. As seen in FIG. 20, murine and human p69 proteins share two large, very highly conserved domains (Domain B, 288 amino acids, 99.6% identity; and Domain D, 66 amino acids, 100% identity), a small N-terminus and a central domain with extended sequence diversion (25–33%, 47% at the DNA level). The 5'-untranslated sequences contain circumscript regions of near identity with human and rat p69 (FIG. 21). All p69 isoforms conserve homology with the single antigenic epitope (ABBOS region) in bovine serum albumin (BSA) previously delineated as an autoimmune mimicry epitope in diabetic children.

The presence and full conservation of the homology region to BSA near the N-terminus of murine p69, the ABBOS region, is a critical finding in the context of the proposed role of p69 in diabetic autoimmunity.

Alternative RNA processing of p69 is extensive both in coding and non-coding regions. Interestingly, these processing patterns leave the conserved domains intact. The two murine p69 isoforms demonstrated here are putatively expressed in vivo. Both isoforms were found to be co-expressed in p69 positive mouse but not in any human tissues (Gaedighk et al., submitted). These isoforms thus appear to be species specific. The differentially spliced exon 10 falls in conservation domain C and is only moderately conserved between human and rodents.

As seen in FIG. 21, differentially spliced 5'-untranslated regions in p69 cDNA molecules have been isolated from different species. Two domains of 30–90 bp in the up- and downstream-regions are highly conserved, suggestive of protein binding functions important for the regulation of p69 gene expression.

Immunisation

After immunisation with BSA and p69 protein or peptides, NOD mice generate vigorous antibody and T cell responses to these antigens. The BSA epitope peptide ABBOS was only a minor T cell epitope for C57/B6 and SJL mice which essentially made no response to the p69 self sequences. In addition, the T cell epitope peptide Tep69 was a major T cell epitope for NOD but not other mice. The murine model meets the structural requirements for molecular mimicry to BSA, including conservation of the immunogenic N-terminal T cell epitope, Tep69, homologous to the ABBOS region of BSA. The data establish the primary structure murine p69 isoforms, they demonstrate the presence of p69 self-reactive T cell repertoires in diabetes-prone NOD mice, and they show that the major T cell epitopes delineated by T cell mapping studies in diabetic children also represent major T cell epitopes in diabetes-prone but not other mice.

NOD mice recognize and present the same epitopes in BSA and p69 that were delineated in studies of diabetic children, and the same peptides constitute major parts of the response to the full molecules. Equally important, NOD mice but not other strains readily recruit T- and B cell repertoires that are reactive with self-p69. The size and kinetics of appearance of these repertoires are entirely comparable to those recruited by immunisation with bona fide foreign antigens, BSA or ovalbumin.

These studies thus delineate a novel NOD mouse abnormality that appears epitope-specific for the ABBOS/Tep69 homology regions in two tentatively diabetes-associated molecules. Taken together, the observations demonstrate considerable similarities in the immunology of human and NOD mouse diabetes at the level of single epitope fine structures and antigen presentation of these regions.

Expression of p69

The expression of p69 protein has now been analysed both at gene transcription level and by detection of the protein in tissues in both humans and rodents.

This study establishes a neuro-endocrine gene expression pattern for the islet cell antigen p69 in human, mouse and rat, with highest p69 mRNA detectable in pancreatic islet cells, tests and brain. Low to very low levels of p69 mRNA were detectable by RT-PCR, but not by less sensitive Northern blot analysis, in other endocrine and non-endocrine tissues, like lung, thyroid, ovary, heart, kidney, pancreas, muscle and liver. Because of the non-uniform cellular composition of these tissues it is conceivable that cell types common to many organs (e.g. neuronal or endothelial cells) may have contributed to background p69 expression levels. The absence of p69 transcription in the hepatic cell line HepG2, while p69 mRNA is detectable in whole liver homogenate, would support this view.

Protein expression of p69 was analysed by immunoblotting in human and mouse tissues and found to follow a similar pattern as p69 mRNA levels. Differences between transcription and protein expression observed in some organs (e.g. pancreas) may arise from differential control of RNA in vivo stability or protein turnover rates in these tissues (1). Both the gene segment amplified by RT-PCT and the peptide epitope detected by immunoblotting were located in the C-terminal part of p69, a conserved region showing a high degree (>90%) of protein sequence homology between human, mouse and rat (2). The overall expression patterns with large differences in transcription and protein expression levels among different tissues was similar in all three species.

The tissue distribution of p69 protein, and its early expression in fetal life, suggest its involvement in specific biological functions basic to neuro-endocrine cells. These functions are likely critical when considering the molecule's stringent conservation across different species (2) which extends to genomic structure with identical intron-exon junctions.

Identification of critical peptides

A series of overlapping peptides has now been synthesised corresponding to portions of the amino acid sequence of BSA. Their effect on PBMC as stimulants of a proliferative response in vitro in the presence of IL2 has been examined, using cells from children with recently diagnosed diabetes. The results are shown in Table 1 and are expressed as average stimulation index, as described in Example 4. None of the peptides stimulated any proliferative response of PBMC from normal subjects, even in the presence of IL2.

All patient responsiveness to BSA or its fragments was mapped to the peptide EFKADEKK (peptide P2267; Sequence ID No.: 7), which occurs at amino acid sequence 151 to 159 of pre-BSA.

All 24 BSA-reactive diabetics examined had P2267-specific T cells.

The peptide FKADEKKFWGKYLEIAR (ABBOS) gave the greatest stimulation of PBMC proliferation.

In vivo studies have been carried out with ABBOS peptide and also with the synthetic, BSA-related peptide EFKADEKKFWGKYL (ABBOS-short), as will be described later.

Figures 5, 6:
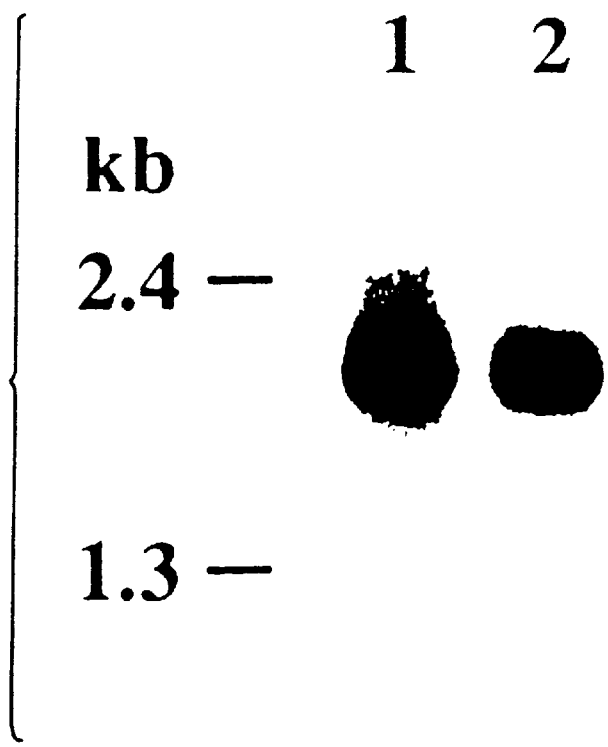
FIG. 5 shows a Northern blot of human (Lane 1) and rat (Lane 2) islet cell mRNA hybridised with the randomly [$^{32}$P]-dCTP-labelled insert of clone pRIc102.
FIG. 6 shows the amino acid sequence homologies between human p69 protein (Sequence ID NO:46 and 48) and bovine serum albumin.

The proliferative response of patient T cells to recombinant human p69 protein was also examined. p69 alone produced little or no proliferative response but if IL2 was also present, a full proliferative response, very similar to that produced by BSA, was obtained (FIG. 6; $R^2=0.84$, p<0.001).

Of the three stretches of p69 sequence showing homology to BSA, the stretch from amino acids 39 to 44 showed homology to the portion of the BSA molecule associated with stimulating proliferation in sensitised IDDM T cells.

Figure 9A:
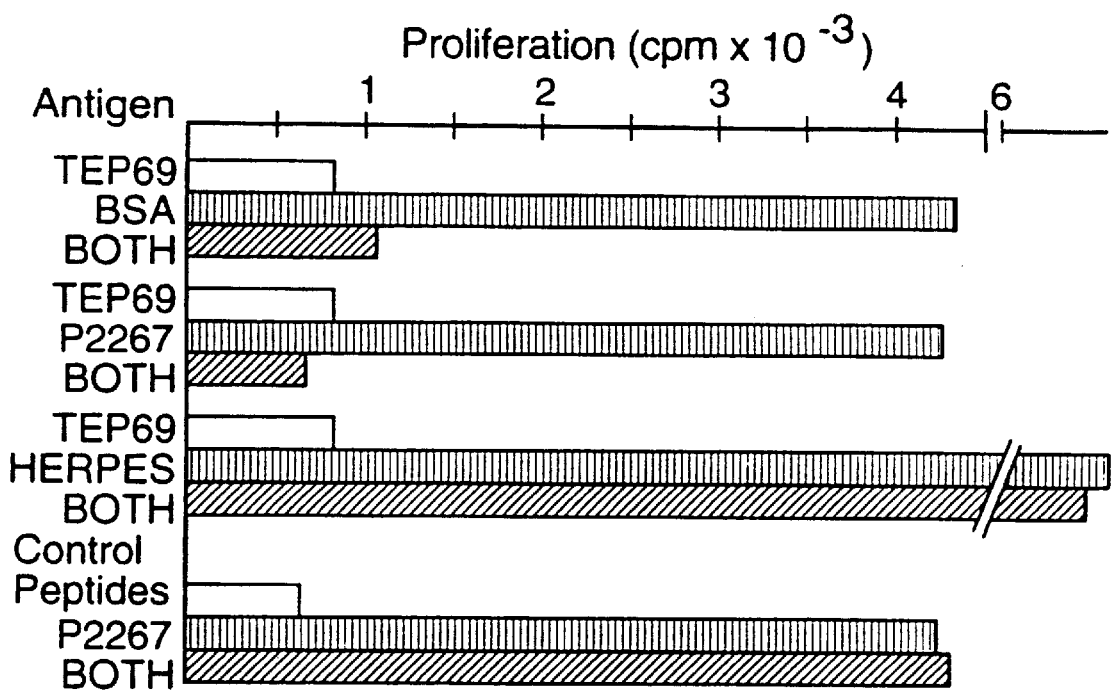
FIG. 9 shows the proliferative responses of T cells from an IDDM patient stimulated with antigens or antigen mixtures, in the absence of IL2 (Panel A) or in the presence of 10 U human IL2 (Panel B).

The p69-derived peptide AFIKATGKKEDE (Sequence ID No.: 23, amino acids 36–47) spanning this region was synthesised (T-epitope peptide 69 or Tep69). 21 of 23 patients tested showed a PBMC proliferative response to Tep69 in the presence of 10 U IL2 but not in its absence (Table 1 and FIG. 9), in contrast to BSA and peptide P2267 which gave PBMC proliferation in the absence of IL2 (FIG. 9A).

Peptides H-1026 (amino acids 48–65), H-1044 (105–116) and H-1031 (200–217), corresponding to sequences at or near the regions of homology, were synthesized and tested and produced no proliferative response, even in the presence of IL2 (Table 1).

Figure 8:
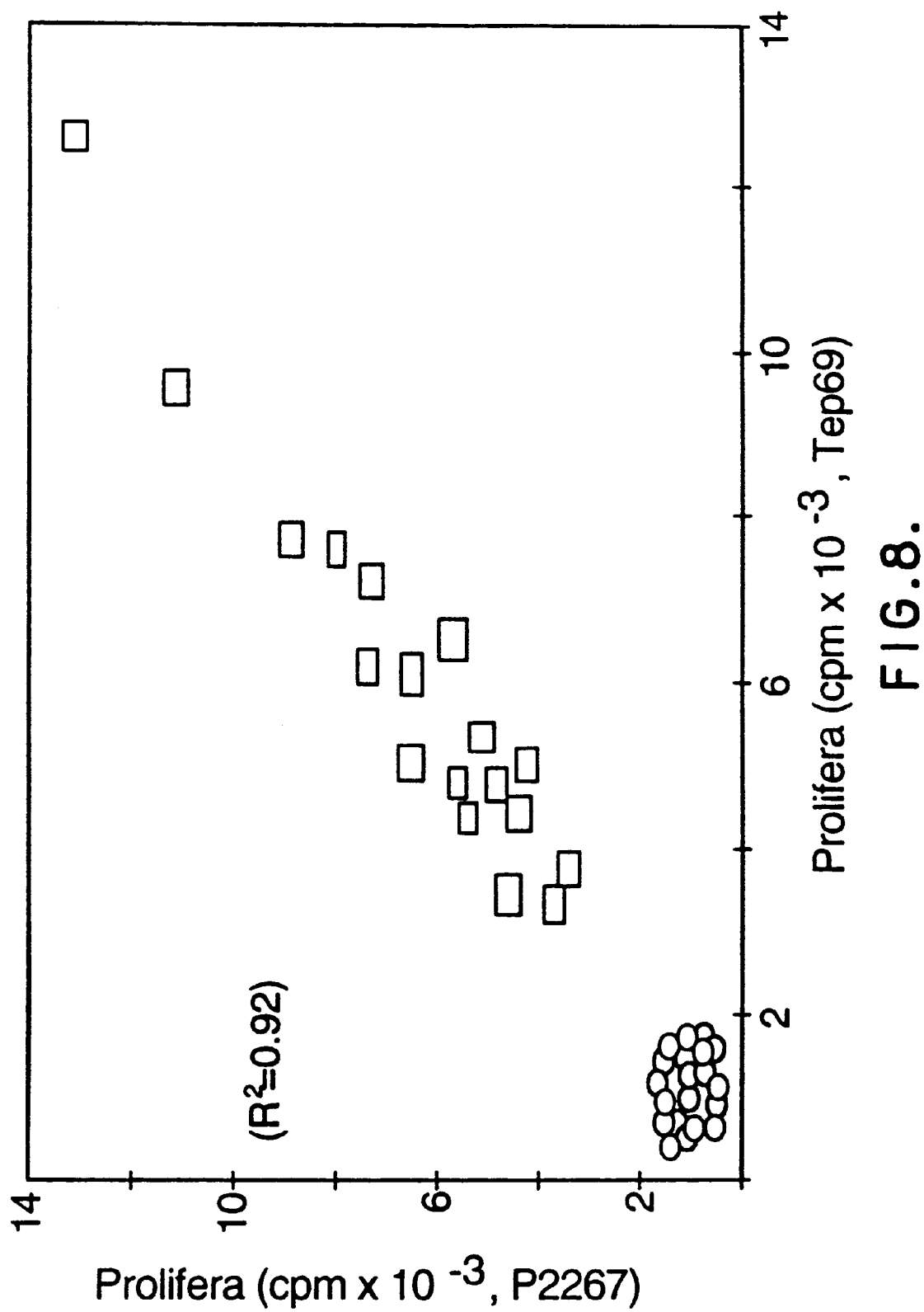
FIG. 8 shows the correlation (□) between IL-2supported proliferative responses of peripheral blood mononuclear cells (PBMC) from 21 patients to Tep69 and to peptide P2267 (EFKADEKK; Sequence ID No: 7). Responses to human, chick or horse albumin or to one of peptides P2240 : IETMREKVLT : Sequence ID No.: 8; P2269 : KLKPDPNTLCDE : Sequence ID No.: 9; or P2270 : YANKYNGVFQE : Sequence ID No.: 10 were compared in parallel (○).

The amplitude of patient IL2-supported PBMC responses to Tep69, P2267 and BSA varied but were significantly higher than responses to control antigens or peptides (P<0.0001). There was a high correlation between the response to Tep69 and the response to P2267, as seen in FIG. 8 ($R^2=0.92$).

Replacement of the BSA-derived -DE- with the p69derived -TG-, as in peptide C164 (Table 1) did not affect stimulation of the proliferative response, thus defining the 6-amino acid core homology motif recognised by patient T cells in BSA and p69.

The response of IDDM T cells to mixtures of peptides was examined. It was found, unexpectedly, that peptide Tep69 suppressed the proliferative response to BSA or to the peptide P2267, as seen in FIG. 9A.

Figure 9B:
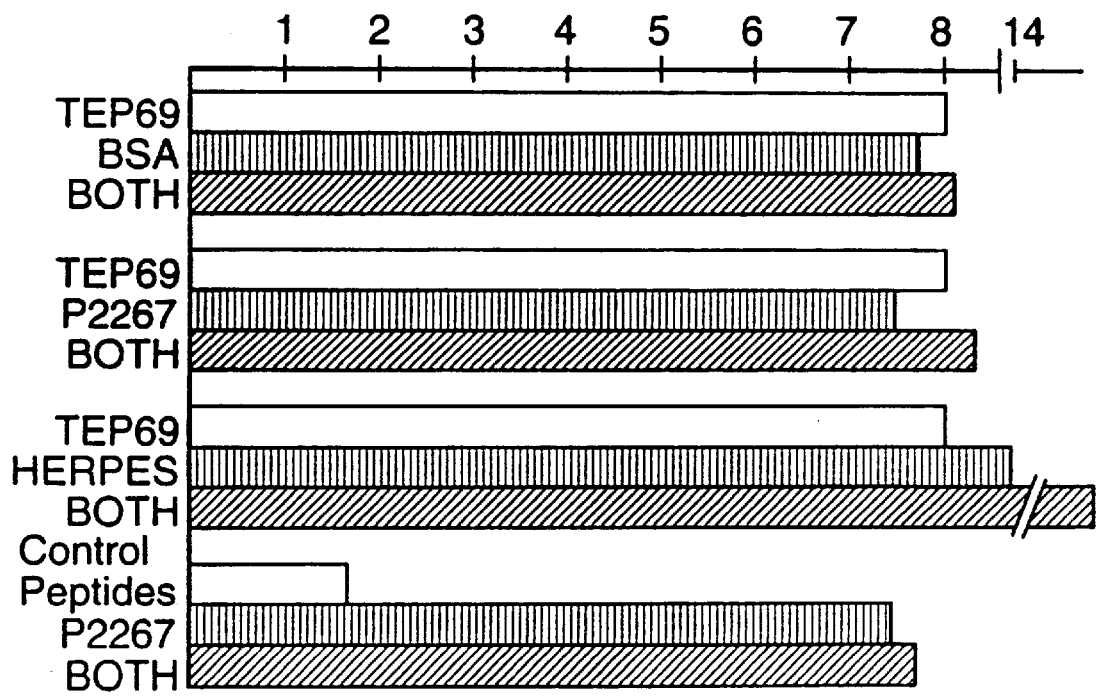

Cultures containing 1 μg Tep69 and BSA, or equimolar concentrations of Tep69 and p2267, showed no proliferation unless exogenous IL2 was added (FIG. 9B). Suppression was sequence and antigen specific: several unrelated peptides failed to suppress P2267 (or BSA) responses, and responses to Herpes antigen were unaffected by Tep69. The similarity of IL2-supported response amplitudes and the presence of peptide-specific suppression imply that the same T cells are stimulated by BSA/P2267 and p69/Tep69.

It was also found that the peptide 152–169 homologue ABBOS-D suppressed the proliferative response to peptide 152–169, ABBOS, as seen in Table 1.

The inventor then examined the effect of various peptides on the early stages of T cell activation, as indicated by induction of IL2R (Example 6). T cells from an IDDM patient and a healthy control were exposed to P2267, Tep69 or a mixture of these peptides. The results are shown in FIG. 10. Control cells did not show IL2R induction in response to any of these treatments, although they did show IL2R induction in response to Herpes control antigen. In IDDM cells, either P2267 or Tep69 activated IL2R transcription to a similar extent, even though only P2267 triggered a proliferative response in these cells. These cells also showed IL2R induction in the response to a mixture of P2267 and Tep69, and in response to Herpes control antigen.

A triggering of early T cell activation events without sufficient autocrine ILR production for T cell proliferation is the hallmark of anergy (Lake et al. (1993), Int. Immunol., vol. 5, pp. 461–466).

The inventor's results suggest, unexpectedly, that anergy induction can be dominant and can occur even in the presence of the fully stimulatory agonist. This offers unsuspected new possibilities for control of pathological conditions involving T cell sensitisation.

Prevention of IDDM

In accordance with this invention, it has been possible to intervene successfully in the development of IDDM in NOD mice by neonatal treatment with the peptide Tep69 (AFIKATGKKEDE).

As seen in FIG. 13, and described in Example 8, a single intraperitoneal injection of Tep69 completely prevented the development of IDDM in over 80% of treated animals and delayed the appearance of the disease in the remainder.

It has also been found that the development of IDDM in NOD mice can be successfully prevented or delayed even with later intervention, by immunotherapy with BSA or BSA-derived peptides administered along with an adjuvant.

As seen in Example 7, immunotherapy with BSA or the peptide ABBOS together with an adjuvant, early during the pre-diabetes disease process in NOD mice, gave complete prevention of IDDM. A regime of an initial subcutaneous injection of protein or peptide and adjuvant, followed a week later by an intraperitoneal booster injection of the same mixture, was employed. At nine months of age, treated mice showed no cases of IDDM whereas controls had close to a 70% incidence of IDDM (FIG. 11).

As seen in FIG. 12, mice treated with BSA or ABBOS showed a massive antibody response, with high levels of circulating anti-BSA antibodies from around five weeks after treatment.

Example 9 and FIG. 14 show that a similar regime of subcutaneous initial injection followed by intraperitoneal booster using the BSA-derived peptide EKFADEKKF-WGKYL (ABBOS-short) gave similar results to those seen with ABBOS ie. complete protection against development of IDDM and massive humoral antibody response. When ABBOS-short was administered as a single subcutaneous injection only, IDDM development was delayed but protection was less complete than when a booster injection was used. The humoral antibody response was also lower with the single subcutaneous injection.

In contrast to the results seen with BSA immunotherapy, immunisation with Tep69 and adjuvant accelerated diabetes development and significantly increased the disease incidence.

The present invention is therefore the basis of a new model of autoimmunity and a new method for controlling T-lymphocyte-mediated immune responses.

According to this new model, the normal immune repertoire of T lymphocytes includes cells which are inherently autoreactive but these cells are rendered anergic by contact with their autoantigen and are eventually eliminated. If these cells contact an exogenous mimicry antigen which is structurally related to the autoantigen, they may be rescued from inactivation by autoantigen and stimulated to proliferate, generating large pools of autoreactive cells which are inherently able to destroy a target tissue.

In the case of IDDM, it is postulated that during a critical time of post-natal T cell repertoire development, dietary BSA-derived peptides such as ABBOS establish the relevant sensitised T cell pool. When such cells encounter dietary BSA or its fragments, they are stimulated to proliferate. Tep69 or other p69 derived peptides, however, can ablate this T cell pool by anergy induction. There is, however, a quantitative threshold above which the BSA-peptide stimulated T cell pool is too large to be controlled by p69-derived peptides such as Tep69.

If anergic peptides such as Tep69 are administered early in life to subjects pre-disposed to development of IDDM, appearance of the disease may be completely prevented. In mice, it has been shown that Tep69 treatment neonatally is highly effective. Human subjects should be treated correspondingly early, preferably within three months of birth.

An alternate therapeutic approach provided by the present invention is immunotherapeutic intervention at a later stage, after the pool of sensitised T cells may be too large to be ablated by administration of anergenic peptides such as Tep69.

The presentation of BSA or BSA-derived peptides such as ABBOS or ABBOS-short in the context of an adjuvant such as incomplete Freund's adjuvant, at a time when the disease process has begun (insulitis begins at about 3–4 weeks of age in the inventor's colonies), was shown to effectively prevent diabetes development in female NOD mice. This provides a new method for intervening to prevent development of IDDM in susceptible subjects.

T lymphocytes can be classified into 2 major categories: TH1-type helper cells and Th2-type helper cells. CD4=TH1-type helper cells support cell mediated immune reactions including the induction and expansion of CD8+ effector cells (e.g. cytotoxic lymphocytes). TH2-type lymphocytes produce IL4, IL6 and IL10 as major secretory products. IL10, a major B cell growth factor, is also able to effectively inhibit TH1-type cells while TH1 products such as interferon gamma can modify other T cell functions as well as B cell responses. Thus a finely tuned balance characterises the healthy immune system. There is good consensus that Type 1 diabetes reflects an imbalanced immune response with a heavy bias towards TH1-type immune reactivity.

Immunotherapy with a mimicry antigen such as BSA or its fragments, as successfully demonstrated herein, may be another way to move the immune system balance away from TH1-type immune reactivity towards TH2-type immune reactivity. The development of high levels of anti-BSA antibodies in mice treated with BSA and particularly in mice treated with the peptide ABBOS, which is a small molecule and therefore a weak antigen, is consistent with a massive TH1 to TH2 shift in the immune response.

The present invention provides two new approaches to the immunotherapy of IDDM which may be employed as alternate therapies or may be used in conjunction with each other or at different stages of disease development.

Administration of anergenic peptides is the preferred treatment in the neonatal period. At a later stage in the progression towards IDDM, it is likely that immunotherapy will be more effective.

While the underlying mechanisms are not yet completely understood and the methods of the invention may nevertheless be utilised in advance of mechanistic explanations, it is interesting to consider the methods of the invention in light of our expanding understanding of the immune system.

High affinity anergenic peptides such as Tep69 and ABBOS-D can directly anergize TH1-type cells. The inventors have demonstrated the presence of such cells and their requirement for IL2 production identifies them as TH1-type. Anergenic peptides fail to trigger IL2 production.

Direct inactivation of sensitised T cells will reduce their pool size and therefore disease activity. The dominance of anergy induction demonstrated by the inventors is of major importance in this therapeutic approach. Low anergen concentrations are effective, suggesting high affinity binding.

15% of all future Type I diabetes cases derive from families with a history of the disease and these "at risk" subjects are suitable candidates for treatment with the methods of the invention. For the remaining population with no family history, pre-screening can be carried out to identify a target population for treatment. For example, particle concentration fluoroimmunoassay (PCFIA) to detect circulating antibodies to BSA, as described in International Patent application no. PCT/CA93/00304, may be employed. A similar assay may be directed to detection of circulating antibodies to p69 protein.

The present invention provides a new convenient clinical assay for detecting circulating anti-p69 antibodies employing the truncated p69 protein described herein. The solubility of this portion of p69 means that conventional immunoassay techniques may be employed, using the truncated protein as target antigen. This portion of the molecule includes the important Tep69 region and will detect antibodies to epitopes in this region. The absence of the remainder of the p69 protein will reduce non-specific background due to antibodies to epitopes remote from the Tep69 region. Those skilled in the art will readily appreciate that the truncated p69 can be employed as antigen in any suitable immunoassay system, including enzyme-linked immunosorbent assays (eg. indirect, direct, antibody sandwich, and double antibody sandwich techniques), radio immunoassay and the like.

Alternatively, or additionally, lymphocyte proliferation in response to BSA or its fragments or analogues or in response to p69 protein or its fragments or analogs in the presence of IL2 or other cytokines may be assessed by proliferation assay as described in the same application or in Example 3 herein.

Various methods of preparation and administration of anergenic proteins or peptides and mimicry antigens or peptides may be employed, as will be understood by those skilled in the art.

Short peptides of up to about 20 amino acids may be prepared by conventional chemical synthesis. Their anergenic effects may be screened in vitro against T cells from patients, in a proliferative assay system as described in Example 3. Peptides giving suppression of the proliferative response of sensitised T cells can thus be selected.

Similarly mimicry antigens or active fragments can be screened for stimulation of proliferation of sensitised T cells by the same assay system.

Alternatively, proteins or peptides may be synthesised by recombinant techniques. For example, the cDNA sequence of human p69 provided herein makes it possible to produce p69 protein or fragments thereof by standard techniques, as will be understood by those skilled in the art and exemplified in Example 2.

When chemically synthesised or recombinant anergenic proteins or peptides are employed alone to prevent expansion of the disease-mediating T cell population they may be administered to mammals, including humans, by injection—for example, by daily intravenous or intramuscular injection. Alternatively, the peptides may be administered by slow release from a depot injection, or from an implanted osmotic pump, such as an Alzec pump. Such methods of administration are well known to those skilled in the art.

The peptides may also be administered orally—strategies for oral delivery of peptides, such as by enteric-coated capsules, are known to those skilled in the art.

Short peptides such as Tep69 will be excreted in the urine. Better retention can be obtained by use of a longer molecule, for example a tandem repeat containing 2 to 40 copies of the peptide sequence. Such tandem repeat sequences can be prepared by established recombinant DNA techniques, as described for example in "Current Protocols in Molecular Biology", Eds. Ausubel, F. M. et al. (1994), Publ. John Wiley & Son.

Additionally, anergenic peptides may be administered to subjects by means of a viral vector, for example a defective adeno 5 virus which is not pathological and does not replicate. Such techniques are known to those skilled in the art and suitable viruses are obtainable from the National Institute of Health. The E1 or E3 viral gene is replaced by the DNA for the desired peptide, as described, for example, in Rosenfeld et al., (1991), Science, vol. 252, pp. 431–434; Stratford-Perricaudet, et al., (1992), Bone Marrow Transplant, vol. 1, pp. 151–152; Yang, N. S., (1992), Crit. Rev. Biotechnol., vol. 12, pp. 335–356.

When immunogenic compositions comprising mimicry antigens such as BSA or fragments such as ABBOS or ABBOS-short are employed to control or prevent T cell-mediated disease, these may include a variety of suitable adjuvants, commonly used as 0.05 to 0.1 percent solution in phosphate-buffered saline.

Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

Desirable characteristics of ideal adjuvants include:
(1) lack of toxicity;
(2) ability to stimulate a long-lasting immune response;
(3) simplicity of manufacture and stability in long-term storage;
(4) synergy with other adjuvants;
(5) capability of selectively interacting with populations of antigen presenting cells (APC);
(6) ability to specifically elicit appropriate T.1 or TH2 cell-specific immune responses; and
(7) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immune-modulators or adjuvants. Thus, Lockhoff et al. (U.S. Pat. No. 4,855,283) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Patent No. 4,258,029 granted to Moloney, and incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al., reported that octadecyl esters of aromatic amino acids complexed with a recombinant hepatitis B surface antigen, enhanced the host immune responses against hepatitis B virus.

As will be understood by those skilled in the art, a variety of immunisation regimes may be suitable. An initial administration of an immunogenic composition comprising a BSA fragment such as ABBOS or ABBOS-short may be followed at a suitable interval by one or more booster doses. As shown in Example 11, NOD mice recognize the same diabetes-associated p69 epitopes as are recognised by T cells from diabetic children. The NOD mouse therefore provides an excellent model for study of mechanisms in the development of IDDM and for screening or testing of potential therapeutic interventions, as illustrated by the experiments described herein.

EXAMPLES

Example 1

Sequencing of rat, mouse and human islet p69 cDNA
cDNA Libraries

Islet cells were purified as described by Glerum et al. (Diabetes Res., v. 10, pp. 103–107 (1989) and poly (A) RNA was purified as described by Miyazaki et al. (J. Exp. Med., vol. 178, pp. 252–269 (1993)). Two $\mu$g of poly(A) RNA from rat or human islet cells were used to construct cDNA libraries using Uni$\lambda$ZAP XR phage (Stratagene, La Jolla Calif.) according to the manufacturer's recommendations. A total of $7.5 \times 10^4$ phage (99.5% recombinant) from the rat islet cDNA library were overlaid (37° C./12 hr) with Hybond-C-Extra filters (Amersham, Arlington Heights, Ill.). After blocking (50 mM Tris-HCl pH7.2, 100 mM NaCl, 0.1% Triton X-100, 4° C./16 hr), membranes were probed with the rat anti-BSA antibodies previously used to identify p69 (Karjalainen et. al., (1992) N. Engl. J. Med., v. 327, pp. 302–307) Ann. Med., v. 23, pp. 447–452). An immunoreactive phage with 0.7 kb insert was then used to re-screen the library and identify the 2.1 kb clone pRIc102 as described (Miyazaki, supra). The human cDNA library was screened in parallel. Immunoreactive recombinants were confirmed to hybridize with insert of the sequenced rat clone pRIc102 and several additional cross-hybridizing clones were identified.

A mouse p69 cDNA fragment cloned from a mouse β cell line was PCR amplified using primer pairs derived from the rat p69 sequence. This fragment, which contained nearly the full coding sequence for mouse p69 protein, was cloned and sequenced.

DNA sequencing and analysis

Several phages isolated from the rat and human cDNA libraries were converted into phagemid by in vivo excision. Recombinant plasmid DNA (0.3 μg) were applied to cycled sequencing (AutoCycle sequencing kit, Pharmacia, Montreal, Que.) for primer walking, using $^{32}$p end-labeled T3 and T7 primers initially. Thereafter 18–20 mer p69 primers were synthesized from the sequences generated on both DNA strands. After 25 cycles, samples were loaded on 6% acrylamide sequencing gels, separated and exposed to film. Both strands were sequenced.

FIG. 1a shows the cDNA nucleotide sequence and deduced amino acid sequence of human p69 protein. FIGS. 2a & b shows the corresponding sequences of rat p69 protein. The cDNA and deduced amino acid sequences of the mouse cDNA fragment are shown in FIGS. 3a & b.

Example 2
Preparation of recombinant human p69

The human p69 gene was subcloned into the Promega PinPoint vector system (Promega, San Diego) which gave expression of a fusion protein containing p69 protein and a bacterial peptide which is endogenously biotinylated in *E. coli*. The fusion protein was then purified on a monomeric Streptavidin affinity column and the bacterial peptide was cleaved off using Factor X protease. Final purification of p69 protein was by gel filtration.

Example 3
Proliferative Response of PBMC to BSA and p69

Peripheral blood mononuclear cells (PBMC) were obtained from 7 children with recent onset diabetes and 12 healthy subjects and their response to BSA and rec-p69 protein were examined in a T cell proliferation assay, as follows.

Cultures containing 5×10$^4$ cells were incubated for 7 days at 37° C. in serum-free HL-1 medium (Ventrex, Portland, Me.) containing 1 μg antigen per well for test samples.

Control cultures were treated with 1 μg human, chick or horse albumin or an equivalent volume of control recombinant antigen prepared from lysates of *E. coli* carrying wild type plasmid.

After an overnight pulse of 1 μci $^3$H thymidine, cultures were harvested and submitted to liquid scintillation counting. Proliferation was expressed as cpm $^3$HTdR×10$^{-3}$.

Figure 7A:
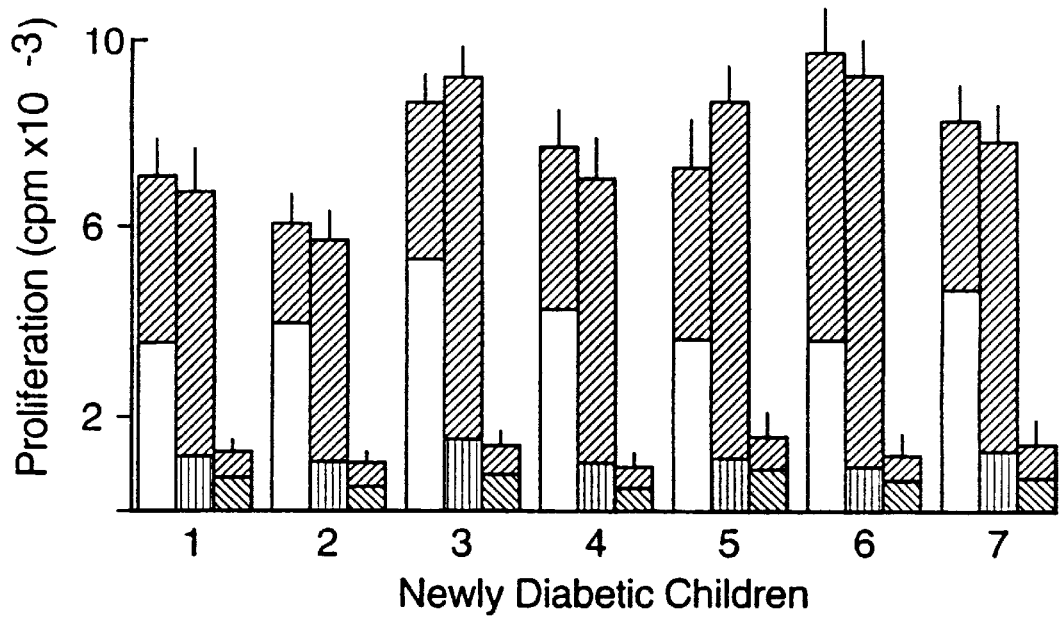
FIG. 7 shows proliferative responses of T cells (expressed as thymidine incorporation in cpm $^3$H×10$^{-3}$) from 7 patients (upper panel) and 12 healthy control subjects (lower panel) to bovine serum albumin (□), recombinant human p69 (■) or control preparations (dotted shading). Diagonal hatching indicates magnitude of proliferative responses to these agents in the presence of 10 U IL2.
Figure 7B:
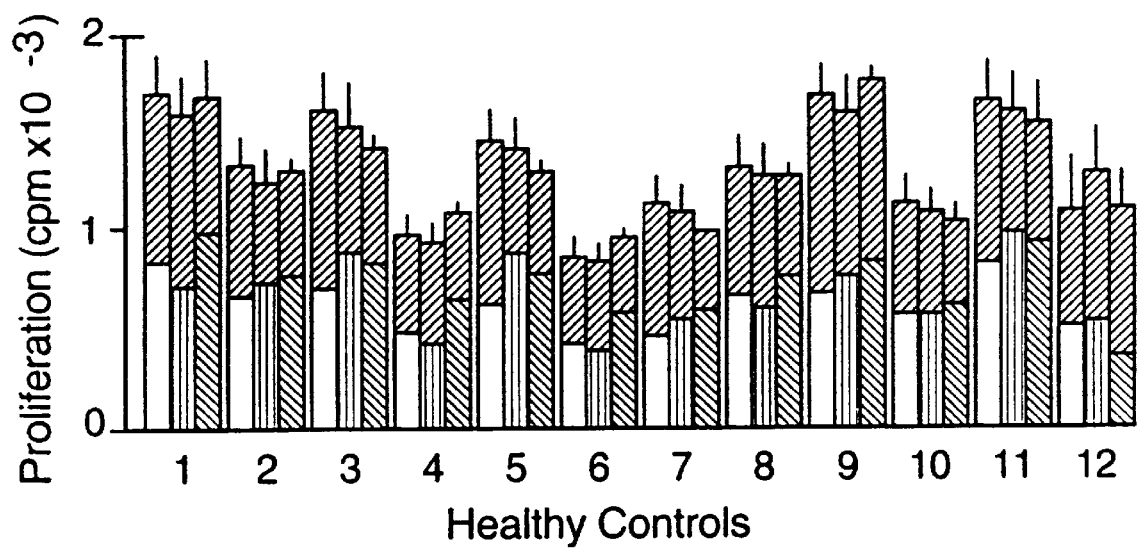

Results are shown in FIG. 7. Proliferation in control cultures was not statistically different among agents used (p>0.6) and data were pooled to give control data shown in FIG. 7 as open columns.

A parallel set of cell cultures was incubated with the same test antigens or control agents in the presence of 10 U human IL2.

Samples from healthy subjects showed no significant proliferative response to BSA or to rec-p69, either with or without IL2 (FIG. 7, Panel B).

In the absence of IL2, all patient samples showed a marked proliferative response to BSA but at best a small proliferative response to rec-p69 (FIG. 7, Panel A).

In the presence of IL2, all patient samples showed an increased response to BSA and a similar level of response to rec-p69 (FIG. 7, Panel A).

Example 4
Proliferative Response of PBMC to peptide fragments 27 overlapping peptides corresponding to stretches of the amino acid sequence of BSA were synthesised by conventional methods and their efficacy in stimulating a proliferative response in the presence of IL2 was examined in PBMC from children with recent onset diabetes.

Proliferative responses were measured as described in Example 3, the incubation medium of test samples containing 1 μg BSA or 1–30 μg peptide plus 10U IL2.

Control cultures were stimulated with 1 μg ovalbumin or horse or human albumin. Results with these control agents were not significantly different and control data were pooled. A 4 h. pulse with 1 μCi $^3$H thymidine was used.

Each synthetic peptide was tested with PBMC from at least 3 children with recent onset diabetes. Results for 13 peptides mapping most closely to the critical peptide sequence are shown in Table 1. Stimulation Index=$^3$H Thymidine Incorporation in peptide-stimulated culture in cpm divided by Thymidine incorporation in control culture in cpm.

Cell cultures from a total of 24 BSA-reactive patients were tested with peptide P2267 in the presence of IL2 and all showed proliferative responses.

Peptides corresponding to stretches of the amino acid sequence of human p69 were also synthesised and the proliferative response to patient PBMC cultures to these peptides were similarly tested, in the presence of IL2.

The results are also shown in Table 1.

Example 5
Responses to antigen mixtures

PBMC cultures from five patients with recent onset diabetes were stimulated with antigens Tep69, BSA, Peptide P2267 and Herpes Simplex antigen (Connaught Laboratories) and with various mixtures of these antigens (1 μg of each antigen per culture); their proliferative responses to the mixtures were compared with their responses to the component antigens alone.

Proliferation assays were conducted as described in Example 3. Control cultures were treated with 1 μg horse albumin or with the peptides P2240, P2269, P2270 or H1029. Results with control antigens were similar and data were pooled.

All patients showed similar results. A typical set of results is shown in FIG. 9.

Responses were expressed as mean of triplicate cultures; variations were <12%. Responses in the absence of IL2 are shown in FIG. 9, Panel A. Parallel cultures were treated with the same antigens and antigen mixtures in the presence of 10U IL2. The results are shown in FIG. 9, Panel B).

In the absence of IL2, a mixture of BSA and Tep69 gave a proliferative response only slightly higher than Tep69 alone. The proliferative response to P2267 was similarly suppressed in the presence of Tep69. In contrast, the presence of Tep69 did not affect the proliferative response to Herpes Simplex antigen (FIG. 9, Panel A).

In the presence of IL2, the suppression of response to BSA or to P2267 by Tep69 was overcome and full proliferative responses to these agents were seen (FIG. 9, Panel B).

A similar experiment with a mixture of ABBOS and ABBOS-D, in the absence of IL2, showed suppression of the response to ABBOS (Table 1).

Example 6

Replicate cultures of PBMC from a child with recent onset diabetes and a healthy control subject were stimulated with P2267, Tep69, Herpes simplex antigen or a mixture of P2267 and Tep69 (1 µg antigen per culture) as described in Example 3. After 2 days of incubation, one patient cell culture and one healthy control culture were harvested for RNA extraction and measurement of IL2 receptor transcripts by RT-PCR, as described by Cheung et al., (1991), J. Biol. Chem., v. 266, pp. 8667–8670. PCR was used to amplify a 739 bp fragment of IL2R coding sequence from patient and control and also a 430 bp region in the human β-actin gene of patient.

Reverse transcribed cDNA from purified, unstimulated normal T- and B lymphocytes served as controls. After standard 30-cycle amplification, PCR products were size separated, blotted to nylon filters and hybridized to [$^{32}$P]-endlabelled, internal reporter probes. Exposed films were scanned with an Apple OneScan™ instrument. IL2R primers: 5'-GGTGCCTGGCTGCCAGGCAGA (Sequence ID No.: 26) 5'-CCAGGTGAGCCCACTCA (Sequence ID No.: 27); probe: 5'-GTGGTGGGGCATATG GTTTA (Sequence ID No.: 28).

Results are shown in FIG. 10 for 1 of 4 similar experiments.

Remaining cultures were incubated for a further 5 days and used to determine proliferative responses as described in Example 3.

Patient cells proliferated in response to BSA (6740±480 cpm) and Herpes antigen (8100±730 cpm) but not to Tep69 (1360±190 cpm). Control cells proliferated only in response to Herpes antigen (7670±620 cpm).

Example 7

Groups of female NOD mice aged 5 weeks were injected subcutaneously with 150 µg BSA (Sigma) or 50 µg BSA-derived peptide 152–169 (ABBOS) (18 mice per treatment group); the protein or peptide for injection was suspended in incomplete Freund's Adjuvant. A control group (13 mice) was injected with incomplete Freund's Adjuvant only and a further control group (13 mice) was untreated. A booster injection of the same treatment material was given intraperitoneally one week later.

IDDM development was followed by testing for urine glucose and when urine glucose was detected, blood glucose was then determined.

IDDM, as defined by elevated blood and urine glucose levels, became detectable in the control group about 13 weeks and by 34 weeks, the control group showed an IDDM incidence of close to 70%, as seen in FIGS. 11 and 12. In contrast, treatment with BSA or ABBOS and adjuvant completely prevented the development of IDDM up to 9 months (FIG. 11).

Circulating IgG anti-BSA antibodies were measured over the 34 weeks of the experiment, using the particle concentration fluoroimmunoassay described by the inventors in International Patent Application No. PCT/CA93/000304.

As seen in Panel A of FIG. 12, mice treated with incomplete adjuvant showed little antibody response whereas BSA and ABBOS treated mice showed a massive antibody response.

Example 8

Groups of neonatal NOD mice (less than 30 hours old) were injected intraperitoneally with 50 µg Tep69, 50 µg ovalbumin (control) or vehicle alone.

By the age of 25 days, the sex of the animals was determined and male mice were removed from the experiment. All animals received normal rodent chow and were followed for 40 weeks to determine the appearance of overt IDDM (glucosuria, confirmed by blood glucose measurements). Results in control animals were similar and data were pooled.

The results are shown in FIG. 13. Neonatal administration of Tep69 completely prevented the development of IDDM in most treated animals and delayed disease expression in the remainder.

Example 9

Five week old NOD mice received one of the following treatments: a) Tep69, 50 µg subcutaneously (single injection) in incomplete adjuvant; b) incomplete adjuvant alone, single injection subcutaneously, followed a week later in half the animals by a single injection intraperitoneally. Results with these "adjuvant only" animals were the same and data were pooled; d) single subcutaneous injection of 50 µg ABBOS-short peptide in incomplete adjuvant; e) 50 µg ABBOS-short injected subcutaneously in incomplete adjuvant followed a week later by 50 µg ABBOS-short injected intraperitoneally in incomplete adjuvant. Animals were reared on normal rodent chow and followed for the development of overt diabetes.

The results are shown in FIG. 14. Immunisation with Tep69 in incomplete adjuvant accelerated the development of IDDM and raised its incidence significantly. Immunisation with ABBOS-short by subcutaneous injection followed by an intraperitoneal booster injection gave complete protection against IDDM development. A single subcutaneous injection of ABBOS-short gave less complete protection.

Immunisation with subcutaneous ABBOS-short followed by an intraperitoneal booster was accompanied by a large humoral antibody response, while a single ABBOS-short injection subcutaneously gave a lower humoral antibody response.

Example 10

Tissue samples: Fresh tissue from healthy 8–14 week old Wistar rats and 8–12 week old B10.GD mice fed ad libitum with standard lab chow was kept in liquid nitrogen until analysis. Fetal tissue was obtained from B10.GD mice at day 18 of gestation. Mouse and rat islets were isolated from fresh pancreas by a standard collagenase method with an enrichment of >90% islet cells. Human tissue samples were obtained <2 h post mortem or from individuals undergoing organ resection for medical indications. Human pancreas (kind gift of Dr. J. Karjalainen, Oulu, Finland) was obtained from an adult organ donor. Human pancreatic islets (kind gift of Dr. R. Rajotte, Edmonton, Alberta) were isolated from an adult organ donor pancreas by the collagenase digestion procedure and cultured in RPMI medium containing 10 mM glucose for 72 h. The NOD mouse NIT beta cell line (kind gift of Dr. B. Singh, London, Ontar), the rat insulinoma cell line (RIN) and the human liver cell line Hep G were cultured containing 10 mM glucose.

RNA and cDNA preparation: Total RNA was extracted using a modified acid guanidinium isothiocyanate method (3). Frozen human pancreas and thyroid as well as all rodent tissues (except islet) were mechanically pulverized at −100° C. and instantly transferred to lysis buffer. Pancreatic islets and cell lines were directly resuspended in lysis buffer. RNA from human brain, muscle, lung and testis (kind gift of Dr. J. Rommens, Hospital for Sick Children, Toronto) was isolated by guanidinium—CsCl gradient preparation (4). For poly(A) $^+$RNA isolation, latex beads carrying oligo(dC$_{10}$)-dT$_{30}$) were used as described (5).

The inventors have recently developed a procedure for the quantitation of mRNA gene transcripts by template-calibrated RT-PCR (6). Briefly, approximately 3 μg total RNA was reverse transcribed using oligo(dT) $_{12-18}$ Pharmacia Ltd., Montreal, Que.) and MMLV reverse transcriptase (Gibco BRL, Mississauga, Ont.). Oligo(dT) primed cDNA was calibrated by radionuclide incorporation. This provides template calibration despite tissue-dependent differences in RNA quality, RNA quantity as well as varying reverse transcription efficiency, all major sources of template variation in RT-PCR. Thus, identical amounts of cDNA were used for subsequent PCR. The average coefficient of variation (CV) for cDNA synthesis was 12.9%.

Calibrated RT-PCR Quantitation: Calibrated cDNA was amplified by the polymerase chain reaction (PCR) using fluorescein amidate labelled p69 primers (69.1 and 69.2, 28 cycles, T$_{anneal}$ 55° C.) or β-glucuronidase primers (β-gluc1 and β-gluc2, 29 cycles, T$_{anneal}$ 55° C.) (Table 1) and standard amplification conditions as described (6). Primers were identical for all three species, and they were located on different exons spanning one or more introns to detect the possible amplification of contaminating genomic DNA. A fluorescent 439 bp human PCR product (Rat 435 bp, mouse 433 bp) for p69 and a 302 bp product (all species) for β-glucuronidase was thus generated.

PCR products were quantitated on an automated DNA sequences (A.L.F.™, Pharmacia) by laser-induced fluorescence after separation on a 6% polyacrylamide/7M urea gel (6). Distinct fluorescence peaks with a specific run-time characteristic for each PCR product were analyzed with FragmentManager™ software (Pharmacia). The area under the curve of each peak was expressed in relative fluorescence units (RFU). Values described in the text represent the mean of three PCT amplifications. To account for stochastic variability in PCR amplification (intra-assay CV: 10.6%), reactions were performed in triplicate and samples to be compared were amplified in parallel. The intra-assay (lane-to-lane) coefficient of variation for the quantitation of identical samples averaged 5.33%.

Southern Blots: To confirm specificity, PCR products were blotted onto nylon membrane (Hybond N plus, Amersham) after agarose gel electrophoresis and hybridized with [α-$^{32}$P]dATP end-labelled oligonucleotides (T4 polynucleotide kinase, Pharmacia). Blots were washed at high stringency (final wash 10 min at 55° C., 1×SSC/0.1% SDS) and exposed to X-ray film. p69 PCR products were hybridized with species specific internal oligoprobes (Table 2). To probe β-glucuronidase products a common internal oligonucleotide was used (Table 2).

Northern Blot Analysis: 2 μg poly(A)$^+$ RNA from various adult mouse tissues was separated on formaldehyde 1.2% agarose gels, blotted onto nylon membrane (Hybond N plus, Amersham) and hybridized with a radiolabelled 1.4 kb p69 cDNA probe or 2.0 kb β-actin cDNA probe. Blots were washed at 65° C. in 0.5×SSPE/0.1% SDS final concentration and autoradiographed for 24 h.

Immunoblots: Mouse or human tissue samples were snap frozen in liquid nitrogen, mechanically disrupted with a single-use tissue homogenizer (Pellet Pestle™, BDH Inc.) and sonicated. After centrifugation to remove cell debris, total protein in the supernatant was determined using the BioRad™ assay according to the manufacturer (BioRad, Mississauga, Ont.). Equal amounts of protein were diluted in buffer containing SDS (2%) and mercaptoethanol (150 mM), and denatured for 3 min at 94° C. Protein (5 μg/lane) was separated on an 8% SDS-polyacrylamide gel and electroblotted onto nitrocellulose membranes (Hybond C plus, Amersham, Mississauga, Ont.). Rainbows marker proteins (Amersham) were included in every gel. The presence of similar amounts of protein in each lane was further ascertained in silver-stained gels performed in parallel.

Membranes were blocked overnight in TBS-Tween 1% (10 mM Tris, pH 7.5, 150 mM NaCl, 1% Tween 20). Rabbit anti-p69 antiserum (5') (diluted 1:5000) was applied for 3 h at 20° C. Membranes were washed 60 min with TBS-Tween 1% prior to addition of horseradish peroxidase-conjugated anti-rabbit IgG (BSA0free, diluted 1:15000; BioCan, Mississauga, Ont.). After 60 min incubation, membranes were washed as above and enhanced chemiluminescence was developed using the ECL Western blotting detection kit according to the manufacturer (Amersham).

RT-PCR characteristics: Logarithmic amplification kinetics, a prerequisite for PCR quantitation, were established for RT-PCR amplification of p69 mRNA (FIG. 22). 0.5 μl rat kidney cDNA was PCR amplified, aliquots were taken after 17 to 35 cycles, and the PCR product was quantitated by laser-induced fluorescence. No product was detectable after 17 cycles. For p69 cDNA (primers 69.1 and 69.2, Tab. 1) there was an exponential increment (1.9$^n$; n=Δ cycle number) of PCR product between cycle 24 and 29, with decreasing amplification efficiency after 30–32 amplification cycles as the plateau phase was approached. Optimized logarithmic PCR kinetics have been described previously for β-glucuronidase primers (6). Thus, PCR quantitation of both gene transcripts was carried out in the desired exponential phase of amplification to maintain a linear, quantitative relationship between template and PCR product.

p69 mRNA Expression: p69 mRNA levels in various human, mouse and rat tissues were determined by quantitative RT-PCR and fluorescence analysis of PCR products. In mouse and rat (FIG. 23), p69 gene expression peaks in testis and pancreatic islets, followed by brain, thyroid (mouse) and lung (rat). The highest levels of p69 mRNA transcripts were found in both islet cell lines (RIN and NIT). In contrast, the human hepatoma cell line Hep G2 was completely negative (FIG. 24). Low to very low levels of p69 mRNA were observed in adrenal, heart, ovary, kidney, pancreas, muscle and liver. Using this sensitive PCR approach, p69 mRNA was detectable in all analyzed solid rodent tissues. Great differences (well above 100-fold) are, however, evident between high and low level tissues.

Northern blot analysis confirmed high p69 expression levels in mouse testis and brain (FIG. 25) with a transcript size of ~2.0 kb. A second band (~1.7 kb) is visible in testis, compatible with a shorter p69 isoform transcript. Due to the lower sensitivity of Northern analysis, no specific p69 mRNA bands are detectable in most organs. Integrity of poly(A) $^+$RNA was confirmed by hybridization with a β-actin cDNA probe, giving a characteristic 2.2 kb band in all tissues, with an additional isoform (1.7 kb) in heart and muscle.

In humans, p69 mRNA peak levels were observed in brain and islets (FIG. 23). Intermediate to low expression was found in thyroid, lung and testis, and very low p69 mRNA levels were detected in muscle and pancreas. As in rodents, none of the human tissues was completely negative for p69 by RT-PCR analysis. β-glucuronidase (7) was studied in parallel as an internal control gene. mRNA levels of this housekeeping gene show a relatively narrow range of expression levels in all species and tissues, except in liver and pancreas (FIG. 23). When p69 mRNA levels were expressed as a function of β-glucuronidase mRNA levels in a given tissue, the emerging pattern of p69 gene expression was similar to the one found by analyzing p69 mRNA alone. This validated the PCR strategy.

p69 mRNA levels were directly compared in tissue from fetal (18 days of gestation) and adult mice (FIG. 26). p69 mRNA was detectable in fetal brain, heart, liver and pancreas, and p69 expression levels and patterns are similar to those in adult tissue. Southern blot hybridization using internal oligonucleotides confirmed the specificity of human (439 bp), mouse (433 bp) and rat (436 bp) PCR products for p69 as well as for β-glucuronidase (302 bp) (data not shown). We did not observe positive signals in any of the reagent blanks interspersed in all amplification and detection series.

p69 Protein Expression: Western blot analysis of human and mouse tissues was performed using a polyclonal antiserum raised against a C-terminal p69 peptide (8), where human, rat and mouse p69 sequences are identical and show no homology to BSA (2). Reactivity of these antibodies with recombinant p69 has previously been established (8).

When Western blots were probed with these antibodies, a sharp and single band was visible in the 69 kD range. As with transcript levels, high concentrations of p69 protein were detected in murine beta cells (NIT cell line). Immunoreactivity in human tissues is most prominent in brain, followed by ovary, heart, thyroid and liver (FIG. 27a). In the mouse, p69 immunoreactivity is detectable in brain, pancreas and testis (FIG. 27b). As in the Northern blot analysis, a smaller second band is visible in mouse testis, suggesting the presence of a smaller p69 isoform. The rabbit control serum collected before peptide immunization did not show any reactivity with p69. As expected, no cross-reactivity with BSA (used as a 69 kD size marker) was found (data not shown).

Example 11
cloning of murine p69 cDNA

Total RNA was prepared from whole brain of a 12 week old male NOD mouse, from the NIT pancreatic beta cell line (9) and from purified islets of young male Balb/c mice, using a modified guanidinium isothiocyanate method (3). Poly (A)+RNA was isolated with oligo(dT)30 latex particles (Oligotex-dT, Qiagen, Chatsworth, Calif.) (5). cDNA libraries were constructed from brain and NIT mRNA with the Uni-ZAP XR cloning vector kit (Stratagene, La Jolla, Calif.) according to the manufacturer's instructions. 7–8×10$^5$ recombinant phage were screened with a 320 bp p69 cDNA fragment from the 5' untranslated (127 bp) and coding-region of the rat p69 (2). Several positive clones were identified, plaque purified and the 1.6–2.1 kb inserts were in vivo excised and circularized in XL1-blue E.coli with R408 helper phage. Insert DNA from plasmid preparations of transfected E. coli was sequenced by dideoxy chain termination (Ampli Taqtm Cycle Sequencing Kit, Perkin Elmer) with an automated DNA sequencer (ALFtm, Pharmacia Ltd., Montreal., Que.) or manually, after $^{32}$P incorporation. The p69 coding region expressed in purified islets from Balb/c mice (Balb/c) mice was amplified by RT-PCR from cytosolic RNA, using the following primers: p69-49 (sense) 5'-GCTCAAG ATAAGTCAGTTGTCAA and p69-1452 (antisense) 5'-TCATGCATTGAGCA ATTCGTG. The purified 1.4 kb PCR product was cloned into pCR™ 1000 (Invitrogen, San Diego, Calif.) and sequenced.

PCR analysis of p69 isoforms

Total RNA from various mouse and human tissues was reverse transcribed using oligo(dt) $_{12-18}$ (Pharmacia) and MMLV reverse transcriptase (Gibco BRL, Mississauga, Ont.) (6). cDNA was amplified by PCR over 35 cycles, with p69 primers (p69-803 (sense) 5'GCTTACAAGACCCCATGAAG, p69-1120 (antisense) 5' TCAACAGCAAGAGGTCATCC) located on exon 9 and 11 of the mouse p69 gene, respectively (Gaedigk, R., et al., in preparation). PCR products were separated on 3% NuSieve agarose gels, transferred to nylon membranes (Hybond N$^+$, Amersham) by capillary blotting and hybridized with a [$^{32}$P]ATP end-labelled internal p69 oligonucleotide probe (p69-1044 5' CGAGGAAGCGTGCCTGGG), located on exon 11. Blots were washed at high stringency (1×SSC/0.1% SDS at 55° C. for 15 min) and autoradiographed. To confirm product specificity, both the 302 and 240 bp PCR product were purified (QIAEX, Qiagen, Chatsworth, Calif.), and the DNA was sequenced as described above.

Western blot of murine p69

Mouse and human tissue protein extracts were prepared as described in (6). After heat denaturation in buffer containing 1% SDS and mercaptoethanol, protein (5 μg/lane) was separated on 8% SDS-polyacrylamide gels and electroblotted onto nitrocellulose membrane (Hybond C$^{plus}$, Amersham, Mississauga, Ont.). Rainbow™ protein mix (Amersham) including a 69000 M$_r$ marker was used as size standard. Membranes were blocked overnight in TBS-Tween (10 mM Tris, pH 7.5, 150 mM NaCl, 1% Tween 20). Rabbit antiserum to recombinant human p69 (10) (diluted to 1:5000) was applied for 3 h at 20° C. Membranes were washed 60 min with TBS-Tween 1% prior to addition of horseradish peroxidase-conjugated goat anti-rabbit IgG (BSA-free, diluted 1:15000; BioCan, Mississauga, Ont.). After 60 min incubation, membranes were washed as above and enhanced chemiluminescence was developed using the ECL Western blotting detection kit (Amersham) according to the manufacturer.

Immunization and T cell proliferation assay

Male non-obese diabetic mice (NOD, 6–7 weeks old) were immunized with 50 μg BSA, ABBOS-short peptide (EFKADEKKFWGKYL), recombinant truncated p69 or p69 T cell epitope peptide 'Tep69' (AFIKATGKKEDE) (10). Recombinant truncated p69 was prepared by expression of a portion of the cDNA of IS4. The cDNA was cut a few nucleotides downstream of the 3' terminal of exon 3 and was subcloned into the PET™ expression system according to the manufacturer's recommendations (Novagen Inc., Madison, Wis.). The truncated protein contains 100 amino acids and is essentially identical with the murine molecule.

Antigens were injected subcutaneously in complete Freunds' adjuvant, and local lymph nodes and blood samples were collected 10 days later. Triplicate cultures of 2×10$^5$ lymph node cells were incubated for 5 days in serum-free HGM-af Medium™ (Promo Cell, Heidelberg, Germany) in the presence of 1 μg of protein or synthetic peptide as recall antigen. Six hours before harvesting, 1 μCi $^3$H-thymidine (6.7 Ci/mmol) was added to the wells, and isotope incorporation was analysed by liquid scintillation counting. Values are expressed as mean counts per minute ± standard deviation (mean cpm ± SD).

Fluoroimmunoassay

Serum antibodies to BSA and p69 were measured by particle concentration fluoroimmunoassay, as described (11). Briefly, 20 µl of test serum, diluted 1:30 to 1:300, was added to 96-well unidirectional-flow vacuum-filtration plates (IDEXX, Portland, Me.), each containing 20 µl microspheres previously covalently coupled with BSA or recombinant p69. After three minutes of incubation and two washing steps, unbound protein was removed by vacuum filtration and 20 µg of fluoresceinated, affinity purified goat anti-mouse IgG (BioCan, Mississauga, Ont.) was added to each well. Non-organic saline buffers containing 1% Tween-20 to block non-specific binding were used for washing and dilutions. Bound fluorescence was read by an automated ScreenMachine™ instrument (IDEXX, Portland, Me.). Data are expressed in kilofluorescence units relative to a standard mouse serum analyzed in parallel within each assay plate.

p69 cDNA

The screening strategy employed a probe from the very 5' region of the rat molecule for the screening of cDNA libraries. Several cDNA clones containing full length coding region sequences for p69 were obtained from the NOD mouse brain and NIT (beta cell) cDNA libraries. In addition, a near full length coding sequence was amplified from purified islets of Balb/c mice. Due to alternative RNA splicing, there was more then one cDNA pattern, but these different isoforms did not appear to be expressed in a tissue specific fashion (see below).

FIG. 19 provides a comparison between the deduced amino acid sequences of mouse and human p69 clones. Human clone IS10 is compared to three mouse brain-derived p69 clones (mB9, mB10, mB2A) and the PCR-generated mouse islet sequence. The two full length coding regions obtained from the NIT cDNA library were identical to mB9 and their sequences are not provided.

When compared to the human molecule, mouse p69 is highly conserved. Four domains can be distinguished on the basis of protein sequence conservation (FIG. 20). Following a small (16 residues) N-terminal region with 25% divergence between man and mouse (Domain A), there is a large (288 aa) region with only a single amino acid change (C⇒Y, 99.6% identity, Domain B). This is followed by a stretch of 145 residues that show 33% divergence from the human molecule, with 47% base changes at the cDNA level (Domain C). The 66 residue C-terminal domain shows 100% identity with the human sequence (Domain D). In both the conserved domains there are 26% silent base changes, documenting the considerable pressure to maintain the primary amino acid structure of the molecule. It is most likely that these domains represent distinct functional regions in the p69 protein.

Human p69 has three regions of homology with bovine serum albumin (BSA). As shown in FIG. 19 (black bars), the Tep69 sequence is conserved in all p69 clones now available from human or rodent tissues. The second BSA homology region is also fully conserved, while there is one amino acid deleted in the most C-terminal homology region in Domain C. Mouse p69 thus meets the same structural criteria for possible mimicry with BSA as the human molecule.

All p69 cDNA clones show alternative RNA processing patterns in 5'-untranslated and/or coding regions. The mouse mB2A clone eliminates 22 amino acids in domain C, a region that corresponds to the complete exon 10 in genomic DNA (Gaedigk, R., et al., in preparation).

Extensive alternative splicing is found in the 5'-untranslated region of p69. FIG. 21 compares 5'-untranslated regions in clones of sufficient length. The longest 5'-untranslated cDNA fragment isolated so far was derived from a rat islet cDNA library (2). Sequence line up (FIG. 21) suggests that two of the new mouse clones have an identical 5'-end derived from sequences upstream of, but overlapping with, this rat sequence. The 5'-region of human, mouse and rat cDNA's contains an area of about 50 bp that is highly conserved among these species. A second conserved area lies upstream of the common translation start site and all mouse and human clones connect to this conserved 5'-untranslated region, albeit through alternative patterns of differential RNA splicing (FIG. 21).

Expression of p69 isoforms

As outlined above, the inventor cloned and identified from a NOD mouse brain cDNA library a short p69 transcript lacking exon 9 (63 nucleotides) in domain C. The tissue specificity and relative expression of both isoforms was studied by RT-PCR. cDNA's from various mouse tissues were amplified using primers flanking the alternatively spliced exon 9. Interference with genomic DNA was avoided by localization of primers p69-803 and p69-1120 on exons 8 and 11, respectively.

As shown in FIG. 28a, two PCR products (317 bp and 254 bp) were generated, arising from the long and short p69 transcript, respectively. Both transcript isoforms were detectable by PCR in brain, testis and the NIT islet cell line and at very low levels in liver and pancreas. Specificity of PCR products was established by Southern blotting and probing with an internal oligonucleotide (p69-1044) located on exon 10 that is common to both isoforms (FIG. 28b).

In addition, both PCR products were eluted from the gel, purified and sequenced. FIG. 29 shows that in the shorter p69 isoform, exon 8 is spliced in frame to exon 10. In contrast, in the 317 bp product amplified from the longer p69 transcript, exon 8 sequence is followed by exon 9 (FIG. 29), which is in frame spliced to exon 10. These data confirm the coexpression of alternatively spliced p69 mRNA in these tissues through skipping of exon 9.

To study the expression of p69 isoforms on the protein level, various mouse tissue homogenates were analysed by immunoblotting after SDS polyacrylamide electrophoresis, using a polyclonal antibody raised against recombinant p69. As demonstrated in FIG. 30, p69 protein expression generally parallels p69 transcript expression. In brain, testis, pancreas and the NIT islet cell line, p69 immunoreactivity is visible as a double band in the 69 kD range. The detection of two p69 immunoreactive bands with only subtle size differences is compatible with the expression of two murine p69 protein isoforms in vivo.

Murine immune repertoires for p69 and BSA

Young male NOD mice ($H2^{G7}$, $IE^{-/-}$) received a single immunization with truncated p69 (as encoded by IS4 cDNA) in complete adjuvant, and antibody and T cell proliferative responses were measured 8–10 days later. MHC disparate C57/B6 ($H2^b$, $IE^{-/-}$) and SJL ($H2^s$, $IE^{-/-}$) mice served as non-diabetes prone controls (FIG. 31).

A second set of mice received ovalbumin as antigen. Vigorous p69-specific antibody and T cell responses were observed in immunized NOD mice but not in C57/B6 or SJL strains. Notably, the NOD responses were of the same order of magnitude as responses to a bona fide non-self antigen, ovalbumin. Both control strains of mice generated comparable responses to ovalbumin. Thus, NOD mice possess and can readily recruit sizable B- and T cell repertoires recognizing the p69 self antigen, a property not found in mice that do not develop autoimmune diabetes.

To determine if the epitopes delineated as the main, perhaps exclusively diabetes-associated, epitopes in diabetic children were also recognized by NOD mice. NOD mice were immunised as before with either recombinant truncated p69 or with Tep69 peptide. As shown in FIG. 32, NOD mice again showed vigorous B- and T cell responses to immunization with the recombinant molecule. p69 induced T cell responses could be recalled in vitro by Tep69 peptide and immunization with Tep69 generated similar T cell responses to in vitro stimulation with the peptide or p69. However, Tep69 immunized animals did not develop significant anti-p69 antibody levels, suggesting that this 12mer peptide does not include a complete B cell epitope. Consistent with the data of FIG. 31, essentially no responses were observed in C57/B6 animals immunized and/or stimulated with p69 or Tep69 peptide. Thus, Tep69 is presented in NOD mice and represents a major T- but not B-lymphocyte self-epitope in p69. Tep69 is not recognized by readily available immune repertoires of C57/B6 and SJL mice.

In a further series of studies, NOD mice and C57/B6 mice were immunised as described above with a single subcutaneous injection of either BSA or ABBOS-short peptide.

These mice generated vigorous B- and T cell responses, independent of their genetic background (FIG. 33). However, when responsive T cell were stimulated in vitro with ABBOS-short peptide, only NOD lymphocytes responded well, and they did so at a rate similar to that observed with BSA-stimulated cultures. Likewise, ABBOS-short immunised NOD mice generated the same T cell responses when stimulated in vitro with either ABBOS-short or BSA. In parallel, ABBOS-short immunised animals developed considerable anti-BSA antibody levels, albeit at somewhat lower levels than those observed in BSA immunised mice. Thus, the ABBOS-short peptide is effectively presented and constitutes a major BSA epitope recognised in NOD B- and T-cell responses.

In contrast, BSA-immunised C57/B6 mice showed only a poor T cell response to in vitro stimulation with ABBOS-short peptide, and, consistently, immunisation with ABBOS-short-elicited at best small responses to in vitro recall stimulation with either the peptide or full BSA (FIG. 33). Furthermore, ABBOS-short immunisation failed to trigger a significant anti-BSA antibody responses in these animals. Thus, ABBOS-short is at best a minor BSA epitope in non-diabetic mice.

Although only preferred embodiments of the present invention have been described, the present invention is not limited to the features of these embodiments, but includes all variations and modification within the scope of the claims.

TABLE 1

| Synthetic Peptide | aa-Position | Peptide Sequence | Sequence ID No. | Stimulation Index |
|---|---|---|---|---|
| BSA-derived peptides: | | | | |
| ABBOS | 152–169 | FKADEKKFWGKYLYEIAR | 11 | 7.86 |
| ABBOS-D | 152–169 | FKDDEKKFWGKYLYEIAR | 12 | 1.20 |
| ABBOS+ ABBOS-D | | | | 1.46 |
| P2268 | 152–169 | KFWGKYLYEIAR | 13 | 1.88 |
| C148 | 148–159 | LCDEFKADEKK | 14 | 4.74 |
| C150 | 150–162 | DEFKADEKKFWG | 15 | 3.27 |
| C151 | 151–161 | EFKADEKKFW | 16 | 3.31 |
| P2267 | 151–159 | EFKADEKK | 7 | 7.32 |
| C164 | homolog | EFKATGKK | 22 | 6.94 |
| CN-9 | 151-157 | EFKADE | 17 | 1.1 |
| CN-10 | 151-156 | EFKAD | 18 | 0.97 |
| CN-13 | 152-158 | FKADEK | 19 | 0.92 |
| CN-11 | 153-159 | KADEKK | 20 | 1.09 |
| CON-14 | 154-159 | ADEKK | 21 | 1.06 |
| p69-derived peptides | | | | |
| Tep69 | 36–47 | AFIKATGKKEDE | 23 | 7.98 |
| H-1026 | 48–65 | HVVASDADLDAKLELFHS | 24 | 1.08 |
| H-1044 | 105–116 | DKTRAGKMMQAT | 25 | 0.94 |
| H-1031 | 200–217 | LAKKNFDKLKMDVCQKVD | 26 | 0.98 |

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 1528 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATAATATAAC TTATCCTCTC ATGCTTTTTT CCTGCCCCTT CTCCCCAAAT CATCAACAAT      60

AGAAGAAGAA GAAAACATGT CAGGACACAA ATGCAGTTAT CCCTGGGACT ACAGGATCG      120

ATATGCTCAA GATAAGTCAG TTGTAAATAA GATGCAACAG AAATATTGGG AGACGAAGCA     180

GGCCTTTATT AAAGCCACAG GAAGAAGGA AGATGAACAT GTTGTTGCCT CTGACGCGGA      240

CCTGGATGCC AAGCTAGAGC TGTTTCATTC AATTCAGAGA ACCTGTCTGG ACTTATCGAA     300

AGCAATTGTA CTCTATCAAA AGGGGATATG TTTCTTGTCT CAAGAAGAAA ACGAACTGGG     360

AAAATTTCTT CGATCCCAAG GTTTCCAAGA TAAAACCAGA GCAGGAAAGA TGATGCAAGC     420

GACAGGAAAG GCCCTCTGCT TTTCTTCCCA GCAAAGGTTG GCCTTACGAA ATCCTTTGTG     480

TCGATTTCAC CAAGAAGTGG AGACTTTTCG GCATCGGGCC ATCTCAGATA CTTGGCTGAC     540

GGTGAACCGC ATGGAACAGT GCAGGACGGA ATATAGAGGA GCACTATTAT GGATGAAGGA     600

CGTGTCTCAG GAGCTTGATC CAGACCTCTA CAAGCAAATG GAGAAGTTCA GGAAGGTACA     660

AACACAAGTG CGCCTTGCAA AAAAAAACTT TGACAAATTG AAGATGGATG TTTGTCAAAA     720

AGTGGATCTT CTTGGAGCGA GCAGATGCAA TCTCTTGTCT CACATGCTAG CAACATACCA     780

GACCACTCTG CTTCATTTTT GGGAGAAAAC TTCTCACACT ATGGCAGCCA TCCATGAGAG     840

TTTCAAAGGT TATCAACCAT ATGAATTTAC TACTTTAAAG AGCTTACAAG ACCCTATGAA     900

AAAATTAGTT GAGAAAGAAG AGAAGAAGAA AATCAACCAG CAGGAAAGTA CAGATGCAGC     960

CGTGCAGGAG CCGAGCCAAT TAATTTCATT AGAGGAAGAA AACCAGCGCA AGGAATCCTC    1020

TAGTTTTAAG ACTGAAGATG GAAAAAGTAT TTTATCTGCC TTAGACAAAG GCTCTACACA    1080

TACTGCATGC TCAGGACCCA TAGATGAACT ATTAGACATG AAATCTGAGG AAGGTGCTTG    1140

CCTGGGACCA GTGGCAGGGA CCCCGGAACC TGAAGGTGCT GACAAAGATG ACCTGCTGCT    1200

GTTGAGTGAG ATCTTCAATG CTTCCTCCTT GGAAGAGGGC GAGTTCAGCA AGAGTGGGC    1260

CGCTGTGTTT GGAGACGGCC AAGTGAAGGA GCCAGTGCCC ACTATGGCCC TGGGAGAGCC    1320

AGACCCCAAG GCCCAGACAG GCTCAGGTTT CCTTCCTTCG CAGCTTTTAG ACCAAAATAT    1380

GAAAGACTTA CAGGCCTCGC TACAAGAACC TGCTAAGGCT GCCTCAGACC TGACTGCCTG    1440

GTTCAGCCTC TTCGCTGACC TCGACCCACT CTCAAATCCT GATGCTGTTG GGAAAACCGA    1500

TAAAGAACAC GAATTGCTCA ATGCATGA                                       1528
```

(2) INFORMATION FOR SEQ ID NO:2:

(i) SEQUENCE CHARACTERISTICS:
 (A) LENGTH: 483 amino acids
 (B) TYPE: amino acid
 (C) STRANDEDNESS: single
 (D) TOPOLOGY: linear (ii) MOLECULE TYPE: protein (xi) SEQUENCE DESCRIPTION: SEQ ID NO:2:

```
Met Ser Gly His Lys Cys Ser Tyr Pro Trp Asp Leu Gln Asp Arg Tyr
1               5                   10                  15

Ala Gln Asp Lys Ser Val Val Asn Lys Met Gln Gln Lys Tyr Trp Glu
            20                  25                  30

Thr Lys Gln Ala Phe Ile Lys Ala Thr Gly Lys Lys Glu Asp Glu His
        35                  40                  45

Val Val Ala Ser Asp Ala Asp Leu Asp Ala Lys Leu Glu Leu Phe His
    50                  55                  60
```

```
Ser Ile Gln Arg Thr Cys Leu Asp Leu Ser Lys Ala Ile Val Leu Tyr
 65                  70                  75                  80

Gln Lys Gly Ile Cys Phe Leu Ser Gln Glu Glu Asn Glu Leu Gly Lys
             85                  90                  95

Phe Leu Arg Ser Gln Gly Phe Gln Asp Lys Thr Arg Ala Gly Lys Met
            100                 105                 110

Met Gln Ala Thr Gly Lys Ala Leu Cys Phe Ser Ser Gln Gln Arg Leu
        115                 120                 125

Ala Leu Arg Asn Pro Leu Cys Arg Phe His Gln Glu Val Glu Thr Phe
    130                 135                 140

Arg His Arg Ala Ile Ser Asp Thr Trp Leu Thr Val Asn Arg Met Glu
145                 150                 155                 160

Gln Cys Arg Thr Glu Tyr Arg Gly Ala Leu Leu Trp Met Lys Asp Val
                165                 170                 175

Ser Gln Glu Leu Asp Pro Asp Leu Tyr Lys Gln Met Glu Lys Phe Arg
            180                 185                 190

Lys Val Gln Thr Gln Val Arg Leu Ala Lys Lys Asn Phe Asp Lys Leu
        195                 200                 205

Lys Met Asp Val Cys Gln Lys Val Asp Leu Leu Gly Ala Ser Arg Cys
    210                 215                 220

Asn Leu Leu Ser His Met Leu Ala Thr Tyr Gln Thr Thr Leu Leu His
225                 230                 235                 240

Phe Trp Glu Lys Thr Ser His Thr Met Ala Ala Ile His Glu Ser Phe
                245                 250                 255

Lys Gly Tyr Gln Pro Tyr Glu Phe Thr Thr Leu Lys Ser Leu Gln Asp
            260                 265                 270

Pro Met Lys Lys Leu Val Glu Lys Glu Lys Lys Ile Asn Gln
        275                 280                 285

Gln Glu Ser Thr Asp Ala Ala Val Gln Glu Pro Ser Gln Leu Ile Ser
    290                 295                 300

Leu Glu Glu Glu Asn Gln Arg Lys Glu Ser Ser Ser Phe Lys Thr Glu
305                 310                 315                 320

Asp Gly Lys Ser Ile Leu Ser Ala Leu Asp Lys Gly Ser Thr His Thr
                325                 330                 335

Ala Cys Ser Gly Pro Ile Asp Glu Leu Leu Asp Met Lys Ser Glu Glu
            340                 345                 350

Gly Ala Cys Leu Gly Pro Val Ala Gly Thr Pro Glu Pro Glu Gly Ala
        355                 360                 365

Asp Lys Asp Asp Leu Leu Leu Ser Glu Ile Phe Asn Ala Ser Ser
    370                 375                 380

Leu Glu Glu Gly Glu Phe Ser Lys Glu Trp Ala Ala Val Phe Gly Asp
385                 390                 395                 400

Gly Gln Val Lys Glu Pro Val Pro Thr Met Ala Leu Gly Glu Pro Asp
                405                 410                 415

Pro Lys Ala Gln Thr Gly Ser Gly Phe Leu Pro Ser Gln Leu Leu Asp
            420                 425                 430

Gln Asn Met Lys Asp Leu Gln Ala Ser Leu Gln Glu Pro Ala Lys Ala
        435                 440                 445

Ala Ser Asp Leu Thr Ala Trp Phe Ser Leu Phe Ala Asp Leu Asp Pro
    450                 455                 460

Leu Ser Asn Pro Asp Ala Val Gly Lys Thr Asp Lys Glu His Glu Leu
465                 470                 475                 480

Leu Asn Ala
```

(2) INFORMATION FOR SEQ ID NO:3:

(i) SEQUENCE CHARACTERISTICS:
        (A) LENGTH: 2107 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGCACGAGCT CCGATCTCCG CTGAGAGGCT CCTGGGGGCC GGGGCTCCGA GGAAAATGGT      60

TCGATGTTAT TAAAAATGAA TCTTAAGAAG AAAAATGAAT CACAGCAGTT AAACTATGGA     120

GTTCTGCTAC TTGTAAGAAG TGGAGAAGCC TGAGATTACA TCACTGACCC TTGATCCTCC     180

ACTGAGCTAA ACACCAGCT GGTAATTGCC TATGATTTTA TAGACTTCCC TCCATCTGCT      240

GGGTCCAAGT GTCCGTCTGA CTGCTCTGGT ACCGGAGCAT CTTTATTTCT GCATCTAAAC     300

TTGTAAAAAG CACATCGAAT CTTGTTCCCC AGGAGAAAAT CTTCAATGTA ACCATTTTCA     360

ATGTATCCGA TGATACAAGC GCATTGTAAT CTCCAGGTAG AAGCAGCTTT ATCAGTGGAA     420

AGGGTTTAAT AGAACATATC CTATCATGCT TTTTCTCTGC CCCTTCTCAA ATCATCAGCA     480

GTAGAAAAGA AAGAAAACA TGTCAGGACA CAAATGTTAT TCCTGGGAGT TGCAGGATCG      540

GTTTGCTCAA GATAAGTCAG TTGTCAATAA GATGCAACAG AAATATTGGG AAACGAAGCA     600

GGCCTTTATC AAAGCCACAG GGAAGAAGGA AGATGAACAT GTCGTTGCTT CTGATGCAGA     660

CCTGGATGCC AAGCTAGAGC TGTTTCATTC GATTCAGAGA ACCTGTTTGG ACTTGTCTAA     720

AGCAATTGTG CTCTATCAAA AGAGAATATG TTTCTTGTCT CAAGAAGAAA ATGAACTGGG     780

AAAATTTCTC CGATCCCAAG GCTTCCAGGA CAAAACCCGA GCAGGAAAAA TGATGCAAGC     840

CACAGGAAAG GCCCTCTGCT TTTCCTCCCA GCAAAGGTTG GCCTTGAGAA ACCCTTTGTG     900

TCGATTTCAC CAAGAAGTAG AGACTTTTAG ACATCGGGCC ATCTCCGATA CCTGGCTGAC     960

AGTGAACCGC ATGGAGCAGT GCCGGACAGA ATATAGAGGG GCGTTATTGT GGATGAAGGA    1020

CGTGTCTCAG GAACTGGATC CAGACCTCTA CAAGCAAATG GAGAAGTTCA GGAAGGTACA    1080

GACACAAGTC CGCCTCGCGA AGAAGAACTT TGACAAATTG AAGATGGATG TGTGTCAAAA    1140

GGTGGATCTT CTTGGAGCAA GCAGATGTAA CCTCTTATCT CACATGCTAG CAACATATCA    1200

GACCACTCTG CTCCACTTTT GGGAGAAAAC TTCTCACACC ATGGCAGCCA TCCATGAGAG    1260

CTTCAAAGGC TATCAACCAT ATGAATTCAC AACGTTAAAG AGCTTACAAG ACCCTATGAA    1320

AAAGCTAGTC GAGAAAGAAA AGAAGAAGAG CTCCCGGAGG GAAAACCGGG AGGCTGTGGC    1380

ACAGGAGCCG AGGCAGTTAA TTTCATTGGA GGAAGAGAAC CAGCACAAAG AATCCTCTAC    1440

TTGCCAGAAG GAGGAGGGAA AAAGCGTTCC GTCGTCTGTA GACAAGAGTT CTGCAGATGA    1500

TGCATGCTCA GGACCCATAG ATGAACTATT AGACGTGAAA CCTGAGGAAG CTTGCCTGGG    1560

TCCCATGGCA GGGACCCCAG AACCTGAAAG TGGGGACAAG GACGACCTCC TGCTGTTGAA    1620

CGAGATCTTC AGCACTTCCA GCCTGGATGA AGGGGAGTTC AGCAGGGAGT GGGCTGCGGT    1680

GTTCGGAGAC GACCGGCTGA AGGAACCAGC CCCCATGGGG GCCCAGGGAG AGCCAGACCC    1740

CAAGCCCCAG ATAGGCTCTG CGTTCCTTCC TTCACAGCTT TTAGACCAAA ACATGAAAGA    1800

TCTCCAGGCC TCTCTCCAAG AGCCTGCCAA GGCTGCCTCG GACCTGACTG CCTGGTTCAG    1860

CCTCTTTGCT GACCTCGACC CCCTATCAAA TCCTGATGCT ATTGGGAAAA CCGATAAAGA    1920

ACACGAATTG CTCAATGCAT GAGTCTGCAA CCTTCAACAG GGGAGCCCTC CGGCCACTCC    1980
```

```
GCAACACCTC ATCCAGGGCT TGCAGAAGTC TAACGTGCTC AGTACGCTGT TTTAATATTT      2040

ACATGCCATT TTAATAAAAC GAGAGGGTCA AGGCCCTGTT TCTATCGCTA TAAAAAAAAA      2100

AAAAAAA                                                                2107

(2) INFORMATION FOR SEQ ID NO:4:

(i) SEQUENCE CHARACTERISTICS:
        (A) LENGTH: 480 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Ser Gly His Lys Cys Tyr Ser Trp Glu Leu Gln Asp Arg Phe Ala
1               5                  10                  15

Gln Asp Lys Ser Val Val Asn Lys Met Gln Gln Lys Tyr Trp Glu Thr
            20                  25                  30

Lys Gln Ala Phe Ile Lys Ala Thr Gly Lys Lys Glu Asp Glu His Val
        35                  40                  45

Val Ala Ser Asp Ala Asp Leu Asp Ala Lys Leu Glu Leu Phe His Ser
    50                  55                  60

Ile Gln Arg Thr Cys Leu Asp Leu Ser Lys Ala Ile Val Leu Tyr Gln
65                  70                  75                  80

Lys Arg Ile Cys Phe Leu Ser Gln Glu Glu Asn Glu Leu Gly Lys Phe
                85                  90                  95

Leu Arg Ser Gln Gly Phe Gln Asp Lys Thr Arg Ala Gly Lys Met Met
            100                 105                 110

Gln Ala Thr Gly Lys Ala Leu Cys Phe Ser Ser Gln Gln Arg Leu Ala
        115                 120                 125

Leu Arg Asn Pro Leu Cys Arg Phe His Gln Glu Val Glu Thr Phe Arg
    130                 135                 140

His Arg Ala Ile Ser Asp Thr Trp Leu Thr Val Asn Arg Met Glu Gln
145                 150                 155                 160

Cys Arg Thr Glu Tyr Arg Gly Ala Leu Leu Trp Met Lys Asp Val Ser
                165                 170                 175

Gln Glu Leu Asp Pro Asp Leu Tyr Lys Gln Met Glu Lys Phe Arg Lys
            180                 185                 190

Val Gln Thr Gln Val Arg Leu Ala Lys Lys Asn Phe Asp Lys Leu Lys
        195                 200                 205

Met Asp Val Cys Gln Lys Val Asp Leu Leu Gly Ala Ser Arg Cys Asn
    210                 215                 220

Leu Leu Ser His Met Leu Ala Thr Tyr Gln Thr Thr Leu Leu His Phe
225                 230                 235                 240

Trp Glu Lys Thr Ser His Thr Met Ala Ala Ile His Glu Ser Phe Lys
                245                 250                 255

Gly Tyr Gln Pro Tyr Glu Phe Thr Thr Leu Lys Ser Leu Gln Asp Pro
            260                 265                 270

Met Lys Lys Leu Val Glu Lys Glu Lys Lys Ser Ser Arg Arg Glu
        275                 280                 285

Asn Arg Glu Ala Val Ala Gln Glu Pro Arg Gln Leu Ile Ser Leu Glu
    290                 295                 300

Glu Glu Asn Gln His Lys Glu Ser Ser Thr Cys Gln Lys Glu Glu Gly
305                 310                 315                 320
```

```
Lys Ser Val Pro Ser Ser Val Asp Lys Ser Ser Ala Asp Asp Ala Cys
              325                 330                 335

Ser Gly Pro Ile Asp Glu Leu Leu Asp Val Lys Pro Glu Glu Ala Cys
              340                 345                 350

Leu Gly Pro Met Ala Gly Thr Pro Glu Pro Glu Ser Gly Asp Lys Asp
              355                 360                 365

Asp Leu Leu Leu Asn Glu Ile Phe Ser Thr Ser Ser Leu Asp Glu
              370                 375                 380

Gly Glu Phe Ser Arg Glu Trp Ala Ala Val Phe Gly Asp Asp Arg Leu
385                 390                 395                 400

Lys Glu Pro Ala Pro Met Gly Ala Gln Gly Glu Pro Asp Pro Lys Pro
              405                 410                 415

Gln Ile Gly Ser Ala Phe Leu Pro Ser Gln Leu Leu Asp Gln Asn Met
              420                 425                 430

Lys Asp Leu Gln Ala Ser Leu Gln Glu Pro Ala Lys Ala Ala Ser Asp
              435                 440                 445

Leu Thr Ala Trp Phe Ser Leu Phe Ala Asp Leu Asp Pro Leu Ser Asn
              450                 455                 460

Pro Asp Ala Ile Gly Lys Thr Asp Lys Glu His Glu Leu Leu Asn Ala
465                 470                 475                 480

(2) INFORMATION FOR SEQ ID NO:5:

(i) SEQUENCE CHARACTERISTICS:
        (A) LENGTH: 1386 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CAGTTATTCC TGGGAGTTGC AGGACCGGTT TGCTCAACAT AAGTCAGTTG TCAATAAGAT      60

GCAGCAGAAA TATTGGGAGA CCAAGCAGGC CTTTATCAAA GCCACGGGGA AGAAGGAAGA     120

TGAACATGTG GTTGCTTCTG ATGCAGACCT GGATGCCAAG CTGGAGCTGT TCACTCAAT     180

CCAGAGAACC TGTCTGGACT TGTCTAAAGC AATCGTGCTC TATCAAAAGA GAATATGTTT    240

CTTGTCTCAA GAGGAAAATG AACTGGGAAA GTTTCTTCGA TCTCAAGGCT TCCAAGACAA    300

AACCCGAGCA GGAAAAATGA TGCAAGCCAC CGGCAAGGCC CTCTGCTTTT CCTCCCAGCA    360

AAGGTTGGCC TTGAGAAACC CTTTGTGTCG ATTTCACCAA GAAGTAGAAA CTGTTAGACA    420

TCGGGCCATC TCTGATACCT GGCTGACAGT GAACCGCATG GAGCAGTACA GGACAGAATA    480

CAGAGGAGCG TTGTTATGGA TGAAGGACGT GTCTCAGGAA CTTGATCCAG ACCTCTACAA    540

GCAAATGGAG AAGTTCAGGA AGGTGCAGAC ACAAGTCCGC CTTGCGAAGA GAACTTTGA    600

CAAGTTGAAG ATGGATGTGT GTCAAAAGGT GGATCTTCTT GGAGCAAGCA GATGTAACCT    660

CTTATCTCAC ATGCTAGCAA CATACCAGAC CACTCTGCTC CATTTTTGGG AGAAAACTTC    720

TCACACCATG GAGCATTCAT GAGAGTTAAA GGTTATCAAC CATATGAATT CACAACGTTA    780

AAGAGCTTAC AAGACCCCAT GAAGAAGCTA GTTGAGAAGG AAGGGAAGAA GACCTCCTCG    840

AGGGAAAACC GGGAGGCTGT GGCACCAGAG CCGAGGCAGT TAATTTCTTT GGAGGATGAG    900

AACCAGCACA AAGATTCATC TACTTATAAG ACTGAGGAGG GACAAAGCGT TTTGTCTTCC    960

GTAGACAAAG GTTCTGTACA TGACACATGC TCAGGACCCA TAGATGAACT ATTAGACGGG   1020

AAACCCGAGG AAGCGTGCCT GGGTCCCATG GCAGGGACCC CAGAACCTGA AAGTGGGGAC   1080
```

-continued

```
AAGGATGACC TCTTGCTGTT GAATGAGATC TTCACTTCCA GCCTGGAAGA AGGGGAGTTC    1140

AGCAGAGAGT GGGCTGCAGT GTTTGGAGAT GACCGGCTAA AGGAGCCAGC CCCCATGGGG    1200

GCCCAAGGAG AGCCAGACCC CAAGCCCCAG ATAGGCTCCG GATTCCTTCC GTCGCAGCTT    1260

TTAGACCAAA ATATGAAAGA CTCCAGGCC TCTCTGCAAG AGCCTGCCAA GGCTGCCTCG     1320

GACCTGACTG CCTGGTTCAG CCTCTTTGCT GACCTCGACC CCTTATCAAA CCCTGATGCT    1380

GTTGGG                                                                1386
```

(2) INFORMATION FOR SEQ ID NO:6:

(i) SEQUENCE CHARACTERISTICS:
        (A) LENGTH: 463 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Ser Tyr Ser Trp Glu Leu Gln Asp Arg Phe Ala Gln His Lys Ser Val
1               5                   10                  15

Val Asn Lys Met Gln Gln Lys Tyr Trp Glu Thr Lys Gln Ala Phe Ile
            20                  25                  30

Lys Ala Thr Gly Lys Lys Glu Asp Glu His Val Val Ala Ser Asp Ala
        35                  40                  45

Asp Leu Asp Ala Lys Leu Glu Leu Phe His Ser Ile Gln Arg Thr Cys
    50                  55                  60

Leu Asp Leu Ser Lys Ala Ile Val Leu Tyr Gln Lys Arg Ile Cys Phe
65                  70                  75                  80

Leu Ser Gln Glu Glu Asn Glu Leu Gly Lys Phe Leu Arg Ser Gln Gly
                85                  90                  95

Phe Gln Asp Lys Thr Arg Ala Gly Lys Met Met Gln Ala Thr Gly Lys
            100                 105                 110

Ala Leu Cys Phe Ser Ser Gln Arg Leu Ala Leu Arg Asn Pro Leu
        115                 120                 125

Cys Arg Phe His Gln Glu Val Glu Thr Val Arg His Arg Ala Ile Ser
    130                 135                 140

Asp Thr Trp Leu Thr Val Asn Arg Met Glu Gln Tyr Arg Thr Glu Tyr
145                 150                 155                 160

Arg Gly Ala Leu Leu Trp Met Lys Asp Val Ser Gln Glu Leu Asp Pro
                165                 170                 175

Asp Leu Tyr Lys Gln Met Glu Lys Phe Arg Lys Val Gln Thr Gln Val
            180                 185                 190

Arg Leu Ala Lys Lys Asn Phe Asp Lys Leu Lys Met Asp Val Cys Gln
        195                 200                 205

Lys Val Asp Leu Leu Gly Ala Ser Arg Cys Asn Leu Leu Ser His Met
    210                 215                 220

Leu Ala Thr Tyr Gln Thr Thr Leu Leu His Phe Trp Glu Lys Thr Ser
225                 230                 235                 240

His Thr Met Xaa Xaa Ile His Glu Ser Xaa Lys Gly Tyr Gln Pro Tyr
                245                 250                 255

Glu Phe Thr Thr Leu Lys Ser Leu Gln Asp Pro Met Lys Lys Leu Val
            260                 265                 270

Glu Lys Glu Gly Lys Lys Thr Ser Ser Arg Glu Asn Arg Glu Ala Val
        275                 280                 285
```

```
Ala Pro Glu Pro Arg Gln Leu Ile Ser Leu Glu Asp Glu Asn Gln His
    290                 295                 300

Lys Asp Ser Ser Thr Tyr Lys Thr Glu Glu Gly Gln Ser Val Leu Ser
305                 310                 315                 320

Ser Val Asp Lys Gly Ser Val His Asp Thr Cys Ser Gly Pro Ile Asp
                325                 330                 335

Glu Leu Leu Asp Gly Lys Pro Glu Glu Ala Cys Leu Gly Pro Met Ala
                340                 345                 350

Gly Thr Pro Glu Pro Glu Ser Gly Asp Lys Asp Asp Leu Leu Leu Leu
                355                 360                 365

Asn Glu Ile Phe Thr Ser Ser Leu Glu Glu Gly Glu Phe Ser Arg Glu
370                 375                 380

Trp Ala Ala Val Phe Gly Asp Asp Arg Leu Lys Glu Pro Ala Pro Met
385                 390                 395                 400

Gly Ala Gln Gly Glu Pro Asp Pro Lys Pro Gln Ile Gly Ser Gly Phe
                405                 410                 415

Leu Pro Ser Gln Leu Leu Asp Gln Asn Met Lys Asp Leu Gln Ala Ser
                420                 425                 430

Leu Gln Glu Pro Ala Lys Ala Ala Ser Asp Leu Thr Ala Trp Phe Ser
                435                 440                 445

Leu Phe Ala Asp Leu Asp Pro Leu Ser Asn Pro Asp Ala Val Gly
450                 455                 460
```

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Glu Phe Lys Ala Asp Glu Lys Lys
1               5
```

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ile Glu Thr Met Arg Glu Lys Val Leu Thr
1               5                   10
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Lys Leu Lys Pro Asp Pro Asn Thr Leu Cys Asp Glu
1               5                   10
```

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Tyr Ala Asn Lys Tyr Asn Gly Val Phe Gln Glu
1               5                   10
```

(2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Phe Lys Ala Asp Glu Lys Lys Phe Trp Gly Lys Tyr Leu Tyr Glu Ile
1               5                   10                  15
Ala Arg
```

(2) INFORMATION FOR SEQ ID NO:12:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Phe Lys Asp Asp Glu Lys Lys Phe Trp Gly Lys Tyr Leu Tyr Glu Ile
1               5                   10                  15
Ala Arg
```

(2) INFORMATION FOR SEQ ID NO:13:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Lys Phe Trp Gly Lys Tyr Leu Tyr Glu Ile Ala Arg
1               5                   10
```

(2) INFORMATION FOR SEQ ID NO:14:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Leu Cys Asp Glu Phe Lys Ala Asp Glu Lys Lys
1               5                   10
```

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Asp Glu Phe Lys Ala Asp Glu Lys Lys Phe Trp Gly
1               5                   10
```

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Glu Phe Lys Ala Asp Glu Lys Lys Phe Trp
1               5                   10
```

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Glu Phe Lys Ala Asp Glu
1               5
```

(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Glu Phe Lys Ala Asp
1               5
```

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single

```
            (D) TOPOLOGY: linear (ii) MOLECULE TYPE: peptide (xi) SEQUENCE DESCRIPTION: SEQ ID NO:19:

Phe Lys Ala Asp Glu Lys
1               5

(2) INFORMATION FOR SEQ ID NO:20:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:20:

Lys Ala Asp Glu Lys Lys
1               5

(2) INFORMATION FOR SEQ ID NO:21:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:21:

Ala Asp Glu Lys Lys
1               5

(2) INFORMATION FOR SEQ ID NO:22:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:22:

Glu Phe Lys Ala Thr Gly Lys Lys
1               5

(2) INFORMATION FOR SEQ ID NO:23:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:23:

Ala Phe Ile Lys Ala Thr Gly Lys Lys Glu Asp Glu
1               5                   10

(2) INFORMATION FOR SEQ ID NO:24:

(i) SEQUENCE CHARACTERISTICS:
         (A) LENGTH: 18 amino acids
         (B) TYPE: amino acid
```

(C) STRANDEDNESS: single
                (D) TOPOLOGY: linear (ii) MOLECULE TYPE: peptide (xi) SEQUENCE DESCRIPTION: SEQ ID NO:24:

His Val Val Ala Ser Asp Ala Asp Leu Asp Ala Lys Leu Glu Leu Phe
1               5                  10                  15

His Ser (2) INFORMATION FOR SEQ ID NO:25:

(i) SEQUENCE CHARACTERISTICS:
                (A) LENGTH: 12 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:25:

Asp Lys Thr Arg Ala Gly Lys Met Met Gln Ala Thr
1               5                  10

(2) INFORMATION FOR SEQ ID NO:26:

(i) SEQUENCE CHARACTERISTICS:
                (A) LENGTH: 18 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:26:

Leu Ala Lys Lys Asn Phe Asp Lys Leu Lys Met Asp Val Cys Gln Lys
1               5                  10                  15

Val Asp (2) INFORMATION FOR SEQ ID NO:27:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (xi) SEQUENCE DESCRIPTION: SEQ ID NO:27:

GGTGCCTGGC TGCCAGGCAG A                                            21

(2) INFORMATION FOR SEQ ID NO:28:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO:28:

CCAGGTGAGC CCACTCA                                                 17

(2) INFORMATION FOR SEQ ID NO: 29:

(i) SEQUENCE CHARACTERISTICS:
                (A) LENGTH: 1738 base pairs
                (B) TYPE: nucleic acid
                (C) STRANDEDNESS: single (D) TOPOLOGY: linear (ii) MOLECULE TYPE: cDNA (xi) SEQUENCE DESCRIPTION: SEQ ID NO: 29:

| | | | | | |
|---|---|---|---|---|---|
| GAGAGAGAGC | TCGTGCCGAA | TTCGGCACGA | GCTCCGCCGG | GAACCTCCTG | GGGGCCGGAG | 60 |
| CACCAAGGTT | TAATATAACT | TATCCTCTCA | TGATTTTTTC | CTGCCCCTTC | TCAAATCATC | 120 |
| GGCAATAGAA | AAGAGAAGAA | AACATGTCAG | GACACAAATG | TTATTCCTGG | GAGTTGCAGG | 180 |
| ACCGGTTTGC | TCAAGATAAG | TCAGTTGTCA | ATAAGATGCA | GCAGAAATAT | TGGGAGACCA | 240 |
| AGCAGGCCTT | TATCAAAGCC | ACGGGGAAGA | AGGAAGATGA | ACATGTGGTT | GCTTCTGATG | 300 |
| CAGACCTGGA | TGCCAAGCTG | GAGCTGTTTC | ACTCAATCCA | GAGAACCTGT | CTGGACTTGT | 360 |
| CTAAAGCAAT | CGTGCTCTAT | CAAAAGAGAA | TATGTTTCTT | GTCTCAAGAG | GAAAATGAAC | 420 |
| TGGGAAAGTT | TCTTCGATCT | CAAGGCTTCC | AAGACAAAAC | CCGAGCAGGA | AAAATGATGC | 480 |
| AAGCCACGGG | CAAGGCCCTC | TGCTTTTCCT | CCCAGCAAAG | GTTGGCCTTG | AGAAACCCTT | 540 |
| TGTGTCGATT | TCACCAAGAA | GTAGAAACTT | TTAGACATCG | GCCATCTCT | GATACCTGGC | 600 |
| TGACAGTGAA | CCGCATGGAG | CAGTACAGGA | CAGAATACAG | AGGAGCGTTG | TTATGGATGA | 660 |
| AGGACGTGTC | TCAGGAACTT | GATCCAGACC | TCTACAAGCA | AATGGAGAAG | TTCAGGAAGG | 720 |
| TGCAGACACA | AGTCCGCCTT | GCGAAAAAAA | ACTTTGACAA | GTTGAAGATG | GATGTGTGTC | 780 |
| AAAAGGTGGA | TCTTCTTGGA | GCAAGCAGAT | GTAACCTCTT | ATCTCACATG | CTAGCAACAT | 840 |
| ACCAGACCAC | TCTGCTCCAC | TTTTGGGAGA | AAACTTCTCA | CACCATGGCA | GCCATTCATG | 900 |
| AGAGCTTCAA | AGGTTATCAA | CCATATGAAT | TCACAACGTT | AAAGAGCTTA | CAAGACCCCA | 960 |
| TGAAGAAGCT | AGTTGAGAAG | GAAGGGAAGA | AGACCTCCTG | GAGGGAAAAC | CGGGAGGCTG | 1020 |
| TGGCACCAGA | GCCGAGGCAG | TTAATTTCTT | TGGAGGATGA | GCACAAAGAT | TCATCTACTT | 1080 |
| ATAAGACTGA | AGAGGGAACA | AGCGTTTTGT | CTTCCGTAGA | CAAAGGTTCT | GTACATGACA | 1140 |
| CATGCTCAGG | ACCCATAGAT | GAACTATTAG | ACGGGAAACC | CGAGGAAGCG | TGCCTGGGTC | 1200 |
| CCACGGCAGG | GACCCCAGAA | CCTGAAAGTG | GGACAAGGA | TGACCTCTTG | CTGTTGAATG | 1260 |
| AGATCTTCAG | CACTTCCTGC | CTGGATGAGG | GAGAGTTCAG | CAGAGAGTGG | GCTGCAGTGT | 1320 |
| TTGGAGATGA | CCGGCTAAAG | GAGCCAGCAC | CCATGGGGGC | CAAGGAGAG | CCAGACCCCA | 1380 |
| AGCCCCAGAT | AGGCTCCGGA | TTCCTTCCGT | CGCAGCTTTT | AGACCAAAAT | ATGAAAGATC | 1440 |
| TCCAGGCCTC | TCTGCAAGAG | CCTGCCAAGG | CTGCCTCGGA | CCTGACTGCC | TGGTTCAGCC | 1500 |
| TCTTTGCTGA | CCTCGACCCC | TTATCAAACC | CTGATGCTGT | TGGGAAAACT | GATAAAGAAC | 1560 |
| ACGAATTGCT | CAATGCATGA | GTCTGCAACC | TTCAACAGGG | AGCCCTCGGG | CCACTCCGCG | 1620 |
| GCACCTCATC | CAGGGCTTGC | AGAAGTCTAA | TATGCTCGGT | GTGCTGTTTT | AATATTTACA | 1680 |
| TGCCATTTTA | ATAAAATGAG | AGGGTCAAGG | CCCTGTTTCT | ATCGCTATAA | AAAAAAA | 1738 |

(2) INFORMATION FOR SEQ ID NO: 30:

(i) SEQUENCE CHARACTERISTICS:
        (A) LENGTH: 1642 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

GAGAGAGCTC GTGCCGAATT CGGCACGAGT AGAAAGAGA AGAAACATG TCAGGACACA      60

```
AATGTTATTC CTGGGAGTTG CAGGACCGGT TTGCTCAAGA TAAGTCAGTT GTCAATAAGA    120

TGCAGCAGAA ATATTGGGAG ACCAAGCAGG CCTTTATCAA AGCCACGGGG AAGAAGGAAG    180

ATGAACATGT GGTTGCTTCT GATGCAGACC TGGATGCCAA GCTGGAGCTG TTTCACTCAA    240

TCCAGAGAAC CTGTCTGGAC TTGTCTAAAG CAATCGTGCT CTATCAAAAG AGAATATGTT    300

TCTTGTCTCA AGAGGAAAAT GAACTGGGAA AGTTTCTTCG ATCTCAAGGC TTCCAAGACA    360

AAACCCGAGC AGGAAAAATG ATGCAAGCCA CGGGCAAGGC CCTCTGCTTT TCCTCCCAGC    420

AAAGGTTGGC CTTGAGAAAC CCTTTGTGTC GATTTCACCA AGAAGTAGAA ACTTTTAGAC    480

ATCGGGCCAT CTCTGATACC TGGCTGACAG TGAACCGCAT GGAGCAGTAC AGGACAGAAT    540

ACAGAGGAGC GTTGTTATGG ATGAAGGACG TGTCTCAGGA ACTTGATCCA GACCTCTACA    600

AGCAAATGGA GAAGTTCAGG AAGGTGCAGA CACAAGTCCG CCTTGCGAAA AAAAACTTTG    660

ACAAGTTGAA GATGGATGTG TGTCAAAAGG TGGATCTTCT TGGAGCAAGC AGATGTAACC    720

TCTTATCTCA CATGCTAGCA ACATACCAGA CCACTCTGCT CCACTTTTGG GAGAAAACTT    780

CTCACACCAT GGCAGCCATT CATGAGAGCT TCAAAGGTTA TCAACCATAT GAATTCACAA    840

CGTTAAAGAG CTTACAAGAC CCCATGAAGA AGCTAGTTGA GAAGGAAGGG AAGAAGACCT    900

CCTGGAGGGA AAACCGGGAG GCTGTGGCAC CAGAGCCGAG GCAGTTAATT TCTTTGGAGG    960

ATGAGCACAA AGATTCATCT ACTTATAAGA CTGAGGAGGG AACAAGCGTT TTGTCTTCCG    1020

TAGACAAAGG TTCTGTACAT GACACATGCT CAGGACCCAT AGATGAACTA TTAGACGGGA    1080

AACCCGAGGA AGCGTGCCTG GGTCCCACGG CAGGGACCCC AGAACCTGAA AGTGGGGACA    1140

AGGATGACCT CTTGCTGTTG AATGAGATCT TCAGCACTTC CTGCCTGGAT GAGGGAGAGT    1200

TCAGCAGAGA GTGGGCTGCA GTGTTTGGAG ATGACCGGCT AAAGGAGCCA GCACCCATGG    1260

GGGCCCAAGG AGAGCCAGAC CCCAAGCCCC AGATAGGCTC CGGATTCCTT CCGTCGCAGC    1320

TTTTAGACCA AAATATGAAA GATCTCCAGG CCTCTCTGCA AGAGCCTGCC AAGGCTGCCT    1380

CGGACCTGAC TGCCTGGTTC AGCCTCTTTG CTGACCTCGA CCCCTTATCA AACCCTGATG    1440

CTGTTGGGAA AACTGATAAA GAACACGAAT TGCTCAATGC ATGAGTCTGC AACCTTCAAC    1500

AGGGAGCCCT CGGGCCACTC CGCGGCACCT CATCCAGGGC TTGCAGAAGT CTAAATATGCT   1560

CGGTGTGCTG TTTTAATATT TACATGCCAT TTTAATAAAA TGAGAGGGTC AAGGCCCTGT    1620

TTCTATCGCT ATAAAAAAAA AA                                            1642
```

(2) INFORMATION FOR SEQ ID NO: 31:

(i) SEQUENCE CHARACTERISTICS:
    (A) LENGTH: 1550 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 31:

```
GGAACGAGAG AAGAAAACAT GTCAGGACAC AAATGTTATT CCTGGGAGTT GCAGGACCGG    60

TTTGCTCAAG ATAAGTCAGT TGTCAATAAG ATGCAGCAGA AATATTGGGA GACCAAGCAG    120

GCCTTTATCA AAGCCACGGG GAAGAAGGAA GATGAACATG TGGTTGCTTC TGATGCAGAC    180

CTGGATGCCA AGCTGGAGCT GTTTCACTCA ATCCAGAGAA CCTGTCTGGA CTTGTCTAAA    240

GCAATCGTGC TCTATCAAAA GAGAATATGT TTCTTGTCTC AAGAGGAAAA TGAACTGGGA    300

AAGTTTCTTC GATCTCAAGG CTTCCAAGAC AAAACCCGAG CAGGAAAAAT GATGCAAGCC    360
```

-continued

```
ACGGGCAAGG CCCTCTGCTT TTCCTCCCAG CAAAGGTTGG CCTTGAGAAA CCCTTTGTGT    420

CGATTTCACC AAGAAGTAGA AACTTTTAGA CATCGGGCCA TCTCTGATAC CTGGCTGACA    480

GTGAACCGCA TGGAGCAGTA CAGGACAGAA TACAGAGGAG CGTTGTTATG GATGAAGGAC    540

GTGTCTCAGG AACTTGATCC AGACCTCTAC AAGCAAATGG AGAAGTTCAG GAAGGTGCAG    600

ACACAAGTCC GCCTTGCGAA AAAAACTTT GACAAGTTGA AGATGGATGT GTGTCAAAAG    660

GTGGATCTTC TTGGAGCAAG CAGATGTAAC CTCTTATCTC ACATGCTAGC AACATACCAG    720

ACCACTCTGC TCCACTTTTG GGAGAAAACT TCTCACACCA TGGCAGCCAT TCATGAGAGC    780

TTCAAAGGTT ATCAACCATA TGAATTCACA ACGTTAAAGA GCTTACAAGA CCCCATGAAG    840

AAGCTAGTTG AGAAGGAAGG GAAGAAGACC TCCTGGAGGG AAAACCGGGA GGCTGTGGCA    900

CCAGAGCCGA GGCAGTTAAT TTCTTTGGAG GATGAGCACA AAGATTCATC TACTTATAAG    960

AGACCCATAG ATGAACTATT AGACGGGAAA CCCGAGGAAG CGTGCCTGGG TCCCACGGCA   1020

GGGACCCCAG AACCTGAAAG TGGGACAAGG GATGACCTCT TGCTGTTGAA TGAGATCTTC   1080

AGCACTTCCT GCCTGGATGA GGGAGAGTTC AGCAGAGAGT GGGCTGCAGT GTTTGGAGAT   1140

GACCGGCTAA AGGAGCCAGC ACCCATGGGG GCCCAAGGAG AGCCAGACCC CAAGCCCCAG   1200

ATAGGCTCCG GATTCCTTCC GTCGCAGCTT TTAGACCAAA ATATGAAAGA CTCCAGGCC   1260

TCTCTGCAAG AGCCTGCCAA GGCTGCCTCG GACCTGACTG CCTGGTTCAG CCTCTTTGCT   1320

GACCTCGACC CCTTATCAAA CCCTGATGCT GTTGGGAAAA CTGATAAAGA ACACGAATTG   1380

CTCAATGCAT GAGTCTGCAA CCTTCAACAG GGAGCCCTCG GGCCACTCCG CGGCACCTCA   1440

TCCAGGGCTT GCAGAAGTCT AATATGCTCG GTGTGCTGTT TTAATATTTA CATGCCATTT   1500

TAATAAAATG AGAGGGTCAA GGCCCTGTTT CTATCGCTAT AAAAAAAAAA              1550
```

(2) INFORMATION FOR SEQ ID NO: 32:

(i) SEQUENCE CHARACTERISTICS:
        (A) LENGTH: 478 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 32:

```
Met Ser Gly His Lys Cys Tyr Ser Trp Glu Leu Gln Asp Arg Phe Ala
1               5                   10                  15

Gln Asp Lys Ser Val Val Asn Lys Met Gln Gln Lys Tyr Trp Glu Thr
            20                  25                  30

Lys Gln Ala Phe Ile Lys Ala Thr Gly Lys Lys Glu Asp Glu His Val
        35                  40                  45

Val Ala Ser Asp Ala Asp Leu Asp Ala Lys Leu Glu Leu Phe His Ser
    50                  55                  60

Ile Gln Arg Thr Cys Leu Asp Leu Ser Lys Ala Ile Val Leu Tyr Gln
65                  70                  75                  80

Lys Arg Ile Cys Phe Leu Ser Gln Glu Glu Asn Glu Leu Gly Lys Phe
                85                  90                  95

Leu Arg Ser Gln Gly Phe Gln Asp Lys Thr Arg Ala Gly Lys Met Met
            100                 105                 110

Gln Ala Thr Gly Lys Ala Leu Cys Phe Ser Ser Gln Gln Arg Leu Ala
        115                 120                 125

Leu Arg Asn Pro Leu Cys Arg Phe His Gln Glu Val Glu Thr Phe Arg
    130                 135                 140
```

```
His Arg Ala Ile Ser Asp Thr Trp Leu Thr Val Asn Arg Met Glu Gln
145                 150                 155                 160

Tyr Arg Thr Glu Tyr Arg Gly Ala Leu Leu Trp Met Lys Asp Val Ser
            165                 170                 175

Gln Glu Leu Asp Pro Asp Leu Tyr Lys Gln Met Glu Lys Phe Arg Lys
            180                 185                 190

Val Gln Thr Gln Val Arg Leu Ala Lys Lys Asn Phe Asp Lys Leu Lys
        195                 200                 205

Met Asp Val Cys Gln Lys Val Asp Leu Leu Gly Ala Ser Arg Cys Asn
    210                 215                 220

Leu Leu Ser His Met Leu Ala Thr Tyr Gln Thr Thr Leu Leu His Phe
225                 230                 235                 240

Trp Glu Lys Thr Ser His Thr Met Ala Ala Ile His Glu Ser Phe Lys
                245                 250                 255

Gly Tyr Gln Pro Tyr Glu Phe Thr Thr Leu Lys Ser Leu Gln Asp Pro
                260                 265                 270

Met Lys Lys Leu Val Glu Lys Glu Gly Lys Lys Thr Ser Trp Arg Glu
            275                 280                 285

Asn Arg Glu Ala Val Ala Pro Glu Pro Arg Gln Leu Ile Ser Leu Glu
290                 295                 300

Asp Glu His Lys Asp Ser Ser Thr Tyr Lys Thr Glu Gly Thr Ser
305                 310                 315                 320

Val Leu Ser Ser Val Asp Lys Gly Ser Val His Asp Thr Cys Ser Gly
                325                 330                 335

Pro Ile Asp Glu Leu Leu Asp Gly Lys Pro Glu Glu Ala Cys Leu Gly
            340                 345                 350

Pro Thr Ala Gly Thr Pro Glu Pro Glu Ser Gly Asp Lys Asp Asp Leu
        355                 360                 365

Leu Leu Leu Asn Glu Ile Phe Ser Thr Ser Cys Leu Asp Glu Gly Glu
            370                 375                 380

Phe Ser Arg Glu Trp Ala Ala Val Phe Gly Asp Asp Arg Leu Lys Glu
385                 390                 395                 400

Pro Ala Pro Met Gly Ala Gln Gly Glu Pro Asp Pro Lys Pro Gln Ile
                405                 410                 415

Gly Ser Gly Phe Leu Pro Ser Gln Leu Leu Asp Gln Asn Met Lys Asp
                420                 425                 430

Leu Gln Ala Ser Leu Gln Glu Pro Ala Lys Ala Ala Ser Asp Leu Thr
            435                 440                 445

Ala Trp Phe Ser Leu Phe Ala Asp Leu Asp Pro Leu Ser Asn Pro Asp
450                 455                 460

Ala Val Gly Lys Thr Asp Lys Glu His Glu Leu Leu Asn Ala
465                 470                 475
```

(2) INFORMATION FOR SEQ ID NO: 33:

(i) SEQUENCE CHARACTERISTICS:
        (A) LENGTH: 457 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 33:

```
Met Ser Gly His Lys Cys Tyr Ser Trp Glu Leu Gln Asp Arg Phe Ala
1               5                   10                  15
```

```
Gln Asp Lys Ser Val Val Asn Lys Met Gln Gln Lys Tyr Trp Glu Thr
             20                  25                  30

Lys Gln Ala Phe Ile Lys Ala Thr Gly Lys Lys Glu Asp Glu His Val
         35                  40                  45

Val Ala Ser Asp Ala Asp Leu Asp Ala Lys Leu Glu Leu Phe His Ser
 50                  55                  60

Ile Gln Arg Thr Cys Leu Asp Leu Ser Lys Ala Ile Val Leu Tyr Gln
 65                  70                  75                  80

Lys Arg Ile Cys Phe Leu Ser Gln Glu Glu Asn Glu Leu Gly Lys Phe
                 85                  90                  95

Leu Arg Ser Gln Gly Phe Gln Asp Lys Thr Arg Ala Gly Lys Met Met
            100                 105                 110

Gln Ala Thr Gly Lys Ala Leu Cys Phe Ser Ser Gln Gln Arg Leu Ala
        115                 120                 125

Leu Arg Asn Pro Leu Cys Arg Phe His Gln Glu Val Glu Thr Phe Arg
130                 135                 140

His Arg Ala Ile Ser Asp Thr Trp Leu Thr Val Asn Arg Met Glu Gln
145                 150                 155                 160

Tyr Arg Thr Glu Tyr Arg Gly Ala Leu Leu Trp Met Lys Asp Val Ser
                165                 170                 175

Gln Glu Leu Asp Pro Asp Leu Tyr Lys Gln Met Glu Lys Phe Arg Lys
            180                 185                 190

Val Gln Thr Gln Val Arg Leu Ala Lys Lys Asn Phe Asp Lys Leu Lys
        195                 200                 205

Met Asp Val Cys Gln Lys Val Asp Leu Leu Gly Ala Ser Arg Cys Asn
    210                 215                 220

Leu Leu Ser His Met Leu Ala Thr Tyr Gln Thr Thr Leu Leu His Phe
225                 230                 235                 240

Trp Glu Lys Thr Ser His Thr Met Ala Ala Ile His Glu Ser Phe Lys
                245                 250                 255

Gly Tyr Gln Pro Tyr Glu Phe Thr Thr Leu Lys Ser Leu Gln Asp Pro
            260                 265                 270

Met Lys Lys Leu Val Glu Lys Glu Gly Lys Lys Thr Ser Trp Arg Glu
    275                 280                 285

Asn Arg Glu Ala Val Ala Pro Glu Pro Arg Gln Leu Ile Ser Leu Glu
290                 295                 300

Asp Glu His Lys Asp Ser Ser Thr Tyr Leu Arg Pro Ile Asp Glu Leu
305                 310                 315                 320

Leu Asp Gly Lys Pro Glu Glu Ala Cys Leu Gly Pro Thr Ala Gly Thr
                325                 330                 335

Pro Glu Pro Glu Ser Gly Asp Lys Asp Leu Leu Leu Asn Glu
            340                 345                 350

Ile Phe Ser Thr Ser Cys Leu Asp Glu Gly Glu Phe Ser Arg Glu Trp
        355                 360                 365

Ala Ala Val Phe Gly Asp Asp Arg Leu Lys Glu Pro Ala Pro Met Gly
    370                 375                 380

Ala Gln Gly Glu Pro Asp Pro Lys Pro Gln Ile Gly Ser Gly Phe Leu
385                 390                 395                 400

Pro Ser Gln Leu Leu Asp Gln Asn Met Lys Asp Leu Gln Ala Ser Leu
                405                 410                 415

Gln Glu Pro Ala Lys Ala Ala Ser Asp Leu Thr Ala Trp Phe Ser Leu
            420                 425                 430
```

```
Phe Ala Asp Leu Asp Pro Leu Ser Asn Pro Asp Ala Val Gly Lys Thr
        435                 440                 445

Asp Lys Glu His Glu Leu Leu Asn Ala
        450                 455

(2) INFORMATION FOR SEQ ID NO: 34:

(i) SEQUENCE CHARACTERISTICS:
        (A) LENGTH: 478 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 34:

Met Ser Gly His Lys Cys Tyr Ser Trp Glu Leu Gln Asp Arg Phe Ala
1               5                  10                  15

Gln Asp Lys Ser Val Val Asn Lys Met Gln Gln Lys Tyr Trp Glu Thr
            20                  25                  30

Lys Gln Ala Phe Ile Lys Ala Thr Gly Lys Lys Glu Asp Glu His Val
        35                  40                  45

Val Ala Ser Asp Ala Asp Leu Asp Ala Lys Leu Glu Leu Phe His Ser
50                  55                  60

Ile Gln Arg Thr Cys Leu Asp Leu Ser Lys Ala Ile Val Leu Tyr Gln
65                  70                  75                  80

Lys Arg Ile Cys Phe Leu Ser Gln Glu Glu Asn Glu Leu Gly Lys Phe
                85                  90                  95

Leu Arg Ser Gln Gly Phe Gln Asp Lys Thr Arg Ala Gly Lys Met Met
            100                 105                 110

Gln Ala Thr Gly Lys Ala Leu Cys Phe Ser Ser Gln Gln Arg Leu Ala
        115                 120                 125

Leu Arg Asn Pro Leu Cys Arg Phe His Gln Glu Val Glu Thr Phe Arg
130                 135                 140

His Arg Ala Ile Ser Asp Thr Trp Leu Thr Val Asn Arg Met Glu Gln
145                 150                 155                 160

Tyr Arg Thr Glu Tyr Arg Gly Ala Leu Leu Trp Met Lys Asp Val Ser
                165                 170                 175

Gln Glu Leu Asp Pro Asp Leu Tyr Lys Gln Met Glu Lys Phe Arg Lys
            180                 185                 190

Val Gln Thr Gln Val Arg Leu Ala Lys Lys Asn Phe Asp Lys Leu Lys
        195                 200                 205

Met Asp Val Cys Gln Lys Val Asp Leu Leu Gly Ala Ser Arg Cys Asn
210                 215                 220

Leu Leu Ser His Met Leu Ala Thr Tyr Gln Thr Thr Leu Leu His Phe
225                 230                 235                 240

Trp Glu Lys Thr Ser His Thr Met Ala Ala Ile His Glu Ser Phe Lys
                245                 250                 255

Gly Tyr Gln Pro Tyr Glu Phe Thr Thr Leu Lys Ser Leu Gln Asp Pro
            260                 265                 270

Met Lys Lys Leu Val Glu Lys Glu Gly Lys Lys Thr Ser Trp Arg Glu
        275                 280                 285

Asn Arg Glu Ala Val Ala Pro Glu Pro Arg Gln Leu Ile Ser Leu Glu
290                 295                 300

Asp Glu His Lys Asp Ser Ser Tyr Lys Tyr Thr Glu Glu Gly Thr Ser
305                 310                 315                 320
```

```
Val Leu Ser Ser Val Asp Lys Gly Ser Val His Asp Thr Cys Ser Gly
            325                 330                 335

Pro Ile Asp Glu Leu Leu Asp Gly Lys Pro Glu Glu Ala Cys Leu Gly
            340                 345                 350

Pro Thr Ala Gly Thr Pro Glu Pro Glu Ser Gly Asp Lys Asp Asp Leu
            355                 360                 365

Leu Leu Asn Glu Ile Phe Ser Thr Ser Cys Leu Asp Glu Gly Glu
            370                 375                 380

Phe Ser Arg Glu Trp Ala Ala Val Phe Gly Asp Asp Arg Leu Lys Glu
385                 390                 395                 400

Pro Ala Pro Met Gly Ala Gln Gly Glu Pro Asp Pro Lys Pro Gln Ile
            405                 410                 415

Gly Ser Gly Phe Leu Pro Ser Gln Leu Leu Asp Gln Asn Met Lys Asp
            420                 425                 430

Leu Gln Ala Ser Leu Gln Glu Pro Ala Lys Ala Ala Ser Asp Leu Thr
            435                 440                 445

Ala Trp Phe Ser Leu Phe Ala Asp Leu Asp Pro Leu Ser Asn Pro Asp
450                 455                 460

Ala Val Gly Lys Thr Asp Lys Glu His Glu Leu Leu Asn Ala
465                 470                 475

(2) INFORMATION FOR SEQ ID NO: 35:

(i) SEQUENCE CHARACTERISTICS:
        (A) LENGTH: 494 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

CTCCGATCTC CGCTGAGAGG CTCCTGGGGG CCGGGGCTCC GAGGAAAATG GTTCGATGTT    60

ATTAAAAATG AATCTTAAGA AGAAAAATGA ATCACAGCAG TTAAACTATG GAGTTCTGCT   120

ACTTGTAAGA AGTGGAGAAG CCTGAGATTA CATCACTGAC CCTTGATCCT CCACTGAGCT   180

AAAACACCAG CTGGTAATTG CCTATGATTT TATAGACTTC CCTCCATCTG CTGGGTCCAA   240

GTGTCCGTCT GACTGCTCTG GTACCGGAGC ATCTTTATTT CTGCATCTAA ACTTGTAAAA   300

AGCACATCGA ATCTTGTTCC CCAGGAGAAA ATCTTCAATG TAACCATTTT CAATGTATCC   360

GATGATACAA GCGCATTGTA ATCTCCAGGT AGAAGCAGCT TTATCAGTGG AAAGGGTTTA   420

ATAGAACATA TCCTATCATG CTTTTTCTCT GCCCCTTCTC AAATCATCAG CAGTAGAAAA   480

GAGAAGAAAA CATG                                                     494

(2) INFORMATION FOR SEQ ID NO: 36:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

GAGAGAGAGC TCGTGCCGAA TTCGGCACGA GCTCCGCCGG GAACCTCCTG GGGGCCGGAG    60

CACCAAGGTT TAATATAACT TATCCTCTCA TGATTTTTTC CTGCCCCTTC TCAAATCATC   120

GGCAATAGAA AAGAGAAGAA AACATG                                        146
```

(2) INFORMATION FOR SEQ ID NO: 37:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

```
GAGAGAGCTC GTGCCGAATT CGGCACGAGT AGAAAAGAGA AGAAAACATG              50
```

(2) INFORMATION FOR SEQ ID NO: 38:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

```
GCGCTCCGAC CTCGGTCGGG AGGCTCCTGG GGNCCGGGGC TCCGAGGT                48
```

(2) INFORMATION FOR SEQ ID NO: 39:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

```
GCTGCAGGAA GCAGCAGGAG ACGCCCGGCA GCCGGGACGG TCGGGACGC CTGAAGAANG    60

AAGAAGAAAA CATG                                                    74
```

(2) INFORMATION FOR SEQ ID NO: 40:

(i) SEQUENCE CHARACTERISTICS:
        (A) LENGTH: 483 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 40:

```
Met Ser Gly His Lys Cys Ser Tyr Pro Trp Asp Leu Gln Asp Arg Tyr
1               5                   10                  15

Ala Gln Asp Lys Ser Val Val Asn Lys Met Gln Gln Lys Tyr Trp Glu
                20                  25                  30

Thr Lys Gln Ala Phe Ile Lys Ala Thr Gly Lys Lys Glu Asp Glu His
            35                  40                  45

Val Val Ala Ser Asp Ala Asp Leu Asp Ala Lys Leu Glu Leu Phe His
        50                  55                  60

Ser Ile Gln Arg Thr Cys Leu Asp Leu Ser Lys Ala Ile Val Leu Tyr
65                  70                  75                  80

Gln Lys Arg Ile Cys Phe Leu Ser Gln Glu Glu Asn Glu Leu Gly Lys
                85                  90                  95
```

```
Phe Leu Arg Ser Gln Gly Phe Gln Asp Lys Thr Arg Ala Gly Lys Met
            100                 105                 110

Met Gln Ala Thr Gly Lys Ala Leu Cys Phe Ser Ser Gln Gln Arg Leu
            115                 120                 125

Ala Leu Arg Asn Pro Leu Cys Arg Phe His Gln Glu Val Glu Thr Phe
            130                 135                 140

Arg His Arg Ala Ile Ser Asp Thr Trp Leu Thr Val Asn Arg Met Glu
145                 150                 155                 160

Gln Cys Arg Thr Glu Tyr Arg Gly Ala Leu Leu Trp Met Lys Asp Val
                165                 170                 175

Ser Gln Glu Leu Asp Pro Asp Leu Tyr Lys Gln Met Glu Lys Phe Arg
            180                 185                 190

Lys Val Gln Thr Gln Val Arg Leu Ala Lys Lys Asn Phe Asp Lys Leu
            195                 200                 205

Lys Met Asp Val Cys Gln Lys Val Asp Leu Leu Gly Ala Ser Arg Cys
            210                 215                 220

Asn Leu Leu Ser His Met Leu Ala Thr Tyr Gln Thr Thr Leu Leu His
225                 230                 235                 240

Phe Trp Glu Lys Thr Ser His Thr Met Ala Ala Ile His Glu Ser Phe
                245                 250                 255

Lys Gly Tyr Gln Pro Tyr Glu Phe Thr Thr Leu Lys Ser Leu Gln Asp
            260                 265                 270

Pro Met Lys Lys Leu Val Glu Lys Glu Lys Lys Lys Ile Asn Gln
            275                 280                 285

Gln Glu Ser Thr Asp Ala Ala Val Gln Glu Pro Ser Gln Leu Ile Ser
            290                 295                 300

Leu Glu Glu Glu Asn Gln Arg Lys Glu Ser Ser Ser Phe Lys Thr Glu
305                 310                 315                 320

Asp Gly Lys Ser Ile Leu Ser Ala Leu Asp Lys Gly Ser Thr His Thr
                325                 330                 335

Ala Cys Ser Gly Pro Ile Asp Glu Leu Leu Asp Met Lys Ser Glu Glu
            340                 345                 350

Gly Ala Cys Leu Gly Pro Val Ala Gly Thr Pro Glu Pro Glu Gly Ala
            355                 360                 365

Asp Lys Asp Asp Leu Leu Leu Leu Ser Glu Ile Phe Asn Ala Ser Ser
            370                 375                 380

Leu Glu Glu Gly Glu Phe Ser Lys Glu Trp Ala Ala Val Phe Gly Asp
385                 390                 395                 400

Gly Gln Val Lys Glu Pro Val Pro Thr Met Ala Leu Gly Glu Pro Asp
                405                 410                 415

Pro Lys Ala Gln Thr Gly Ser Gly Phe Leu Pro Ser Gln Leu Leu Asp
            420                 425                 430

Gln Asn Met Lys Asp Leu Gln Ala Ser Leu Gln Glu Pro Ala Lys Ala
            435                 440                 445

Ala Ser Asp Leu Thr Ala Trp Phe Ser Leu Phe Ala Asp Leu Asp Pro
            450                 455                 460

Leu Ser Asn Pro Asp Ala Val Gly Lys Thr Asp Lys Glu His Glu Leu
465                 470                 475                 480

Leu Asn Ala
```

(2) INFORMATION FOR SEQ ID NO: 41:

(i) SEQUENCE CHARACTERISTICS:
        (A) LENGTH: 87 amino acids (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 41:

Met Ser Gly His Lys Cys Ser Tyr Pro Trp Asp Leu Gln Asp Arg Tyr
1               5                   10                  15

Ala Gln Asp Lys Ser Val Val Asn Lys Met Gln Gln Lys Tyr Trp Glu
            20                  25                  30

Thr Lys Gln Ala Phe Ile Lys Ala Thr Gly Lys Lys Glu Asp Glu His
        35                  40                  45

Val Val Ala Ser Asp Ala Asp Leu Asp Ala Lys Leu Glu Leu Phe His
    50                  55                  60

Ser Ile Gln Arg Thr Cys Leu Asp Leu Ser Lys Ala Ile Val Leu Tyr
65                  70                  75                  80

Gln Lys Arg Ile Cys Ser Phe
                85

(2) INFORMATION FOR SEQ ID NO: 42:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

Glu Phe Lys Ala Asp Glu Lys Lys Phe Trp Gly Lys Tyr Leu
1               5                   10

(2) INFORMATION FOR SEQ ID NO: 43:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 43:

TATAATATAA CTTATCCTCT CATGCTTTTT TCCTGCCCCT TCTCCCCAAA TCATCAACAA        60

TAGAANGAAG AAGAAAACAT G                                                 81

(2) INFORMATION FOR SEQ ID NO: 44:

(i) SEQUENCE CHARACTERISTICS:
        (A) LENGTH: 1742 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 44:

ATAATATAAC TTATCCTCTC ATGCTTTTTT CCTGCCCCTT CTCCCCAAAT CATCAACAAT        60

AGAAGAAGAA GAAAACATGT CAGGACACAA ATGCAGTTAT CCCTGGGACT TACAGGATCG       120

ATATGCTCAA GATAAGTCAG TTGTAAATAA GATGCAACAG AAATATTGGG AGACGAAGCA       180

GGCCTTTATT AAAGCCACAG GGAAGAAGGA AGATGAACAT GTTGTTGCCT CTGACGCGGA       240

-continued

```
CCTGGATGCC AAGCTAGAGC TGTTTCATTC AATTCAGAGA ACCTGTCTGG ACTTATCGAA      300

AGCAATTGTA CTCTATCAAA AGGGGATATG TTCATTTTAG GAGGCCAAGG CAGGAGGATC      360

ACTTGGAGCC AGGAGTTTGA GACCAGCCTG GGCAACAAAG TGAGACCCCC ATCTCTACAA      420

AAAATAAAAA CACTTAAAAA TTATCCGGGT ACCGTGCATG TGCAGTCCCA GCTACTCAGG      480

AGGCTGAGGC AGGAGGATCA CAGTGACCTA TAATGAGCCG TTGTGCTCCA GCCTGGGCGA      540

CAGAAGTCTT GTCTCAAGAA GAAAACGAAC TGGGAAAATT TCTTCGATCC CAAGGTTTCC      600

AAGATAAAAC CAGAGCAGGA AAGATGATGC AAGCGACAGG AAAGGCCCTC TGCTTTTCTT      660

CCCAGCAAAG GTTGGCCTTA CGAAATCCTT TGTGTCGATT TCACCAAGAA GTGGAGACTT      720

TTCGGCATCG GGCCATCTCA GATACTTGGC TGACGGTGAA CCGCATGGAA CAGTGCAGGA      780

CGGAATATAG AGGAGCACTA TTATGGATGA AGGACGTGTC TCAGGAGCTT GATCCAGACC      840

TCTACAAGCA AATGGAGAAG TTCAGGAAGG TACAAACACA AGTGCGCCTT GCAAAAAAAA      900

ACTTTGACAA ATTGAAGATG GATGTTTGTC AAAAAGTGGA TCTTCTTGGA GCGAGCAGAT      960

GCAATCTCTT GTCTCACATG CTAGCAACAT ACCAGACCAC TCTGCTTCAT TTTTGGGAGA     1020

AAACTTCTCA CACTATGGCA GCCATCCATG AGAGTTTCAA AGGTTATCAA CCATATGAAT     1080

TTACTACTTT AAAGAGCTTA CAAGACCCTA TGAAAAAATT AGTTGAGAAA GAAGAGAAGA     1140

AGAAAATCAA CCAGCAGGAA AGTACAGATG CAGCCGTGCA GGAGCCGAGC CAATTAATTT     1200

CATTAGAGGA AGAAAACCAG CGCAAGGAAT CCTCTAGTTT TAAGACTGAA GATGGAAAAA     1260

GTATTTTATC TGCCTTAGAC AAAGGCTCTA CACATACTGC ATGCTCAGGA CCCATAGATG     1320

AACTATTAGA CATGAAATCT GAGGAAGGTG CTTGCCTGGG ACCAGTGGCA GGGACCCCGG     1380

AACCTGAAGG TGCTGACAAA GATGACCTGC TGCTGTTGAG TGAGATCTTC AATGCTTCCT     1440

CCTTGGAAGA GGGCGAGTTC AGCAAAGAGT GGGCCGCTGT GTTTGGAGAC GGCCAAGTGA     1500

AGGAGCCAGT GCCCACTATG GCCCTGGGAG AGCCAGACCC CAAGGCCCAG ACAGGCTCAG     1560

GTTTCCTTCC TTCGCAGCTT TTAGACCAAA ATATGAAAGA CTTACAGGCC TCGCTACAAG     1620

AACCTGCTAA GGCTGCCTCA GACCTGACTG CCTGGTTCAG CCTCTTCGCT GACCTCGACC     1680

CACTCTCAAA TCCTGATGCT GTTGGGAAAA CCGATAAAGA ACACGAATTG CTCAATGCAT     1740

GA                                                                   1742
```

(2) INFORMATION FOR SEQ ID NO: 45:

(i) SEQUENCE CHARACTERISTICS:
        (A) LENGTH: 214 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 45:

```
CATTTTAGGA GGCCAAGGCA GGAGGATCAC TTGGAGCCAG GAGTTTGAGA CCAGCCTGGG       60

CAACAAAGTG AGACCCCCAT CTCTACAAAA AATAAAAACA CTTAAAAATT ATCCGGGTAC      120

CGTGCATGTG CAGTCCCAGC TACTCAGGAG GCTGAGGCAG GAGGATCACA GTGACCTATA      180

ATGAGCCGTT GTGCTCCAGC CTGGGCGACA GAAG                                 214
```

(2) INFORMATION FOR SEQ ID NO: 46:

(i) SEQUENCE CHARACTERISTICS:
        (A) LENGTH: 8 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 46:

Phe Asp Lys Leu Lys Met Asp Val
1               5

(2) INFORMATION FOR SEQ ID NO: 47:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 47:

Phe Asp Lys Leu Lys His Leu Val
1               5

(2) INFORMATION FOR SEQ ID NO: 48:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 48:

Gly Ala Cys Leu Gly Pro
1               5

(2) INFORMATION FOR SEQ ID NO: 49:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 49:

Gly Ala Cys Leu Leu Pro
1               5
```

I claim:

1. A protein encoded by a nucleic acid molecule consisting of a nucleotide sequence selected from the group consisting of SEQ ID NO:3, SEQ ID NO:5, SEQ ID NO:29, SEQ ID NO:30 and SEQ ID NO:31.

2. A protein consisting of the amino acid sequence of SEQ ID NO 41 or a peptide fragment of said protein including the amino acid sequence of SEQ ID NO 23.

3. A method for detecting a subject at risk for diabetes comprising obtaining a serum sample from said subject and detecting antibodies in said sample reactive against p69 protein with an immunoassay employing a protein or peptide selected from the group consisting of:

(a) a protein consisting of the amino acid sequence of SEQ ID NO 41; and (b) a peptide fragment of said protein including the amino acid sequence of SEQ ID NO 23; an increased level of said antibodies over control values indicating that said subject is at risk for diabetes.

4. The method of claim 3 wherein the amino acid sequence of the peptide fragment is SEQ ID NO:23.

5. A method for detecting a subject at risk for diabetes comprising:

obtaining a sample containing T lymphocytes from said subject;

contacting the T lymphocytes, in the presence of an effective amount of interleukin 2, with a protein or peptide selected from the group consisting of:

(a) a protein consisting of the amino acid sequence of SEQ ID NO 41; and (b) a peptide fragment of said protein including the amino acid sequence of SEQ ID NO 23; and detecting a proliferative response of said T lymphocytes to the protein or peptide, said proliferative response indicating that said subject is at risk for diabetes.

6. A protein in accordance with claim 1 wherein the protein consists of an amino acid sequence selected from the group consisting of SEQ ID NO 32, SEQ NO ID 33 and SEQ NO ID 34.

7. The method of claim 5 wherein the T lymphocytes are contacted with the selected protein or peptide in serum free medium.

8. The method of claim 5 wherein the selected protein or peptide consists of the peptide of SEQ ID NO:23.

9. The method of claim 7 wherein the selected protein or peptide consists of the peptide of SEQ ID NO:23.

* * * * *